US008916184B2

(12) United States Patent
Klueh et al.

(10) Patent No.: US 8,916,184 B2
(45) Date of Patent: Dec. 23, 2014

(54) ARTIFICIAL TISSUE SYSTEMS AND USES THEREOF

(75) Inventors: Ulrike W. Klueh, New Britain, CT (US);
David I. Dorsky, Avon, CT (US);
Donald L. Kreutzer, Avon, CT (US)

(73) Assignee: University of Connecticut, Farmington, CT (US)

( * ) Notice: Subject to any disclaimer, the term of this patent is extended or adjusted under 35 U.S.C. 154(b) by 923 days.

(21) Appl. No.: 10/578,171

(22) PCT Filed: Nov. 5, 2004

(86) PCT No.: PCT/US2004/037302
§ 371 (c)(1),
(2), (4) Date: May 4, 2006

(87) PCT Pub. No.: WO2005/046445
PCT Pub. Date: May 26, 2005

(65) Prior Publication Data
US 2007/0077265 A1    Apr. 5, 2007

Related U.S. Application Data

(60) Provisional application No. 60/518,412, filed on Nov. 7, 2003.

(51) Int. Cl.
*A61K 35/12* (2006.01)
*A61B 5/145* (2006.01)
*C12N 5/00* (2006.01)
*A61L 27/38* (2006.01)
*A61B 5/00* (2006.01)

(52) U.S. Cl.
CPC ............. *A61B 5/686* (2013.01); *A61B 5/14532* (2013.01); *A61K 35/12* (2013.01); *C12N 5/0062* (2013.01); *A61L 27/38* (2013.01); *A61B 5/14503* (2013.01); *A61B 5/14546* (2013.01)
USPC ......................... 424/423; 424/93.21; 514/44 R

(58) Field of Classification Search
CPC combination set(s) only.
See application file for complete search history.

(56) References Cited

U.S. PATENT DOCUMENTS

| 4,685,900 | A | 8/1987 | Honard et al. | |
| 4,715,858 | A | 12/1987 | Lindstrom | |
| 4,829,000 | A | 5/1989 | Kleinman et al. | |
| 4,902,295 | A | 2/1990 | Walthall et al. | 623/11 |
| 4,997,443 | A | 3/1991 | Walthall et al. | 623/11 |
| 5,490,962 | A | 2/1996 | Cima et al. | 264/22 |
| 5,653,755 | A | 8/1997 | Ledergerber | |
| 5,798,113 | A | 8/1998 | Dionne et al. | |
| 5,814,091 | A | 9/1998 | Dahlberg et al. | |
| 5,834,001 | A | 11/1998 | Dionne et al. | |
| 5,893,888 | A | 4/1999 | Bell | 623/11 |
| 5,932,459 | A | 8/1999 | Sittinger et al. | 435/180 |
| 6,139,574 | A | 10/2000 | Vacanti et al. | 623/1.44 |
| 6,143,501 | A | 11/2000 | Sittinger et al. | 435/6 |
| 6,264,992 | B1 | 7/2001 | Voytik-Harbin et al. | |
| 6,284,284 | B1 | 9/2001 | Naughton | |
| 6,303,765 | B1 | 10/2001 | Bandman et al. | |
| 6,328,762 | B1 | 12/2001 | Anderson et al. | |
| 6,497,729 | B1 | 12/2002 | Moussy et al. | 623/23.57 |
| 6,596,296 | B1 * | 7/2003 | Nelson et al. | 424/426 |
| 6,673,596 | B1 * | 1/2004 | Sayler et al. | 435/288.7 |
| 6,716,246 | B1 | 4/2004 | Gonzalez | |
| 6,884,428 | B2 | 4/2005 | Binette et al. | |
| 7,048,856 | B2 | 5/2006 | Fissell, IV et al. | |
| 7,163,920 | B2 | 1/2007 | Dhanaraj et al. | |
| 7,396,537 | B1 | 7/2008 | Krupnick et al. | |
| 2001/0000802 | A1 * | 5/2001 | Soykan et al. | 623/1.13 |
| 2003/0087311 | A1 | 5/2003 | Wolf | |
| 2003/0099682 | A1 | 5/2003 | Moussy et al. | 424/423 |
| 2003/0138950 | A1 | 7/2003 | McAllister et al. | 435/366 |
| 2003/0139333 | A1 * | 7/2003 | Pawliuk et al. | 514/12 |
| 2005/0031689 | A1 | 2/2005 | Shults et al. | |

FOREIGN PATENT DOCUMENTS

| WO | WO 97/15655 | | 5/1997 |
| WO | WO 97/19344 | * | 5/1997 |
| WO | WO/99/45841 | | 9/1999 |

(Continued)

OTHER PUBLICATIONS

U. Klueh et al, "Use of vascular endothelial cell growth factor gene transfer to enhance implantable sensor function in vivo," *Journal of Biomedical Materials Research*, Part A, vol. 67A, Issue 4, pp. 1072-1086, Dec. 15, 2003, published online Oct. 27, 2003.
Pablo A. Jimenez, M.D. et al, "Tissue and cellular approaches to wound repair," *The American Journal of Surgery 187*, (Suppl to May 2004), pp. 56S-64S.
Abstract, "Use of vascular endothelial cell growth factor gene transfer to enhance biosensor function in vivo" 2003 Society for Biomaterials 29th Annual Meeting Transactions, Apr. 30, 2003.

(Continued)

*Primary Examiner* — Doug Schultz
(74) *Attorney, Agent, or Firm* — Alix, Yale & Ristas, LLP

(57) ABSTRACT

An implant system and a method for controlling the natural and artificial microenvironments surrounding an implanted device using an artificial tissue system (ATS) and includes methods of diagnostic and testing related thereto. The ATS, among other things, induce better integration, function, and extended lifespan of the devices at the site of implantation. The ATS includes cells, such as naturally occurring, engineered, and/or artificial cells; matrices such as natural, engineered, artificial and/or hybrid matrices; tissue response modifiers (TRM); and/or cell response modifiers (CRM). The specific composition of the ATS is based on the nature of the tissue in which ATS-device combination is implanted and the nature of the implant device, as well as the required function and lifespan of the implanted device. Additionally, the ATS, as well as ATSdevice combinations can be utilized in vitro to aid in the design of improved ATS, devices and ATS-device combinations for in \>ivo uses.

23 Claims, 27 Drawing Sheets

(56) References Cited

FOREIGN PATENT DOCUMENTS

| WO | WO 00/78929 | | 12/2000 |
|---|---|---|---|
| WO | WO 02/086107 | | 10/2002 |
| WO | WO 03/072155 | A1 | 9/2003 |
| WO | WO 03/072157 | * | 9/2003 |

OTHER PUBLICATIONS

PCT International Search Report and Written Opinion for International Application No. PCT/US04/37302 Nov. 9, 2005.

Maragoudakis et al., "Basement membrane biosynthesis as a target for developing inhibitors of angiogenesis with anti-tumor properties.," *Kidney Int.*, Jan. 1993;43(1):147-50, Abstract.

Grant et al., "Interaction of endothelial cells with a laminin A chain pepetide (SIKVAV) in vitro and induction of angiogenic behavior in vivo.," *J Cell Physiol*, Dec. 1992;153(3):614-25, Abstract.

Kibbey et al., "Role of the SIKVAV site of laminin in promotion of angiogenesis and tumor growth: an in vivo Matrigel model.," *J Natl Cancer Inst.*, Nov. 4, 1992;84(21):1633-8, Abstract.

Passaniti et al., "A simple, quantitative method for assessing angiogenesis and antiangiogenic agents using reconstituted basement membrane, heparin, and fibroblast growth factor.," *Lab Invest.*, Oct. 1992;67(4):519-28, Abstract.

Kaneko, "[Relationship between endothelial cells and extracellular matrix: investigation using the model of angiogenesis in vitro]," *Nippon Geka Hokan*, Mar. 1, 1992;61(2):134-49, Abstract.

Jerdan et al., "Extracellular matrix of newly forming vessels—an immunohistochemical study.," *Microvasc Res.*, Nov. 1991;42(3):255-65, Abstract.

Schultz et al., "Neovascular growth factors.," *Eye (Lond).*, 1991;5 (Pt 2):170-80, Abstract.

Nicosia et al., "Modulation of microvascular growth and morphogenesis by reconstituted basement membrane gel in three-dimensional cultures of rat aorta: a comparative study of angiogenesis in matrigel, collagen, fibrin, and plasma clot.," *In Vitro Cell Dev Biol.*, Feb. 1990;26(2):119-28, Abstract.

Brasken et al., "Fibronectin, laminin, and collagen types I, III, IV and V in the healing rat colon anastomosis," *Ann Chir Gynaecol.*, 1990;79(2):65-71, Abstract.

Mori et al., "Capillary growth from reversed rat aortic segments cultured in collagen gel.," *Acta Pathol Jpn.*, Dec. 1998;38(12):1503-12, Abstract.

Maragoudakis et al., "Inhibition of basement membrane biosynthesis prevents angiogenesis.," *J Pharmacol Exp Ther.*, Feb. 1998;244(2):729-33, Abstract.

Folkman et al., "A heparin-binding angiogenic protein—basic fibroblast growth factor—is stored within basement membrane.," *Am J Pathol.*, Feb. 1988;130(2):393-400, Abstract.

Maragoudakis et al., "Rate of basement membrane biosynthesis as an index to angiogenesis.," *Tissue Cell.*, 1988;20(4):531-9, Abstract.

Form et al., "Endothelial cell proliferation during angiogenesis. In vitro modulation by basement membrane components.," *Lab Invest.*, Nov. 1986;55(5):521-30, Abstract.

Apaja-Sarkkinen et al., "Immunohistochemical study of basement membrane proteins and type III procollagen in myelofibrosis.," *Br J Haematol.*, Jul. 1986;63(3):571-80, Abstract.

Kalebic et al., "Basement membrane collagen: degradation by migrating endothelial cells.," *Science.*, Jul. 15, 1983;221(4607):281-3, Abstract.

Glaser et al., "Degradation of basement membrane components by vascular endothelial cells: role in neovascularization.," *Ciba Found Symp.*, 1983;100:150-62, Abstract.

Oh et al., "VEGF and VEGF-C: Specific Induction of Angiogenesis and Lymphangiogenesis in the Differentiated Avian Chorioallantoic Membrane," *Developmental Biology*, 188, 96-102 (1997), Article No. DB978639.

Feldman et al., "A Continuous Glucose Sensor Based on Wired Enzyme™ Technology—Results from a 3-Day Trial in Patients with Type 1 Diabetes," *Diabetes Technology & Therapeutics*, vol. 5, Nov. 5, 2003, 769-779.

Supplementary European Search Report EP 04 81 6945, dated 4 Sep. 2009.

Jiang et al., Phagocyte responses to degradable polymers, 2007 Wiley Periodicals, Inc. J Biomed Mater Res 82A: 492-497, 2007.

Cao et al., The topographical effect of electrospun nanofibrous scaffolds on the in vivo and in vitro foreign body reaction, 2009 Wiley Periodicals, Inc. J Biomed Mater Res 93.

Ceonzo et al., Polyglycolic acid induced inflammation: Role of hydrolysis and resulting complement activation1, NIH Tissue Eng. Feb. 2006; 12(2): 301-308.

Ibim et al., Poly(anhydride-co-imides): in vivo biocompatibility in a rat model, Biomaterials 19 (1998) 941-951.

Gerritsen et al., Influence of inflammatory cells and serum on the performance of implantable glucose sensors, Journal of Biomedical Materials Research, vol. 54, 69-75 (2001).

Barbosa et al., Evaluation of the effect of the degree of acetylation on the inflammatory response to 3D porous chitosan scaffolds, 2009 Wiley Periodicals, Inc. J Biomed Mater.

Ueno et al., Topical formulations and wound healing applications of chitosan, Advanced Drug Delivery Reviews 52 (2001) 105-115.

Yoshioka et al., Improvement of Biocompatibility of Chitosan Fiber Modifiied by Ca-Phosphate Deposition through an Alternate Soaking Process . . . , vol. 50, No. 6 (2009).

Ueno et al., Chitosan accelerates the production of osteopontin from polymorphonuclear leukocytes, Biomaterials 22 (2001) 1667-1673.

Bartone et al., The reaction of the urinary tract to catgut and reconstituted collagen sutures, The Journal of Urology, vol. 101, 1969.

Altman et al., Silk-based biomaterials, Biomaterials 24 (2003) 401-416.

Gellynck et al., Biocompatibility and biodegradability of spider egg sac silk, J Mater Sci: Mater Med (2008) 19:2963-2970.

Vandevord et al., Evaluation of the biocompatibility of a chitosan scaffold in mice, 2001 John Wiley & Sons, Inc. J Biomed Mater Res 59: 585-590, 2002.

Wisniewski et al., Methods for reducing biosensor membrane biofouling, Colloids and Surfaces B: Biointerfaces 18 (2000), Relevant portions pp. 197-198, 204-205, 212-213.

Hubbell, Bioactive biomaterials, Current Opinion in Biotechnology 1999, 10:123-129, Relevant portion p. 125.

Wisniewski et al., Characterization of implantable biosensor membrane biofouling, Fresenius J Anal Chem (2000) 366:611-621, Relevant portions pp. 611 and 618.

\* cited by examiner

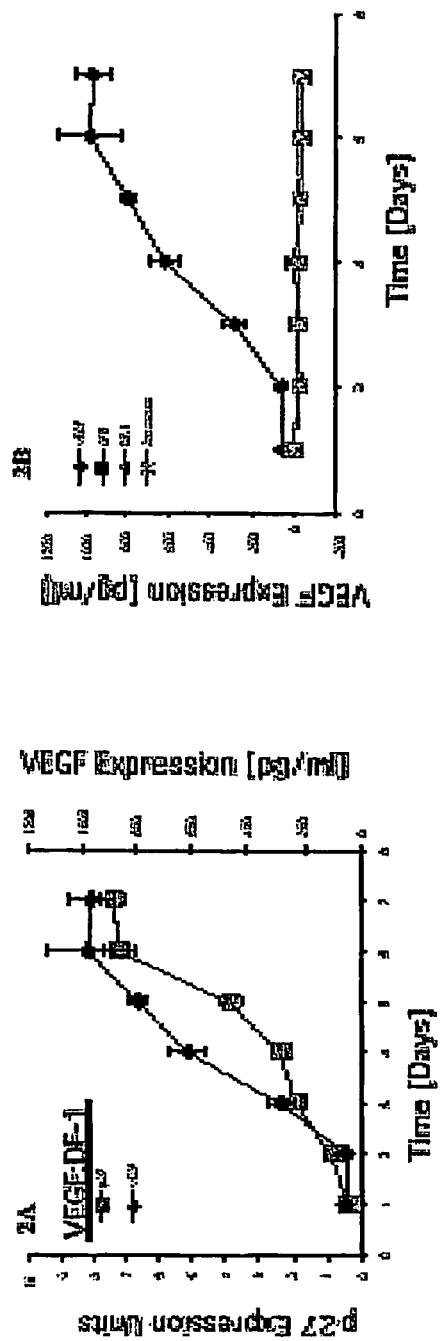
FIGURE 2
Figure 3B
Figure 3A

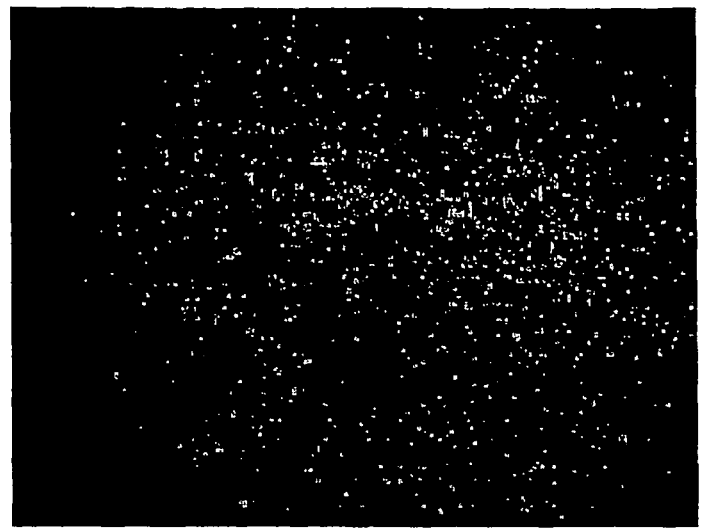
Figure 4
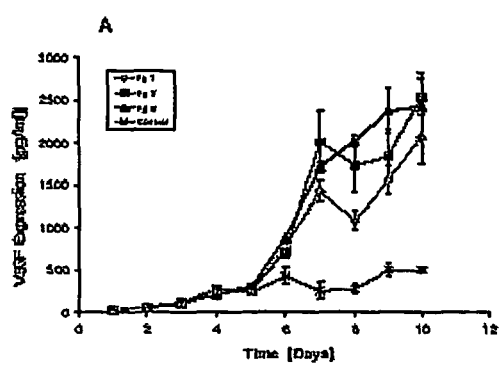 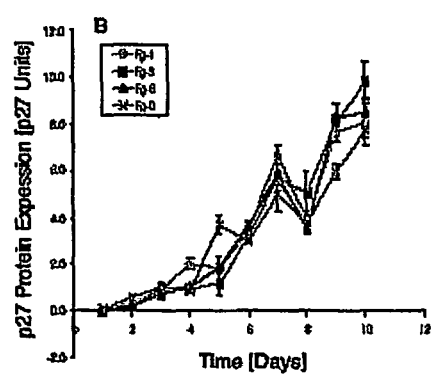
Figure 5A          Figure 5B

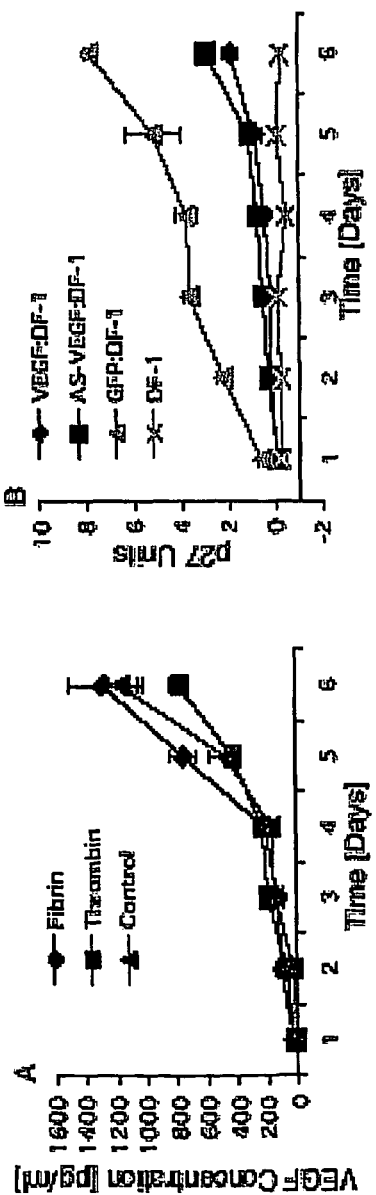
Figure 6A
Figure 6B
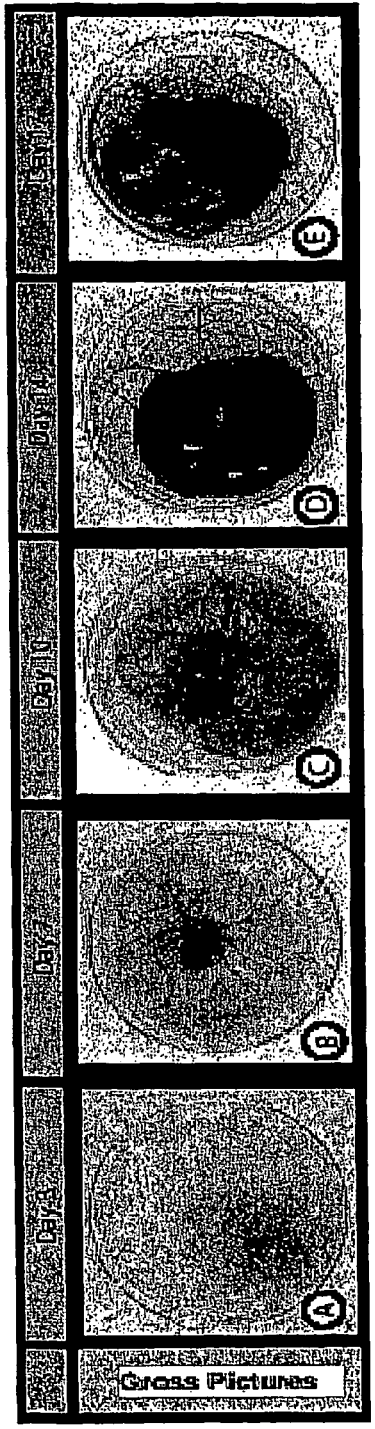
Figure 7A    Figure 7B    Figure 7C    Figure 7D    Figure 7E

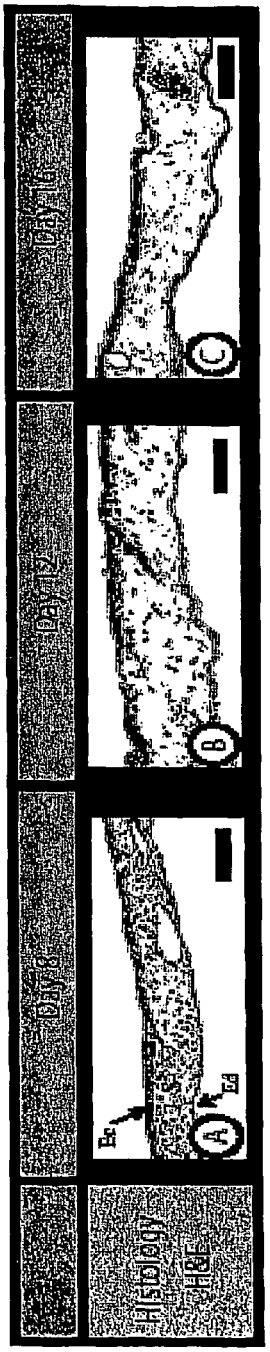
Figure 8A  Figure 8B  Figure 8C
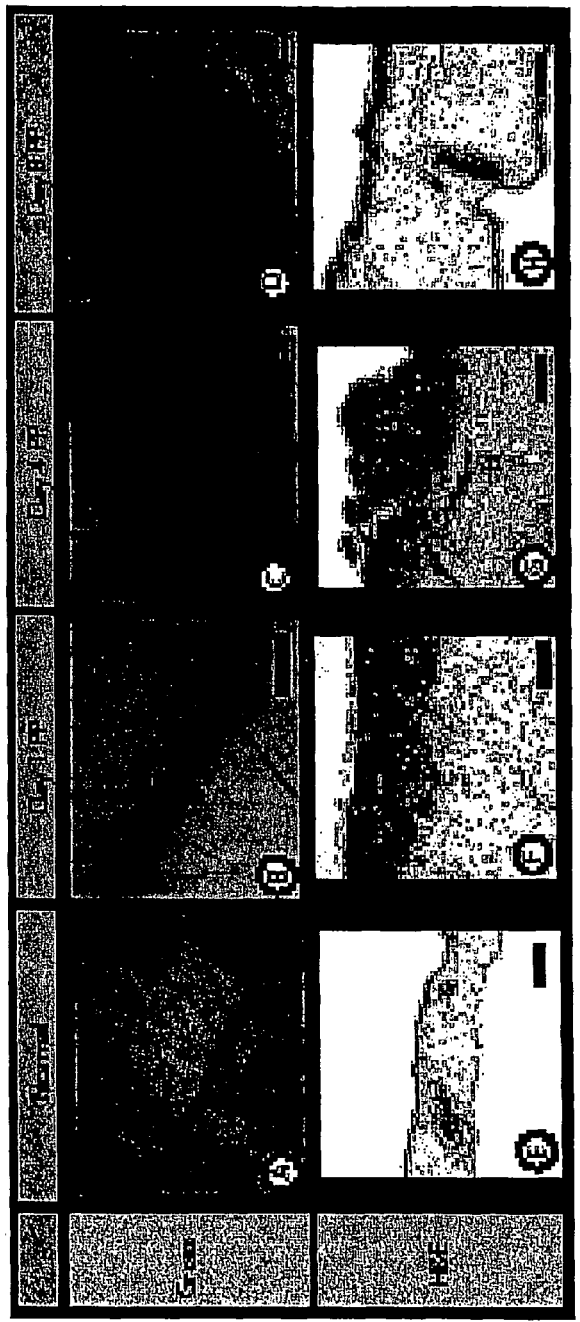
Figure 9A  Figure 9B  Figure 9C  Figure 9D
Figure 9E  Figure 9F  Figure 9G  Figure 9H

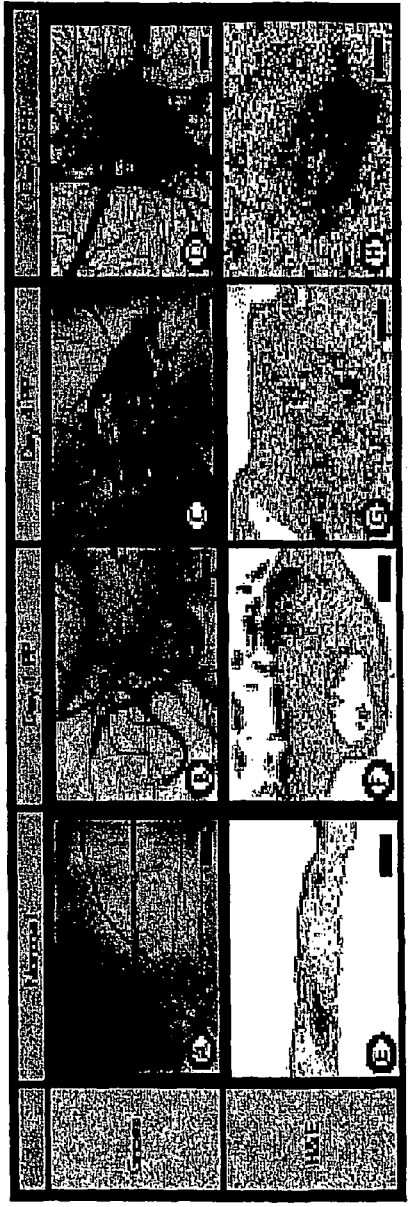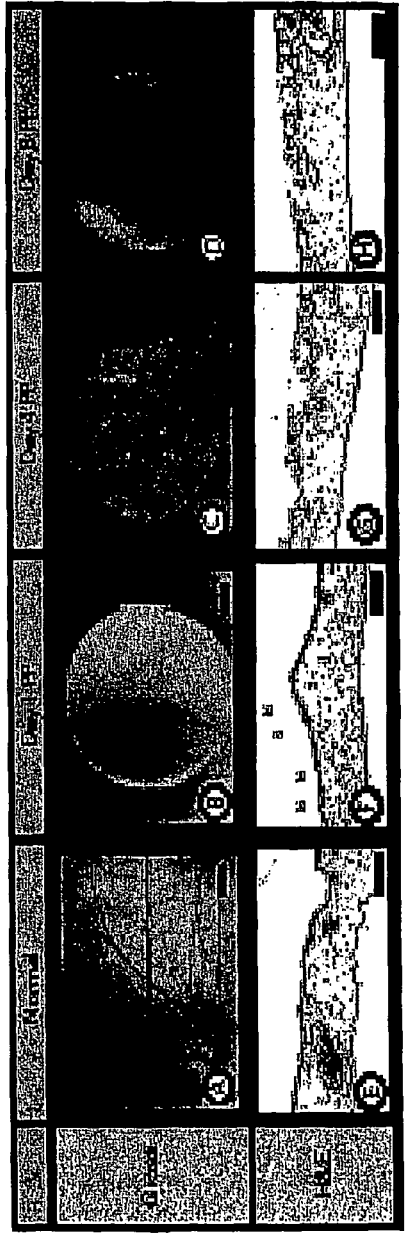

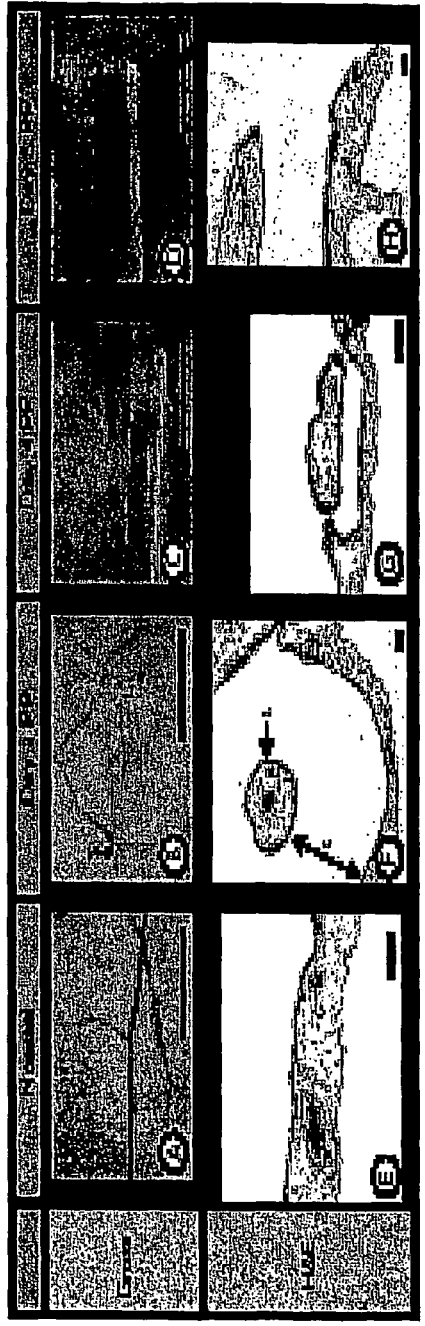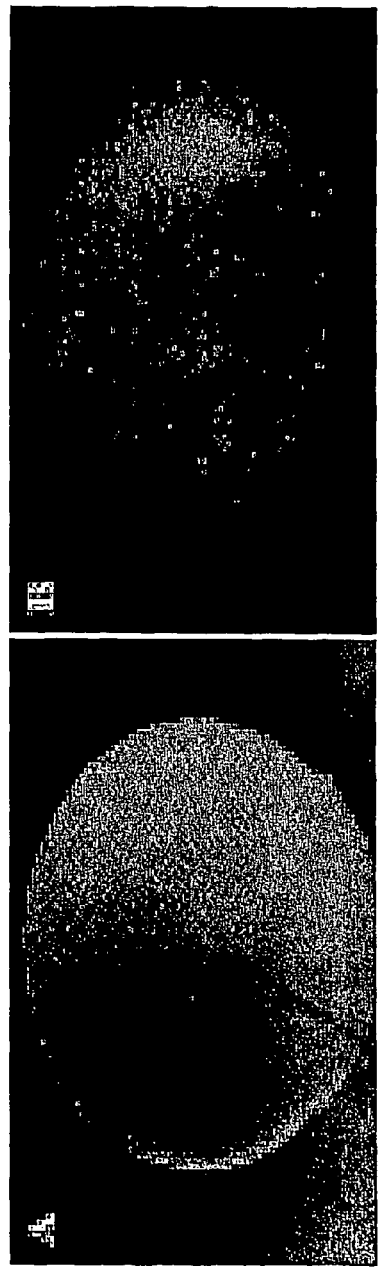

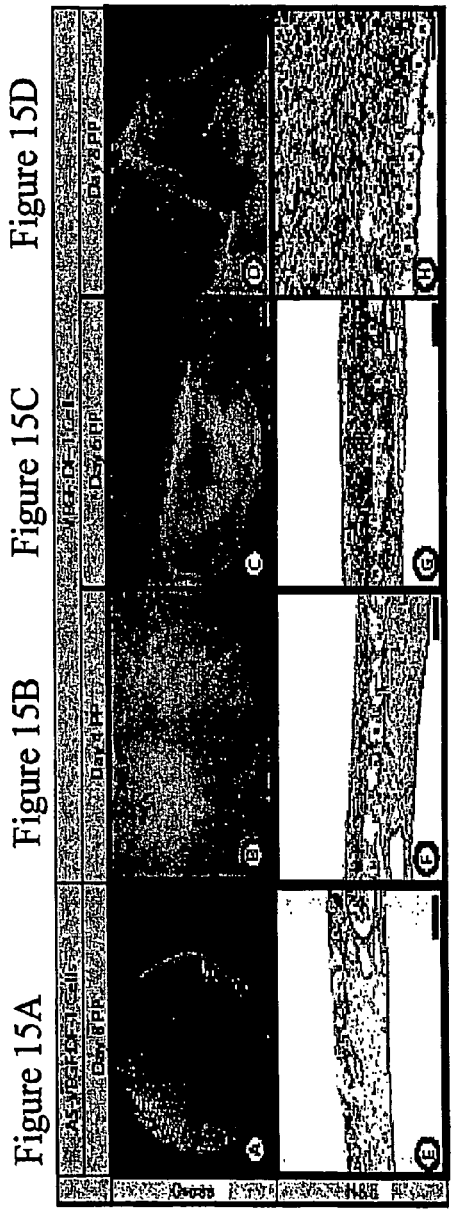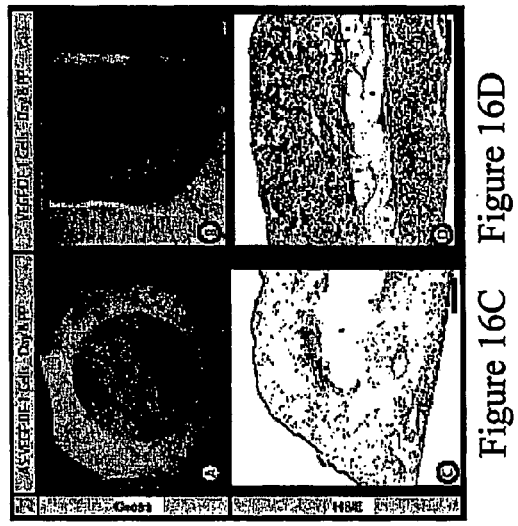

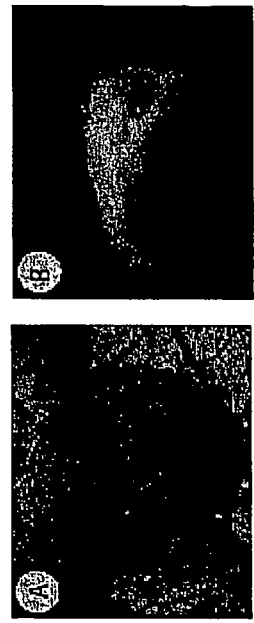
Figure 17A
Figure 17B
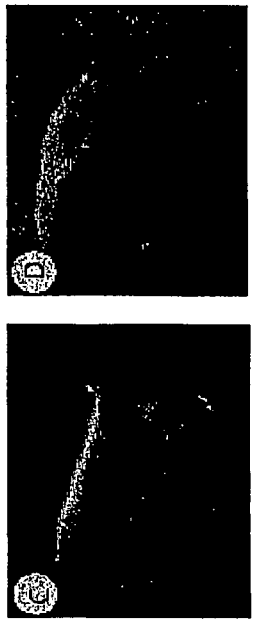
Figure 17C
Figure 17D
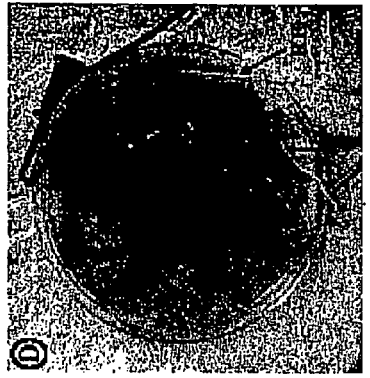
Figure 18C
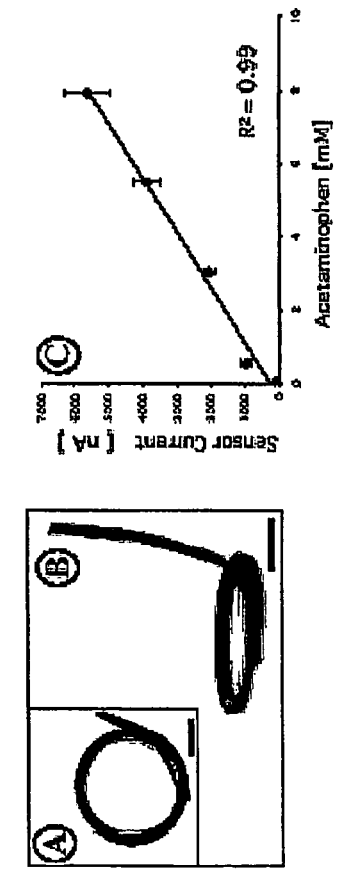
Figure 18D
Figures 18A-18B

```
1 caagcgcgca agagagcggg ctgcctcgca gtccgagccg gagagaggga gcgcgacgcg 61 cgcggccccg gacgccctcc gaaaccatga actttctgct
ctcttgggtg cactggaccc 121 tggctttact gctgtacctc caccatgcca agtggtccca ggctgcaccc acgacagaag 181 gagagcagaa gtcccatgaa
gtatcaagt tcatggacgt ctaccagcga agctactgcc 241 gtccaattga gacctggtg gacatcttcc aggagtaccc cgacgagata gagtacatct 301
tcaagccgtc ctgtgtgccg ctgatgcgct gtgcaggctg ctgtaacgat gaagccctgg 361 agtgcgtgcc cacgtcagag agcaacatca ccatgcagat
catgcggatc aaacctcacc 421 aaagccagca catagagaga atgagcttcc tacagcacag cagatgtgaa 481 agaaagacag
aacaaagcca gaaaatcact gtgagccttg ttcagagcgg agaaagcatt 541 tgtttgtcca agatccgcag acgtgtaaat gttcctgcaa aaacacagac
tcgcgttgca 601 aggcgaggca gcttgagtta aacgaactc ctgcagatg tgacaagcca aggcggtgag 661 cgaggctggc aggaaggagc
ctcctcaggg tttcgggaac cagacctctc accggaaaga 721 ccgattaacc atgtcaccac catgccatca tcgtcaccgt tgacagaaca gtccttaatc 781
cagaaagcct gatatgaagg aagaggagat ccttcgagga gcacttggg tccggaggc gagactccgg cagacgcatt cccggccagg tgaccaagca
cgtgcctcgt gggactggat 901 tcgccatttt cttatatctg ctgctaaatc gccaagcccg gaagattagg gttgtttctg 961 ggattcctgt agagctcgtg
```

FIGURE 22

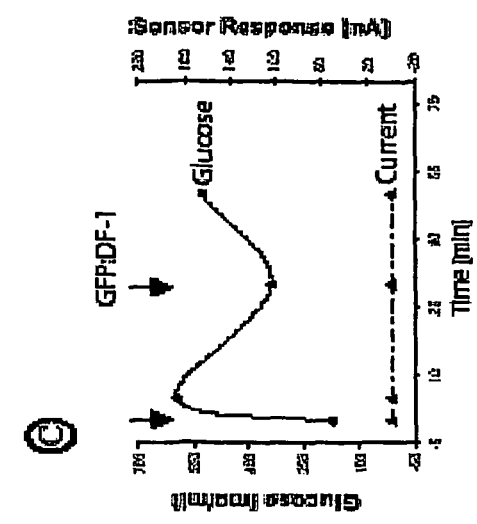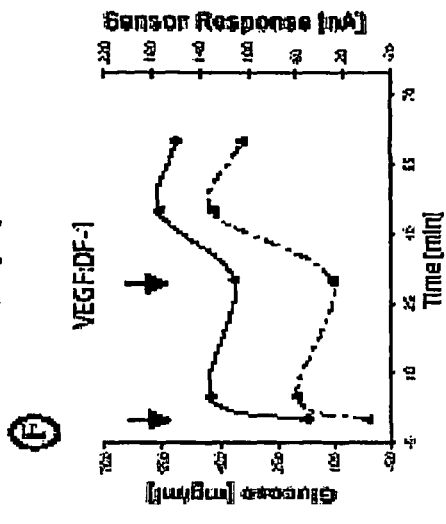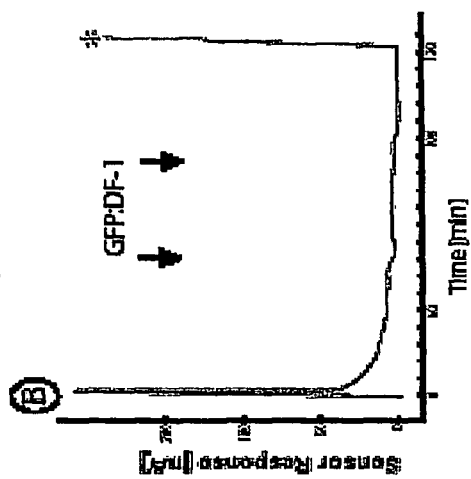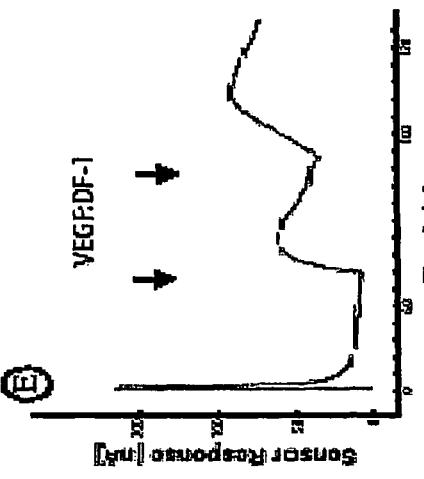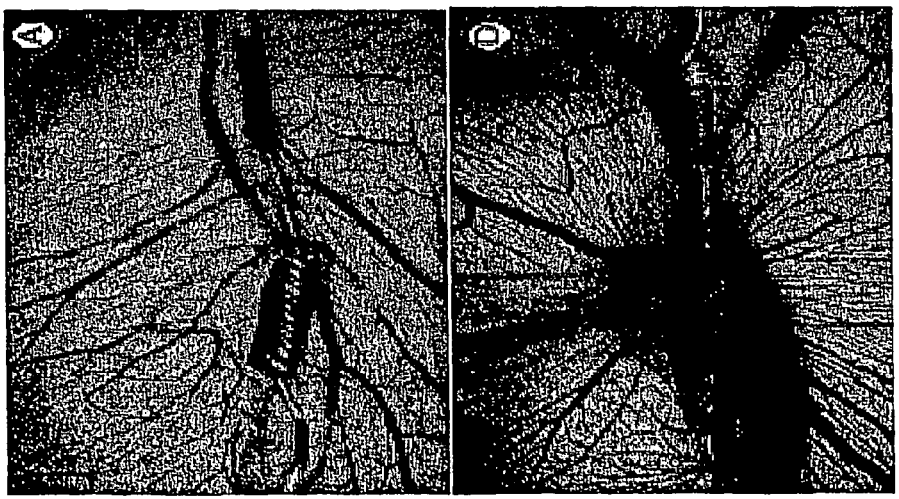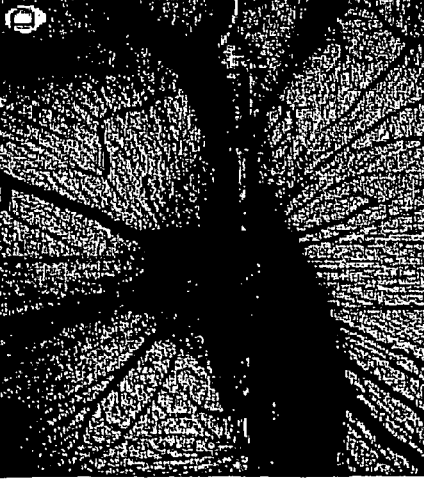
Figure 27A Figure 27B Figure 27C
Figure 27D Figure 27E Figure 27F

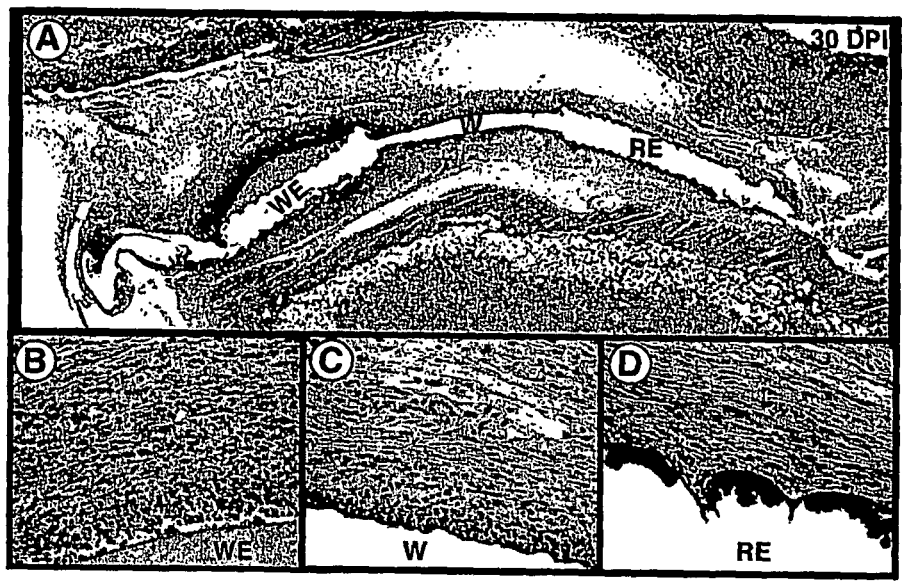
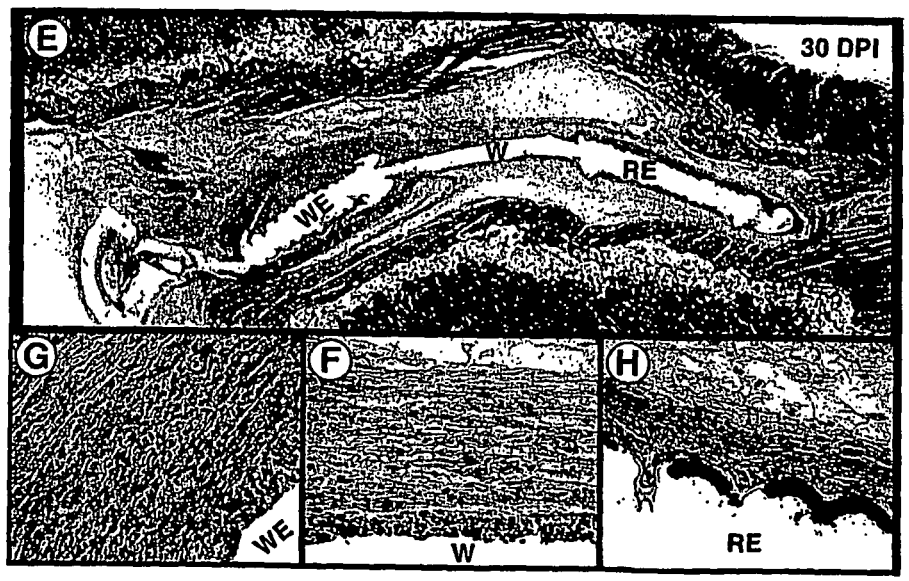
Figures 37A – 37H

ARTIFICIAL TISSUE SYSTEMS AND USES THEREOF

CROSS REFERENCE TO RELATED APPLICATIONS

This application claims the benefit of U.S. Provisional Application No. 60/518,412, filed Nov. 7, 2003, the content of which is incorporated by reference in their entirety.

STATEMENT WITH REGARD TO FEDERAL SPONSORED RESEARCH & DEVELOPMENT

This invention was made with Government support under Grants awarded by the National Institutes of Health (1RO1RR14171) the United States Department of Defense W81XWH-04-1-0002 and W81XWH-04-1-0313. The Government has certain rights in the invention.

FIELD OF THE INVENTION

The invention relates generally to the field of medical implants. In particular, this invention relates to apparatus and methods for better controlling the natural and artificial microenvironments surrounding implanted devices and sensors in biological systems.

BACKGROUND OF THE INVENTION

Implantable materials and devices, such as drug delivery systems, pacemakers, artificial joints, and organs play an important role in health care today. In addition to these devices, implantable monitoring devices implantable sensors have great potential for improving both the quality of care and quality of life of patients and animals. Potentially these sensors can measure a wide variety of analytes in the blood and tissue, which would be critical in the early diagnosis and treatment of disease.

Unfortunately the development of these implantable sensors has been hampered by the inability of currently designed implantable sensors to overcome their loss of function and short lifespan in vivo. Frequently this loss of function is a result of the acute and chronic tissue reactions to the implanted sensors. These tissue reactions are a result of various factors including 1) tissue injury and inflammation as a result of tissue trauma from the surgical implantation of the device, 2) immune and non-immune inflammation at the implantation site as a result of "foreign body" reactions to the device, 3) the release to tissue of toxic factors from the function of the device and or the chemical breakdown of the device and its coating. Ultimately, these chronic inflammatory reactions at sites of sensor implantation result in tissue destruction and fibrosis and complete loss of sensor function in vivo.

Conventionally, efforts to extend the in vivo lifespan of implantable glucose sensors have focused on the uses of various sensor coatings, in an effort to hide or stealth the sensor from detection and the resulting tissue reactions. Unfortunately these approaches have not been successful, and the use of various coatings has seen limited success because of the body innate and acquired host defense systems (immunity) that can detect minute differences between normal tissue elements and foreign materials such as sensor coatings.

Alternative conventional efforts to incorporate bioactive drugs and peptides and proteins into the coatings or sensor associated drug delivery systems have seen some success. However, in the case of sensor coatings it has been found that 1) frequently only "analyte permeable coatings" can be used as sensor coatings, thus limiting the type of coating available for implantable sensors; 2) binding of sufficient quantities of bioactive agents such as peptides and proteins, can be difficult and often they do not remain active after being bound to the sensor coating; 3) the intense tissue reactions (proteins and cells) frequently "mask" or degrade the bioactive agents on the coatings and limit their effectiveness 4) because of the limited quantities of bioactive agents that can be incorporated into sensor coatings, the coating and therefore the sensor have a limited lifespan in vivo and must be replaced frequently. Additionally the device and its byproducts can also damage both the tissue and the sensor and its coatings. For example, implantable sensors generally function based on the use of glucose oxidase which is specific for glucose. The enzyme needs to be immobilized on the platinum wire by using a carrier protein such as albumin and toxic crosslinking agent such as glutaraldehyde. Additionally, the glucose oxidase used in the sensor continuously breaks down glucose into gluconic acid and hydrogen peroxide, both of which are tissue toxic as well as potentially "sensor toxic". The hydrogen peroxide is further broken down in reactive oxygen radicals, which are also toxic.

In the case of traditional drug delivery systems such as micro beads, they frequently do not incorporate (load) and or release bioactive agents in quantities and for durations that are useful for implantable sensors. Since the drug delivery system used with implantable sensors are usually located near the sensor, "foreign body" tissue reactions to the drug delivery system often have negative "bystander" effects on the sensor and its function. For example, the breakdown of the drug delivery systems such as micro beads result in the release of tissue toxic and sensor toxic byproducts that hinder sensor function in vivo. Ultimately the combination of inflammation, fibrosis and loss of blood vessels also decrease tissue levels of both glucose and oxygen, both essential to glucose sensor function in vivo, with a resulting loss of sensor function and lifespan in vivo. Clearly in the future, new approaches, methods and devices are needed to extend the function and lifespan of implantable sensors such as the glucose sensors used in conjunction with, for example, the disease condition known as diabetes.

Diabetes is a chronic disease that afflicts over 18 million people in United States, with an annual cost of $132 billion in direct and indirect expenditures in the United States. Diabetes is a leading contributor to many other diseases, including heart disease, stroke, blindness, kidney failure, and peripheral neuropathy. The key factor in preventing these devastating complications of diabetes is the close monitoring of blood glucose levels. Currently, repeated "finger sticks" to obtain capillary blood samples is the major approach to monitoring blood glucose levels. Unfortunately, because of the pain and inconvenience of this procedure associated with "finger sticking" the patient compliance is often poor. However, even with good patient compliance with regular blood glucose testing, it appears that blood glucose swings often stay undetected. For example, initial continuous glucose monitoring has shown that glucose concentrations are only within a target range of 4-10 mmol/l for about 35 percent of the time. Clearly, there is a critical need for a method that would allow continuous blood glucose monitoring in vivo.

Although implantable glucose sensors have been in existence for over 30 years, and in vitro studies have demonstrated that they can function for weeks to months, glucose sensor function in vivo has seen little success. Previous in vivo studies have indicated that implantable glucose sensors lose function within hours to days after implantation.

It is generally accepted that the loss of sensor function in vivo is associated with sensor induced tissue injury, inflammation and fibrosis with associated blood vessel regression. Presently there has been little progress in the developments for the reason described above. In fact currently available glucose sensors display rapid loss in sensor function within 1-3 days post sensor implantation, and even these sensors require frequent reference "finger sticks" to determine blood glucose levels to utilize to recalibrate the implanted sensor. Clearly a new approach and devices are needed for enhancing the in vivo function and lifespan of implanted sensors such as the glucose sensor.

SUMMARY OF THE INVENTION

Briefly stated, the present invention in a preferred form includes an apparatus and a method for controlling the natural and artificial microenvironments surrounding an implanted device using an artificial tissue system (ATS). The ATS, among other things, induce better integration, improved function, and an extended lifespan of the devices at the site of implantation. The ATS includes cells, such as naturally occurring, engineered, and/or artificial cells and matrices such as a natural, engineered, artificial and/or hybrid matrix. Tissue response modifiers (TRM) and/or cell response modifiers (CRM) as also preferentially included. The specific composition of the ATS is based on the nature of the tissue in which also are preferred included the ATS-device combination is implanted and the nature of the implanted device, as well as the required function and lifespan of the implanted device. Additionally, the ATS, as well as ATS-device combinations can be utilized in vitro to aid in the design of improved artificial tissue systems, devices and ATS-device combinations for in vivo uses.

The invention includes an artificial tissue system, comprising (a) a matrix configured for biological contact with an implantable device, and (b) a plurality of cells supported by said matrix, said cells promoting a biological interaction between said implantable device and a biological system.

The invention also includes an implant system comprising an implantable device, a matrix in biological contact with said implantable device, and a plurality of cells supported by said matrix, said cells promoting a biological interaction between said implantable device and a biological system.

The invention includes an artificial implant system in biological contact with a biological system comprising a cellular component, said cellular component includes at least one cellular community which induces a biological response in the biological system. Also included is a matrix material, said matrix material being associated with a portion of the cellular community; and an implant device having a biological interface wherein said biological interface is associated with the matrix material and the biological system.

The invention further includes a method of implanting a device in a biological system, comprising the steps of: obtaining said device, obtaining a matrix, placing said device in biological contact with said matrix, inserting cells into said matrix, said cells being capable of promoting a biological interaction between said implantable device and said biological system, and implanting said matrix into said biological system.

BRIEF DESCRIPTION OF THE DRAWINGS

Other objects and advantages of the invention will be evident to one of ordinary skill in the art from the following detailed description with reference to the accompanying drawings, in which:

FIGS. 2A-2E show the morphology of various control and Rous Sarcoma virus infected DF-1 cells consistent with the present invention;

FIGS. 3A and 3B respectively show the in vitro expression of p27 and VEGF in both control and RCAS infected DF-1 cells consistent with the present invention;

FIG. 4 shows GFP:DF-1 cells associated with a fibrin matrix material consistent with the present invention;

FIGS. 5A and 5B respectively show in vitro VEGF protein expression and Avian Leucosis p27 expression associated with cells in a fibrin matrix material at various fibrinogen concentrations consistent with the present invention;

FIGS. 6A and 6B show the impact of thrombin on VEGF: DF-1 cells and control cells consistent with the present invention;

FIGS. 7A-7E respectively show the development of the chorioallantoic membrane in the ex ova model of the chick embryo at days 3, 7, 10, 14, and 17;

FIGS. 8A-8C respectively show the histology of portions of normal chorioallantoic membrane at days 8, 12, and 16;

FIGS. 9A-9D respectively show gross views of the inflammatory responses in an ex ova chorioallantoic membrane model of LPS/india ink induced reactions at days 0, 1, 4, and 8 consistent with the present invention;

FIGS. 9E-9H respectively show histologic views of the inflammatory responses in an ex ova chorioallantoic membrane model of LPS/india ink induced reactions at days 0, 1, 4, and 8 consistent with the present invention;

FIGS. 10A-10D respectively show gross views of the inflammatory responses in an ex ova chorioallantoic membrane model of cotton thread induced reactions at days 0, 1, 4, and 8 consistent with the present invention;

FIGS. 10E-10H respectively show histologic views of the inflammatory responses in an ex ova chorioallantoic membrane model of cotton thread induced reactions at days 0, 1, 4, and 8 consistent with the present invention;

FIGS. 11A-11D respectively show gross views of the tissue response in a chorioallantoic membrane associated with nylon at days 0, 1, 4, and 8 consistent with the present invention;

FIGS. 11E-11H respectively show histologic views of the tissue response in a chorioallantoic membrane associated with nylon at days 0, 1, 4, and 8 consistent with the present invention;

FIGS. 12A-12D respectively show gross views of the tissue response in a chorioallantoic membrane associated with silastic tubing at days 0, 1, 4, and 8 consistent with the present invention;

FIGS. 12E-12H respectively show histologic views of the tissue response in a chorioallantoic membrane associated with silastic tubing at days 0, 1, 4, and 8 consistent with the present invention;

FIGS. 13A and 13B show the gross appearance of GFP: DF-1 cells grown on nylon disks and placed on a chorioallantoic membrane consistent with the present invention;

FIGS. 15A-15D respectively show gross views of neovascularization induced in the ex ova chorioallantoic membrane model using VEGF:DF-1 cells grown on nylon disks consistent with the present invention;

FIGS. 15E-15H respectively show histologic views of neovascularization induced in an ex ova chorioallantoic membrane model using VEGF:DF-1 cells grown on nylon disks consistent with the present invention;

FIGS. 16A and 16B respectively show gross views of neovascularization induced in an ex ova chorioallantoic membrane model using AS-VEGF:DF-1 and VEGF:DF-1 cells added to nylon rings consistent with the present invention;

FIGS. 16C and 16D respectively show histologic views of neovascularization induced in an ex ova chorioallantoic membrane model using AS-VEGF:DF-1 and VEGF:DF-1 cells added to nylon rings consistent with the present invention;

FIGS. 17A-17D show the gross morphologic appearance of neovascularization induced in the ex ova chorioallantoic membrane model using VEGF:DF-1 cells in a fibrin matrix material consistent with the present invention;

FIGS. 18A and 18B, respectively, are a top view of a sensor and a side view of a sensor consistent with the present invention;

FIG. 18C is graph showing the relationship between a sensor output and chemical concentration consistent with the present invention;

FIG. 18D shows a sensor as shown in FIGS. 18A and 18B associated with an in vitro experimental set-up consistent with the present invention;

FIG. 22 is SEQ. ID NO 1 and shows a nucleic acid sequence associated with mouse vascular endothelial growth factor M95200;

FIGS. 27A and 27D show an implanted glucose sensor in an ex ova model consistent with the present invention;

FIGS. 27B and 27C show glucose sensor response associated with an ATS with GFP:DF-1 consistent with the present invention;

FIGS. 27E and 27F show glucose sensor response associated with an ATS with VEGF:DF-1 consistent with the present invention;

FIGS. 35B, D, F, and H respectively show histologic views of IRC mouse tissue, stained with trichrome, associated with a working electrode of an implanted glucose sensor at 1 dpi, 3 dpi, 7 dpi, and 14 dpi consistent with the present invention;

FIGS. 35I, K, M, and O respectively show histologic views of IRC mouse tissue, stained with HE, associated with a reference electrode of an implanted glucose sensor at 1 dpi, 3 dpi, 7 dpi, and 14 dpi consistent with the present invention;

FIGS. 35J, L, N, and P respectively show histologic views of IRC mouse tissue, stained with trichrome, associated with a reference electrode of an implanted glucose sensor at 1 dpi, 3 dpi, 7 dpi, and 14 dpi consistent with the present invention;

FIGS. 37A-37H show histologic views of tissue at 30 dpi associated with implanted sensors having a working electrode, an intermediate wire, and a reference electrode consistent with the present invention;

DETAILED DESCRIPTION OF THE INVENTION

Figure 1:
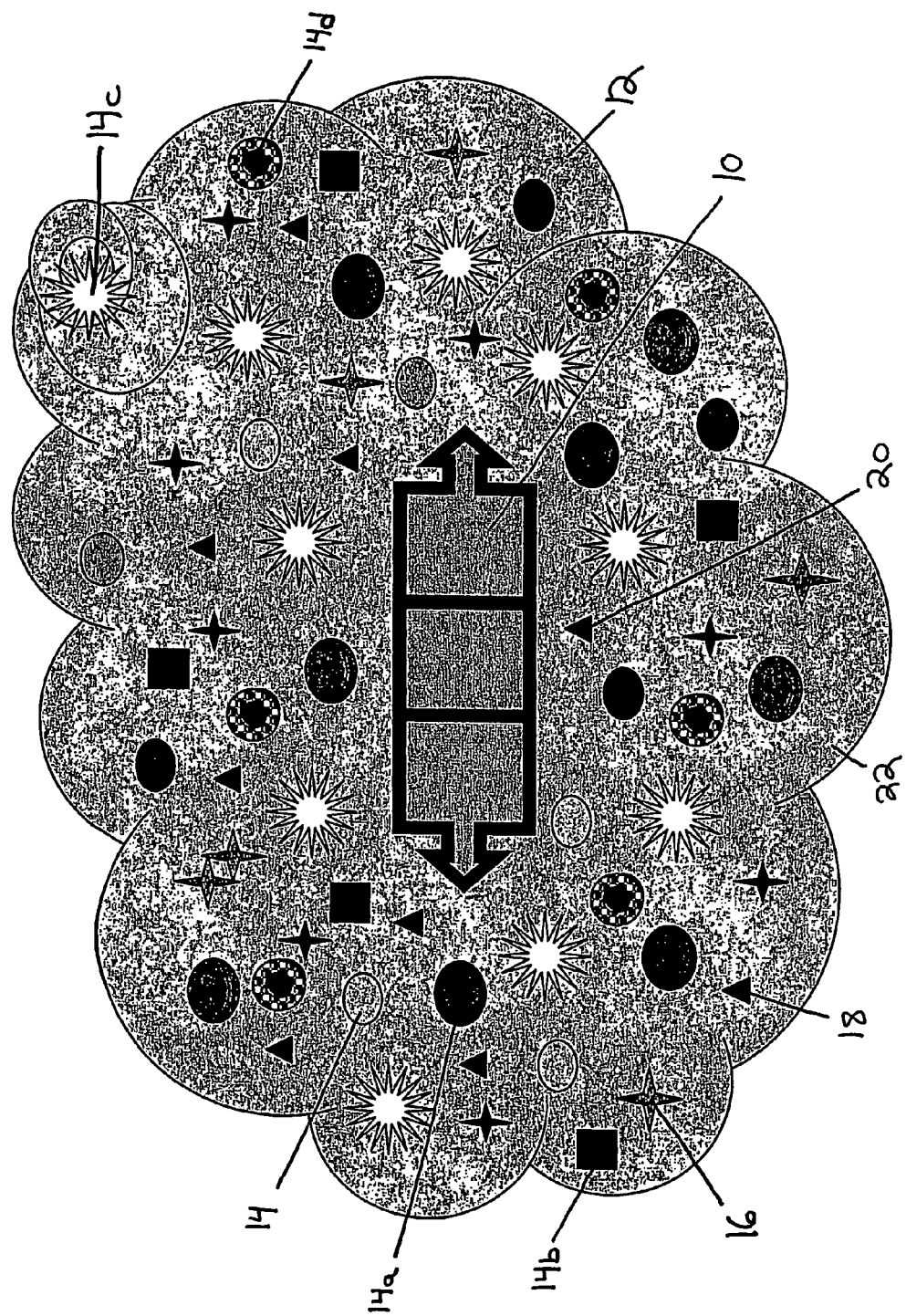
FIG. 1 shows an artificial tissue system with various possible constituents consistent with the present invention.

The general meaning of the following terms as used in the present application, unless specifically modified, are: "Normal Cells": biological cells derived from living organisms, and/or tissues, which retain a normal genotype and phenotype, usually obtained directly from tissue or from primary culture. "Mutant Cells": biological cells with spontaneously altered genotype and phenotype, such as cancer cells, cell derived from naturally occurring genetically deficient organisms, usually obtained in secondary culture and or continuous cell lines. "Engineered Cells": genetically or chemically modified biological cells (usual original source is Normal or Mutant cells). "Transgenic Cells": biological cells derived from transgenic animals, in which the cells have genetically induced alterations of genotype and or phenotype. "Gene Transfer Cells": biological cells that have altered phenotype resulting in alteration of cell structure and or function. This includes knockouts, knockdowns, "over-expressors" etc. "Chemically Modified Cells": biological cells in which membrane, cytoplasm structural or enucleolar elements of the cell are altered permanently or for extended periods, thus altering cell structure and or function. "Artificial Cells": biological cells lacking the ability to replicate but capable of sensing and responding to their microenvironment. For example enucleated cells, or cells lacking a nucleus (e.g. red blood cells), in which genetic elements such as DNA, RNA, viral vectors, nanodevices or nanomaterials can be incorporated for in vivo uses. Hybrid Cells: biological cells that are the result of cells fusion, and or combinations of engineered and or artificial cells. "Matrix material": complex heterogeneous networks of insoluble macromolecules such as glycoproteins, carbohydrates, structural proteins (e.g. collagen), as well as bound proteins and factors. These matrices contain specific binding sites for cells, factors (e.g. cytokines and growth factors) and proteins, which directly control cell adhesion and function in vivo and in vitro. "Biological Matrices": matrices obtained from organisms, tissues, or cell. Examples of biological matrices include interstitial matrices, basement membrane, fibrin clots. Interstitial matrices are generally composed of fibrillar and nonfibrillar collagen, elastin, fibronectin proteoglycans, hyuronate, as well as other components. Basement membranes are composed of nonfibrillar collagen (usually IV), laminin, heparin sulfate, proteoglycan, and other glycoproteins. Fibrin clots are complex networks of plasma proteins including fibrin(ogen), fibronectin, glycoproteins, heparin, thrombin collagen, as well as other plasma proteins cross-linked to the fibrin clots via Factor XIII. Additionally, fibrin clots have extensive binding sites for various factors and cells including leukocytes, fibroblasts and endothelial cells. "Engineered Matrices": genetically and or chemically modified biological matrices. "Hybrid matrices": combinations of biological, engineered and or artificial matrices. In addition, the meaning of various abbreviations as used within the present application, unless specifically modified, include ES, embryonic stem cell; MSC, mesenchymal stem cell; MAPC, multipotent adult progenitor cell; HSC, hematopoietic stem cell; NSC, neural stem cell; NPC, neural progenitor cell; MDSC, muscle-derived stem cell; ECM, extracellular matrix; EGF, epidermal growth factor; LIF, leukemia inhibitory factor; SCF, stem cell factor; HGF, hepatocyte growth factor; PDGF, platelet-derived growth factor; VEGF, vascular endothelial growth factor; BMP, bone morphogenetic protein; BDNF, brain-derived neurotrophic factor; NT, neurotrophin; CNTF, ciliary neurotrophic factor; bFGF, basic fibroblast growth factor; TGF-$\beta$, transforming growth factor-beta; IL, interleukin; G-CSF, granulocyte-colony stimulating factor; GM-CSF, granulocyte-macrophage colony stimulating factor; IGF, insulin-like growth factor; RA, retinoic acid; and FBS, fetal bovine serum.

An artificial tissue system implant, in one embodiment of the invention, as shown in FIG. 1, includes an implant device, for example, a sensor 10. The sensor 10 is surrounded by an artificial tissue system 12. The artificial tissue system (ATS) 12 includes cells. For example, the cell may be biological cells 14, genetically engineered cells 14a, artificial cells 14b, stem cells 14c and/or support cells 14d. The support cells 14d generally are included with other cells and serve to provide nutrients, factors, physical surfaces, or other required or desirable products to the cells they support. The ATS may also include genetic elements 16, cell response modifiers (CRM) 18, and/or tissue response modifiers (TRM) 20. The ATS 12 further includes a matrix material 22. The matrix material 22 may be a natural and/or synthetic material. For example, the matrix material 22 may include biological matrices such as naturally occurring matrices that occur in viable organisms (in vivo) and tissues including ex vivo tissues, as well as in association with cells maintained in vitro, or combinations thereof. One characteristic of the matrix material 22 is the ability to provide a three dimensional structure to the ATS 12. This three dimensional structure provides a volume of space that allows for biological contact wherein various components of the ATS 12, sensor 10, and surrounding tissues can biologically associate with one another. For example, the matrix material may provide the necessary framework in which various cells can be secured as well as providing for the movement of nutrients, chemicals, and other bioactive agents to, from, and/or between cells, tissues, and/or an implant device, such as, the sensor 10. In addition, the matrix material 22 is in biological contact with portions of the implant device and the surrounding biological system, if present. It should be understood that the biological contact includes, among other things, chemical, liquid, gas, and/or mechanical contact. For example, cellular tissue of the biological system may intrude, or otherwise extend physically into, the volume of space occupied by the matrix material. This cellular tissue may also be in physical, chemical, and/or fluid contact with the cells, portions of the implant device, such as the sensor 10, genetic elements 16, CRM 18, and/or TRM 20. The genetic elements 16 include, for example, agent(s) that directly cause the temporary or permanent change of the genetic composition or expression of a cell or tissue, or indirectly cause the temporary or permanent change of the genetic composition or expression of a cell or tissue. For example, single or double strand DNA, single or double strand RNA, plasmids, viral vectors, and/or DNA or RNA viral vectors. In addition, it should be understood that the ATS may be formed into, for example, any biologically relevant shape, for example, a tube, sponge, sphere, strand, coiled strand, capillary network, film, fiber, mesh, and/or sheet.

In one embodiment of the invention, the cells include eukaryotic cells; prokaryotic cells; vertebrates cells; invertebrates cells; normal cells; cancer cells; mutant cells; engineered cells, such as genetically altered cells, chemically altered cells, transgenic cells, hybrid cells (hybridomas); artificial cells; and stem cells, such as embryonic stem cells, adult stem cells, stem cell lines, engineered stem cells. The cells may be classified as categories of functional cells, for example, inflammatory cells, immune cells, tissue cells, cells which control wound healing, cells which control fibrosis, cells which control tissue regeneration, regulatory cells, cytokine producing cells, growth factor producing cells, matrix producing cells, vascular cells, connective tissue cells, bone producing cells and bone, blood cells. The cells may also be classified as types of cells, for example, endothelial cells, fibroblasts, epithelial cells, muscle cells, fat cells, lymphocytes, macrophages, mast cells, polymorphonuclear leukocytes, red blood cells, neurologic cells, osteoblasts, osteoclasts, nerve cells, fat cells, brain cells. Other categories of cells may be used and include, but are not limited to, autologous cells, heterologous cells, allogenic cells, xenogenic cells, autologous cells, (relative to the host), heterologous cells (relative to the host), allogenic cells (relative to the host tissue), xenogenic cells (relative to the host tissue). It should be understood that the cells may be used in combination with one another such that a cellular component is formed. The cellular component may include one or more cellular communities wherein the communities interact on, for example, symbiotic, commensal, saprophytic, inhibitory and/or other biologically relevant association. For example, engineered and non-engineered cells may be used in combination to provide advantageous biologic contact with one another and with a biologic system with which they are associated, for example a living mammal biologic system.

In one embodiment of the invention, cell of different categories and/or types may be combined in the matrix material 22. For example, functional cells may be used which regulate the function of other cells within the matrix material 22. This may include cells that produce cytokines and growth factors; cells that regulate the function of the cells within the host tissue; cells that include matrix producing cells within the host tissue; cells that produce cytokines and growth factors which control cells in the host tissues; cells that controls inflammation within the ATS; cells that control wound healing within the ATS; cells that control fibrosis within the ATS; cells that control neovascularization within the ATS; cells that control cell proliferation within the ATS; cells that control immune responses within the ATS; cells that include cells that control cell death within the ATS; cells that includes cells that control inflammation within the tissues; cells that control wound healing within the tissues; cells that control fibrosis within the tissues; cells that control neovascularization within the tissues; cells that control cell proliferation within the tissues; cells that control immune responses within the tissues; cells that control cell death within the tissues; cells that produces cytokines; cells that produce growth factors; cells that control vessel formation and regression; cells that produce genetically altered proteins and peptides; and cells that overproduce proteins and/or peptides.

Sources of biological cells include cells directly isolated from in vivo sources; cells obtained from embryonic tissues, neonatal tissues, juvenile or adult tissues; cells obtained from in vitro sources; cells obtained from primary cell culture sources; cells obtained from secondary cell culture sources; and cells obtained from continuous cell lines.

In one embodiment of the invention the CRM 18 and/or TRM 20 are differentiated based on their biologic effect. For example, "cell response modifiers" (CRM) 18, as used herein, include agents that control the structure and or function of cells in vitro and or in vivo, whereas, "tissue response modifiers" (TRM) 20 as used herein, include agents that control the structure and or function of tissues in vivo and or ex vivo. The CRM 18 may include cells genetically engineered and non-genetically engineered: biological cells, synthetic cells, regulatory cells, tissue support cells, mutant cells, artificial cells, genetically altered cells, chemically altered cells, and/or stem cells. The CRM 18 may control cellular proliferation; cell injury; cell death; cell metabolism; cell protein synthesis; cell gene expression; and/or agents that control the structure and/or function of cells derived from any in vitro or in vivo source.

In one embodiment of the invention, the categories or types of cells whose structure and or function is controlled by CRM 18, include cells derived from embryonic, neonatal, juvenile and or adult cells. In addition, cells that may be controlled by CRM 18 include biological cells, eukaryotic cells, prokaryotic cells, vertebrates cells, invertebrates cells, normal cells, cancer cells, mutant cells, engineered cells, artificial cells, stem cells, and/or hybrid cells. In addition, cells controlled by CRM 18, include, for example, endothelial cells, fibroblasts, epithelial cells, muscle cells, fat cells, lymphocytes, macrophages, mast cells, polymorphonuclear leukocytes, red blood cells, neurologic cells, osteoblasts, osteoclasts, nerve, fat cells, brain cells, bone cells, tissue derived stem cells, blood derived stem cells, bone derived stem cells.

In one embodiment of the invention the CRM 18, include agents that, for example, control cell homeostasis by controlling cell functions such as cell activation, cell proliferation, cell metabolism, cell death (including apoptosis), cell differentiation and maturation, cell size, cell composition.

In one embodiment of the invention, the TRM 20 includes, for example, agent(s) that control tissue growth; tissue differentiation; tissue injury; innate immune responses; acquired immune responses; humoral immune responses; cell mediated immune responses; inflammation; acute inflammation; chronic inflammation; wound healing; regeneration; tissue repair; neovascularization; bone destruction; bone injury, repair and or regeneration; connective tissue destructions; controls connective tissue injury, repair and regeneration; fat tissue injury, repair and or regeneration; neurologic tissue injury, repair and or regeneration; and/or responses using TRM 20. The TRM 20 may include: cell to cell protein transporter molecules; antibodies; proteins, modified proteins and/or recombinant protein; chemicals; drugs; genetic elements; recombinant DNA; RNAs, including siRNA; altered RNAs; genetically altered RNAs; chemically altered RNAs; DNA; altered DNAs; carbohydrates; lipids and fatty acids; radiation energy; magnetic energy; viruses; single or double strained DNA; and/or single or double strained RNA.

The TRM 20 may be used in combination, for example, the TRM 20 may include: TRM that controls tissue injury and a second TRM that controls inflammation; TRM that controls inflammation and a second TRM that controls fibrosis; TRM that controls inflammation and a second TRM that controls neovascularization; TRM that controls inflammation and a second TRM that controls tissue regeneration; TRM that controls cell injury and a second TRM that controls inflammation; TRM that controls cell death and a second TRM that controls inflammation; TRM that controls inflammation and a second TRM that controls fibrosis; TRM that controls inflammation and a second TRM that controls neovascularization; TRM that controls fibrosis and a second TRM that controls neovascularization; and/or TRM that controls inflammation and a second TRM that controls tissue regeneration.

The TRM 20 may, for example, in one embodiment of the invention include the agents 2-(3-benzophenyl)propionic acid, 9-alpha-fluoro-16-alpha-methylprednisolone, methyl prednisone, fluoroxyprednisolone, 17-hydroxycorticosterone, cyclosporin, (+)-6-methoxy-.alpha.-methyl-2-naphthalene acetic acid, 4-isobutyl-.alpha.-methylphenyl acetic acid, Mitomicyin C, Acetaminophen, Dexamethasone, Diphenyhdramine, Hydrochloride, Cromolyn, 3-(1H-Tetrazol-5-yl)-9H-thiol-xanthene-9-one 10,10-dioxide monohydrate, H1 and H2 histamine antagonists (H1 antagonists: mepytramine or triprolidine) transforming growth factor alpha, anti-transforming growth factor beta, epidermal growth factor, vascular endothelial growth factor, anti-transforming growth factor beta antibody, anti-fibroblast antibody, anti-transforming growth factor beta receptor antibody, arginine-glycine-aspartic acid, REDV, or a combination thereof.

Categories of tissues whose normal structure and or function is controlled by TRM, include, for example, biological tissues of vertebrates, invertebrates; normal tissue; injured tissue; regenerating tissue; repairing tissue; cancer tissue; mutant tissue; engineered tissue; artificial tissue; stem cell tissues; hybrid tissues; endothelial tissue; fibroblasts; epithelial tissue; muscle tissue; fat tissue; lymphocytes; macrophages; mast tissue; polymorphonuclear leukocytes; red blood cells, soft tissue; neurologic tissue; osteoblasts; osteoclasts; nerve; brain tissue; bone tissue; tissue derived stem tissue; blood derived stem tissue; and/or bone derived stem tissue.

Categories of tissues whose structure or function is controlled by TRM ex vivo include, for example, tissues originally derived from embryonic, neonatal, juvenile and/or adult tissues. Categories of tissues whose structure or function is controlled by TRM in vivo and or ex vivo include, for example, embryonic tissues, neonatal tissues, juvenile or adult skin. Injured tissues controlled in vivo and or ex vivo by TRM, include, for example, normal embryonic tissues, neonatal tissues, juvenile or adult skin. Tissues controlled in vivo and or ex vivo by TRM, include, for example, include embryonic tissues, neonatal tissues, juvenile or adult soft tissue, hard tissue, e.g. bone), skin, cardiac system, pulmonary, hepatic, gastrointestinal tract, biliary tract, urinary tract, genital tract, vision, neurologic or endocrine systems, blood vessels, bones, joints, tendons, nerves, muscles, the head, the neck, or any organ system or combinations there of.

In one embodiment of the present invention factors that are used to control vascular endothelial cell function in vitro (i.e. cell response modifiers 18) also may induce or suppress new blood vessel formation in vivo thus under the right circumstances they are also tissue response modifiers 20. For example, these factors may include: Vascular Endothelial Growth Factor (VEGF); Fibroblast Growth Factor (FGF); Interleukin-8 (IL-8); Angiogenin; Angiotropin; Epidermal Growth Factor (EGF); Platelet Derived Endothelial Cell Growth Factor; Transforming Growth Factor α (TGF-α); Transforming Growth Factor β (TGF-β); Nitric Oxide; Thrombospondin; Angiostatin; and Endostatin.

In one embodiment of the present invention, cell response modifiers 18 are used, but because they also operates to control inflammation and immune responses as well as development in vivo they are also examples of cell response modifiers that can act in vivo as tissue response modifiers 20. For example, cytokines and growth factors included in this operative definition include: TH1/TH2 Interleukins (IL-2, IL-4, IL-7, IL-9, IL-10, IL-12, IL-13, IL-15, IL-16, IL-17); the IL-1 family (IL-1-alpha, IL-1Ra, IL-18, IL-1-beta); the TNF family, for example TNF Ligand and TNF/NGF Receptor Families, TNFalpha, Lymphotoxin alpha and beta, Fas Ligand, CD40 Ligand, CD30 Ligand, CD27 Ligand, RANK Ligand Apo2L/TRAIL; the IL-6 family, for example, IL-6 Ligand and Receptor Family, IL-6, IL-11, Oncostatin M, CT-1; macrophage activation, such as, IFNalpha, IFN beta, and IFNomega Ligands, IFNgamma, Osteopontin, MIF; TGF beta, BMP Family, PDGF, VEGF, Poxvirus Vascular Endothelial Growth Factor (VEGF) Homologs of Orf Virus, Angiostatin, Activin, Endostatin, Methoxyestradiol, Poxvirus Growth Factors Related to EGF; IL-3, IL-5, Stem Cell Factor, GM-CSF CSF-1, G-CSF, Erythropoietin, Thrombopoietin; MGSA/GRO, ENA-78, IL-8, H. GCP-2, A. CTAP-III, betaTG, and NAP-2, Platelet Factor 4, IP-10 MIG, SDF-1, BLR1 Ligand/BCA-1/BLC, 9E-3/cCAF; MCP-1, MCP-2, MCP-3, MCP-4, and MCP-5RANTES, I-309, MIP-alpha, MIP-beta, Eotaxin, PARC, Eotaxin 2, MIP-gamma/MRP-2, Mu C10, Leukotactin 1, CKbeta8-, B. HCC-1, SLC (6CK-ine), ELC, H TECK/CCL25, CC Chemokine of Molluscum Contagiosum Virus, Lymphotactin, Fractalkine, Poxvirus Secreted Complement Control Proteins; IL-2 Family Receptors, IL-2 Receptor, IL-4 Receptor, IL-7 Receptor, IL-9 Receptor, IL-10 Receptor, IL-12 Receptor, IL-13 Receptor, IL-15 Receptor, IL-16 Receptor (CD4), IL-17 Receptor, Prolactin Receptor; IL-1 Family Receptors, such as, IL-1 Receptor Family, IL-1 Receptor Type I, Poxvirus IL-1beta Receptor Homologs, IL-18 Receptor, IL-1 Receptor Type II; TNF Receptors, Poxvirus TNF Receptor Homologs, Lymphotoxin beta Receptor, Fas, CD40, CD30, 4-1BB, RANK, Osteoprotegerin, CD27, HVEM, DR4, DR5, DcR1, DcR2, DcR3, O×40, GIT Receptor;IL-6 Receptor; IL-11 Receptor, OSM Receptor, CT-1 Receptor; IFNgamma Receptor, Poxvirus IFNgamma Receptor Homologs, IFN c beta Receptor, Poxvirus IFN c beta Receptor Homologs, Osteopontin Receptor, TGF beta Receptors, BMP Receptor, Hematopoietic Receptors, for example the Hematopoietic Receptor Family of IL-3 Receptor, IL-5 Receptor, SCF Receptor, GM-CSF Receptor, G-CSF Receptor, TPO Receptor; CXC Chemokine Receptors, such as, CXCR1 and CXCR2, CXCR3, CXCR4, CXCR5, R. CC, C, and CX3C; CC Chemokine Receptors, such as, CCR1, CCR2, CCR3, CCR4, CCR5, CCR6, CCR7, CCR8, D6, ECRF3, Poxvirus Membrane-bound G Protein-coupled Receptor Homologs, US28, Kaposi's Sarcoma-associated Herpesvirus GPCR, DARC, CX3CR1, Poxvirus Secreted Chemokine-binding Proteins, CCR9, XCR1; and Miscellaneous non-Cytokine Proinflammatory Factor Receptor, such as C5a Receptor, C3a Receptor, PAF Receptors, fMLP Receptors, Opioid mu, delta, and kappaReceptors for Endorphins, Lipoxin A4 Receptor, ACTH Receptor, BLTR: the Leukotriene B4 Receptor, PACAP and VIP Receptors, Lysophospholipid Growth Factor Receptors.

In one embodiment of the present invention the matrix material 22 may include: basement membranes, for example Matrigel™; fibrin clots, including plasma derived clots; collagens, for example, fibrillar collagens (types I, II, III, V and IX collagen); basement membrane collagen, such as type IV collagen; other collagens (types VI, VII, IX, XVII, XV and XVIII collagen); fibronectin; laminin; proteoglycans; glycoproteins; glycoaminoglycans; elastins; hyaluronan; adhesive glycoproteins; mucins; and polysaccharides. In some cases, certain factors can be included with the matrix material 22 to advantageously enhance the characteristics of the matrix material 22 and/or its production. For example, factors that can be included are: TGF-beta; FGF; angiotensin II; Insulin-like growth factor; and Ascorbic acid.

In one embodiment of the present invention, the matrix material 22 is primarily composed of fibrin. The matrix material 22 may also be composed of a solubilized basement membrane preparation such as Matrigel™ as supplied from BD Biosciences. The solubilized basement membrane, like fibrin, is a naturally occurring protein matrix/bio-hydrogel, that has a wide variety of binding sites for cells and factors. These factors may include growth factors and cytokines. For example, the solubilized basement membrane may include laminin, collagen, including collagen IV, heparin sulphate proteoglycans, and entactin. Solubilized basement membrane has been used extensively as a cell matrix/depot in a wide variety of in vitro and in vivo studies particularly in the area of tumor cell biology and angiogenesis.

In one embodiment of the invention the solubilized basement membrane is a liquid at 4° C. but becomes a solid bio-hydrogel when warmed to 37° C. This ability to convert solubilized basement membrane from a liquid to a solid by simply raising the temperature, allows for a wide variety of strategies for entrapping genetically engineered cells, factors, proteins and genes. It should be understood that the terms entrap, entraps, entrapped, entrapping, and the like are intended to include for the purpose of this application the concept that the matrix material 22 provides a mechanical association with the biological cells and/or that the matrix material 22 provides specific binding sites for the biological cells. For example, specific binding sites which include receptor and/or adhesion sites.

In one embodiment of the present invention stem or progenitor cells 14c are included in the ATS. These stem or progenitor cells may be included in a matrix material 22, which is selected based on the origin of the stem or progenitor cells. For example, expansion of undifferentiated stem cells, in vitro, may accomplished with a gelatin matrix material; expansion of nestin+neural progenitor cells may be accomplished with laminin, RA, Survival of embryonic stem cell derived motor neurons with basement membrane, and endothelial cells with collagen IV. If, for example, the stem or progenitor cells are of a bone marrow origin of the MSC, MAPC, or HSC type, then fibronectin and or basement membranes may be used. For example, expansion in vitro of undifferentiated MAPCs with fibronectin; osteoblasts with fibronectin; endothelial cells with fibronectin; and hepatocyte-like cells: basement membranes. If, for example, the stem or progenitor cells are of an adult tissue origin of the hepatic oval cell, NSC/NPC, adipose stem cell, or MDSC type, then fibronectin, laminin and/or collagen may be used. For example, expansion of undifferentiated oval cells with fibronectin; hepatocyte with fibronectin; pancreatic islet with fibronectin; neuron, glial cells with fibronectin, laminin; expansion of MDSCs with collagen, and osteoblast with collagen.

In one embodiment of the present invention, several growth factors or cytokines may be used as, for example, CRM 18 to promote stem or progenitor cell proliferation and differentiation in vitro. For example, if the stem or progenitor cells are embryonic stem cells, then expansion of undifferentiated ES cells can be accomplished with LIF; pancreatic endocrine progenitor with bFGF; pancreatic islet with bFGF; expansion of Nestin+neural progenitors with bFGF; RASurvival of ES-derived motor neurons with BDNF, NT-3, CNTF, GDNF; glial progenitor cells with bFGF, PDGF-AA; adipocyte13RAChondrocyte with BMP-2, BMP4; dendritic cells: GM-CSF, IL-3; and endothelial cells with VEGF. If the stem or progenitor cells are derived from bone marrow and are of the MSC, MAPC, or HSC types, then, for example, osteoblast may be utilized with BMP-2, bFGF; chondrocyte with TGF-β3; neuron, glial cells with EGF, BDNF; expansion of undifferentiated MAPCs with EGF, PDGF-BB; chondrocyte with TGF-β1; endothelial cells with VEGF; hepatocyte-like cells with FGF-4, HGF; and platelets, red/white blood cells with IL-3, IL-6, G-CSF. If the stem or progenitor cells are derived from adult tissues and are of the Hepatic oval cell, NSC/NPC, Adipose stem cell or MDSC types, then, for example, expansion of undifferentiated oval cells can be accomplished with SCF, Flt-3 ligand, IL-6, LIF; hepatocyte with HGF, EGF; pancreatic islet with SCF, Flt-3 ligand, IL-3; expansion of NPCs with bFGF, EGF, LIF; neuron, glial cells with bFGF, EGF, PDGF-AA, PDGF-AB, PDGF-BB, NT-4, CNTF; osteoblast with TGF-β1; expansion of MDSCs with IGF-1, EGF, SCF, FGF2; and osteoblast: BMP-2.

In one embodiment of the present invention stem or progenitor cells 14c are promoted utilizing other factors as, for example, TRM 20. For example, if the stem or progenitor cells are embryonic stem cells, then pancreatic islet cells can be utilized with nicotinamide; expansion of Nestin+ neural progenitors can be accomplished with poly-ornithine; neurons with poly-ornithine, RA; Adipocytes with RA; and osteoblasts with RA, dexamethasone, ascorbate, β-glycerol phosphate. If the stem or progenitor cells are derived from bone marrow and are of the MSC, MAPC, or HSC types, then, for example, osteoblasts with dexamethasone, ascorbate, β-glycerol phosphate; chondrocytes with dexamethasone; neuron, glial cells with RA; adipocytes with dexamethasone, insulin, indomethacin, 1-methyl-3-isobutylxanthine; expansion of undifferentiated MAPCs with 2% FBS; osteoblasts with dexamethasone, ascorbate, β-glycerol phosphate; platelets, red/white blood cells with erythropoietin, thrombopoietin. If the stem or progenitor cells are derived from adult tissues and are of the Hepatic oval cell, NSC/NPC, Adipose stem cell or MDSC types, then, for example, pancreatic islet cells can be utilized with nicotinamide; osteoblasts with Dexamethasone, ascorbate, β-glycerol phosphate; chondrocytes with insulin, ascorbate; and adipocytes with dexamethasone, insulin, indomethacin, 1-methyl-3-isobutylxanthine.

One embodiment of the present invention includes the use of implantable sensors 10, which include, for example, chemical sensors and biosensors such as glucose sensors. However, other devices may be used in addition to the sensor 10, or may replace the sensor 10. For example: bioreactors for liver, kidney or other organ support systems; catheters; artificial arteries; artificial organs; tissue fragment-containing devices; cell-containing devices; ligament replacements; bone replacements; coronary pacemakers; lap-bands, monitors; artificial larynxes; prostheses; brain stimulators; bladder pacemakers; shunts; stents; tubes; defibrillators; cardioverters; heart valves; joint replacements; fixation devices; ocular implants; cochlear implants; breast implants; neurostimulators; bone growth stimulators; vascular grafts; muscle stimulators; left ventricular assist devices; pressure sensors; vagus nerve stimulators; drug delivery systems; sutures and staples. In addition the devices may include implants. For example: prostheses, such as joint replacements; artificial tendons and ligaments; dental implants; blood vessel prostheses; heart valves; cochlear replacements; intraocular lens; mammary prostheses; penile and testicular prostheses; tracheal, laryngeal, and esophageal replacement devices; artificial organs such as heart, liver, pancreas, kidney, and parathyroid; repair materials and devices such as bone cements, bone defect repairs, bone plates for fracture fixation; heart valves; catheters; nerve regeneration channels; corneal bandages; skin repair templates; scaffolds for tissue repair and regeneration; and devices such as pacemakers, implantable drug delivery systems (e.g., for drugs, human growth hormone, insulin, bone growth factors, and other hormones). Furthermore, the device may include implantable drug delivery systems such as those disclosed in U.S. Pat. Nos. 3,773,919, 4,155,992, 4,379,138, 4,130,639, 4,900,556, 4,186,189, 5,593,697, and 5,342,622 which are incorporated in their entirety by reference herein. Implantable sensors for monitoring conditions such as blood pH, ion concentration, metabolite levels, clinical chemistry analyses, oxygen concentration, carbon dioxide concentration, pressure, and glucose levels are known. Blood glucose levels, for example, may be monitored using optical sensors and electrochemical sensors. It should be understood that the implant devices may become embedded, or otherwise integrated, into the biological system.

In general, the material of the invention may be alternately formulated to comprise, consist of, or consist essentially of, any appropriate components herein disclosed. The material of the invention may additionally, or alternatively, be formulated so as to be devoid, or substantially free, of any components, materials, ingredients, factors, cellular constituents, cytokines, growth factors, tissue types, genetic elements, adjuvants or species used in the prior art compositions or that are otherwise not necessary to the achievement of the function and/or objectives of the present invention.

EXPERIMENTAL EXAMPLES

In one embodiment of the invention, a gene transfer system is included wherein a genetically engineered cell suitable for use in the ATS is produced. For example, as experimentally shown, a Rous Sarcoma Virus Vector Model for Gene Transfer was created wherein a helper-independent retroviral vector, RCAS, derived from Rous Sarcoma Virus (RSV) was used for gene transfer in the in vitro and ex ova CAM model studies. A mouse VEGF gene (mVEGF), genebank number M25200, said genebank disclosure incorporated fully herein by reference and associated with the sequence as shown in FIG. 22, was inserted into the RCAS proviral plasmid vector in both "sense" and "antisense" orientations using standard recombinant DNA manipulations. Specifically, a 908 by Taq I fragment containing the mVEGF open reading frame was mobilized from pBSK+mVEGF and ligated into the unique Cla I site of the RCAS-BP(A) proviral vector plasmid. The ligation products were screened by restriction mapping and both sense and anti-sense orientations were obtained. The resulting mVEGF and anti-mVEGF proviral DNAs were transfected into DF-1 chicken fibroblast cells using lipofectamine, and the cultures were passaged for two weeks to allow viral replication.

In one embodiment of the invention, evaluation of the in vitro impact of the RCAS viral vector on cell viability and morphology can be made wherein, as experimentally shown, once viral replication into DF-1 cells is successful, the in vitro impact of the RCAS viral vector on viability and morphology of the chicken DF-1 cell line can be evaluated. The RSV-derived RCAS vector efficiently infected DF-1 chicken fibroblasts and CAMs, and is easy to construct and propagate. FIGS. 2A to 2E demonstrates that no effect on DF-1 cell viability and morphology was noted for any of the RCAS vectors used in these studies. The successful infection of the DF-1 cells was directly demonstrated using the GFP RCAS virus, which transformed the non-fluorescent DF-1 cells into fluorescent cells as shown in FIGS. 2D and 2E. Additionally, the presence of the RCAS virus in DF-1 cell cultures was demonstrated by immunocytochemistry using an antibody to the Rous sarcoma virus p27 gag gene product (data not shown) as well as soluble p27 viral coat protein.

Evaluation of Mouse mVEGF Protein Expression and RCAS Avian Leukosis (P27) Protein Expression after Viral Infection can be made in one embodiment of the invention wherein after it is established that the viral infection did not impact cell viability or morphology, a determination of the virus (p27) and mVEGF expression in the DF-1 cell lines can be made. Experimentally, to determine and correlate mVEGF protein and RCAS viral production over a one-week period, the various infected DF-1 cells were seeded at low confluence and monitored for their products until they reached confluence. For that, DF-1 cells and DF-1 cells previously infected with RCAS carrying gene for mVEGF, antisense-mVEGF (AS-mVEGF) or EGFP were seeded in triplicate in 12-well plates at $1 \times 10^4$ cells/well. The following days, an aliquot of the culture medium was taken out and replaced by fresh serum containing media. Aliquots were stored at −70° C. till evaluated for mVEGF and p27 expression. Protein expression of mVEGF and p27 were measured by ELISA as described above. Measured for these studies was p27 antigen (a marker of virus content/production by cells) and mVEGF production by ELISA from the control DF-1 cells as well as the viral transfected cells using ELISA technology as shown in FIG. 3. All cell lines except the non-infected parental DF-1 cells, produced significant amounts of p27 antigen, as shown in FIG. 3A; (data not shown for DF-1, GFP:DF-1, AS-mVEGF: DF-1). The mVEGF production was detected only from RCAS-mVEGF transfected DF-1 cells as shown in FIG. 3A and FIG. 3B. The peak mVEGF production by the mVEGF: DF-1 cells in vitro was 978±155 pg mVEGF/ml. A time study of p27 and mVEGF expression in RCAS-mVEGF transfected DF-1 cells (sub-confluent to confluent: FIG. 2A) indicated that both p27 and mVEGF production peaked at day 6 in culture (i.e. 80% confluent cells). Thus, our ELISA data clearly indicate that we can 1) infect DF-1 cells with Rous Sarcoma Virus (anti-p27), 2) transfect mVEGF into these DF-1 cells and 3) that these transfected cells clearly produce both RCAS virus and mVEGF.

In one embodiment of the invention a determination of cell viability and growth of cells incorporated into a matrix material composed primarily of fibrin can be made. As experimentally shown a naturally occurring matrix (fibrin) was used to investigate its utility to entrap cells and still allow cell viability. In addition, the formation of fibrin clots served as a matrix to keep the cells localized, which is important for later in vivo investigation where target gene delivery is an important issue. Briefly, equal volumes of human fibrinogen (Fg) with varying Fg concentration ranging from 6, 3 and 1 mg/ml (Sigma Chemical, St. Louis, Mo.) and cell suspension (2 million cells/ml) or media, were mixed and a 50µl aliquot was placed into the center of a 6-well petri-dish. 5 µl of a 2.5E-3 U/µl thrombin solution (Sigma Chemical, St. Louis, Mo.) was added directly onto the fibrinogen/cell-mixture. Cells used in these studies included DF-1 cells, GFP-DF-1, AS-VEGF: DF-1 and VEGF:DF-1. Polymerization was complete within 15 minutes at 37° C. and produced a three-dimensional gel of fibrin entrapping cells or culture media in the center of the dish. As shown in FIG. 4 GFP:DF-1 cells are entrapped in a fibrin clot. 3 ml of the culture media supplemented with Polybrene were added to each well after polymerization of fibrin. A 1 ml aliquot was taken out of each well daily for a total of 10 days and replaced with fresh DF-1 culture media. Aliquots were stored at −70° C. till assayed by ELISA for p27 and VEGF expression as described earlier. Culturing the cells with varying concentrations of Fg was used to show that virus is released into the culture media and to determine fibrin clot stability over a 10-day culture period.

In one embodiment of the invention, the In Vitro Evaluation of VEGF Protein Expression and Avian Leucosis p27 Protein Expression Entrapped in a Fibrin Clot at various Fg Conditions can be made. As experimentally shown, once fibrin successfully entraps cells over a 1-week time frame, as shown in FIG. 4, a determination of the virus (p27) and VEGF expression in the DF-1 into the culture media incubated at various Fg condition was made. As shown in FIG. 5A, VEGF: DF-1 cells entrapped in a fibrin matrix with Fg concentration of 3 or 6 mg/ml expressed similar VEGF concentration. Fg concentration of 1 mg/ml had a slightly lower VEGF expression when compared to Fg concentrations of 3 or 6 mg/ml. Control VEGF:DF-1 cells without addition of fibrinogen showed significant lower level of VEGF expression than cells embedded in fibrin matrix. This indicates that the fibrin matrix is responsible in modulating expression of VEGF. There was no VEGF expression detected in DF-1, GFP:DF-1 or AS-VEGF:DF-1 cell lines entrapped in the fibrin matrix (data not shown). All cell lines except the non-infected parental DF-1 cells produced significant amounts of p27 antigen, which was not dependent on Fg concentration as shown in FIG. 5B (data not shown for DF-1, GFP:DF-1 and AS-VEGF: DF-1 cell lines). Thus, this ELISA data clearly indicate that infected DF-1 cells entrapped in fibrin matrix were able to express significant viral protein p27 and that VEGF:DF-1 cells entrapped in fibrin matrix also produced significant levels of VEGF.

A determination of the impact of thrombin on infected and parental DF-1 cells can be made in one embodiment of the invention. For example, as experimentally shown, once is shown that DF-1 infected cells entrapped in fibrin matrix express significant levels of p27 and VEGF in the case of VEGF:DF-1 cells, the impact of Thrombin to DF-1 cells can be determined. For this, a Fg concentration of 3 mg/ml was used since it was demonstrated that cells embedded in a fibrin matrix of 3 mg/ml Fg showed a similar behavior as cells embedded in 6 mg/ml Fg. Cells were processed as described above with regard to the determination of cell viability and growth of cells incorporated into a matrix material of fibrin. However, an additional control was added. This additional control included cells treated with 5 µl of a 2.5E-3 U/µl thrombin solution but no fibrinogen. As described above, a 1 ml aliquot was taken out of each well daily for a total of 6 days and replaced with fresh DF-1 culture media. Aliquots were assayed by ELISA for p27 and VEGF expression as described earlier.

In one embodiment of the invention, the in vitro evaluation of VEGF protein expression and avian leucosis p27 protein expression entrapped in a fibrin clot at 3 mg/ml Fg can be made. As shown experimentally, a fibrinogen concentration of 3 mg/ml and a thrombin addition of 5 µl of a 2.5E-3 U/µl was used. As can be seen in FIG. 6A, VEGF expression of VEGF:DF-1 cells entrapped in fibrin matrix was similar when compared to thrombin treated VEGF:DF-1 cells or control cells (VEGF:DF-1 cells without addition of thrombin and/or Fg). As expected, there was no VEGF expression detected in DF-1, GFP:DF-1 or AS-VEGF:DF-1 cell lines either entrapped in the fibrin matrix or with thrombin addition (data not shown). All cell lines except the non-infected parental DF-1 cells produced significant amounts of p27 antigen, which was significant different for Fg or thrombin condition as shown in FIG. 5B (data not shown for DF-1, GFP:DF-1 and AS-VEGF:DF-1 cell lines).

A determination of cell viability and growth incorporated into a matrix material primarily composed of isolated basement membrane is included in one embodiment of the invention. Experimentally, it was previously shown that a matrix material primarily composed of fibrin successfully entraps cells and that these cells were also able to release viral proteins. An experimental study was conducted to determine if the matrix Matrigel™ was able to behave in a similar fashion as fibrin. Matrigel™, as previously discussed, is an isolated basement membrane obtained from cells cultured in vitro, which has been used in a wide variety of in vivo and in vitro studies of cell attachment, cell growth and angiogenesis. Like fibrin, Matrigel™ is a naturally occurring matrix derived from basement membrane, that has a wide variety of binding sites for cells and factors (including growth factors and cytokines). Matrigel™ has been used extensively as a cell matrix/depot in a wide variety of in vitro and in vivo studies particularly in the area of tumor cell biology and angiogenesis. Matrigel™ is a liquid at 4° C. but becomes a solid biological matrix when warmed to 37° C. This ability to convert Matrigel™ from a liquid to a solid by simply raising the temperature, allows for a wide variety of strategies for entrapping genetically engineered cells, factors proteins and genes. Matrigel™ and other isolated basement membrane materials possess the characteristics to serve as a tissue interactive biological matrix for the ATS. DF-1 cells were utilized to determine the virus and VEGF expression in the DF-1 cell lines. Briefly, Matrigel™ and DF-1 cells (e.g. DF-1, GFP:DF-1, VEGF:DF-1) were mixed together at a ratio of 3:2 and 50 µl of Matrigel™ cell suspension was pipetted into 6-well tissue culture plate. Wells were supplemented with culture media. An aliquot was taken out of each well daily for a total of 1 week and replaced with fresh DF-1 culture media. Aliquots were stored at −70° C. till assayed by ELISA for p27 and VEGF expression as described earlier.

In one embodiment of the invention, after determining that Matrigel™ successfully entraps cells the viral release of entrapped cells in a Matrigel™ clot can be determined. Experimentally the infectivity of virus carrying gene for GFP entrapped in Matrigel™ was determined. For this determination, 3E5 DF-1 chicken fibroblast cells were plated onto a 6-well plate. Liquid Matrigel™ was mixed with GFP:RCAS viral supernatant at a ratio of 3:2 and 100 µl of Matrigel™/virus supernatant was placed in one well of a 6-well plate. As controls, 100 µl of Matrigel™ was added to wells of a 6-well plate. In addition, there was added 100 µl of Matrigel™/virus supernatant to 0.7 cm² nylon fabric disks and placed nylon containing Matrigel™/virus mixture into wells of a 6-well plate. Nylon fabric with and without addition of 100 µl Matrigel™ served as additional controls in this study. In order to prevent polymerization of Matrigel™ prior to placement into well, Matrigel™ was only handled with pipette tips kept on ice. Plates were placed in 37° C. incubator and 90% humidity and cells were inspected for green fluorescence daily. After a few days of incubation only DF-1 cells with viral addition showed green fluorescence cells. Hence, virus entrapped in Matrigel™ is still able to infect DF-1 cells.

In typical bioengineering applications, it is often desirable to mark the tissue site at which the cell factor production occurs. Therefore, in one embodiment of the invention, it is desirable to determine if nylon fabric (mesh 100 µm pore size, Sefar America Inc., Depew, N.Y.) is usable as a cell carrier system. Specifically, for the cell carrier system the nylon fabric was cut in 7 mm disks, ethylene oxide sterilized, dip coated in sterile egg white (EW), and placed into a tissue culture treated 48-well-plate and manifested with an o-ring. Utilized were DF-1 chicken fibroblast infected with RCAS carrying gene for mVEGF, RCAS carrying gene for antisense to mVEGF, and RCAS carrying gene for EGFP. As an additional control also utilized were DF-1 chicken fibroblast only. Confluent monolayers were gently washed with phosphate buffered saline (PBS), pH 7.2, and after a short exposure to trypsin, the cells were suspended in serum containing media. The cell suspension was counted in a hemocytometer and diluted with cell culture medium to a final concentration of $5 \times 10^5$ cells per ml. A 100 µl aliquot of that cell suspension was added to the nylon fabric disk and the cells were allowed to grow on the nylon for several days. As an additional control, an aliquot of cells was also added to nylon fabric disks, which were not dip-coated with EW. In order to determine cell density on nylon fabric, the nylon fabrics were transferred at day 4 post addition of cells to tube containing fixative, washed repeatedly and stained with haematoxylin solution. Excess haematoxylin stain was washed off and cells on nylons were observed for cell density. It was observed that a higher number of cells grew on meshes previously dip-coated in egg white compared to meshes without egg-white coat. Furthermore, cells with addition of egg white behaved similar when compared to cells grown in media without egg-white addition.

Experimentally, as discussed above, it was shown that DF-1 cells were able to grow on protein treated nylon fabric. One embodiment of the invention includes growing cells on Nafion® coated nylon fabric. Nafion® is a sulfonated tetrafluoroethylene based fluoropolymer-copolymer. The Nafion® fluoropolymer-copolymer is a material that is included in the outer layer of chemical- and bio-sensor described below. Experimentally nylon fabric disks, as described previously, were dip-coated with Nation® fluoropolymer-copolymer (Sigma) three times. After each coat a drying time at room temperature for a period of 10 minutes was observed. The Nafion® fluoropolymer-copolymer coated nylon disks were then placed into an oven for 30 min at 120° C., nylon fabrics were washed 3-times with phosphate buffered saline and placed into a 48-well tissue culture plate. Nafion® fluoropolymer-copolymer-treated nylon fabrics and non-treated disks were secured at bottom of plate with the help of an o-ring (total of 3 nylon fabrics per condition). GFP:DF-1 cells at a concentration of 5E4 cells per well were added to each well and plate was incubated at 37° C. and 90% humidity. Wells were inspected daily for cell survival and cell proliferation. Fibroblast adhered sparsely to both Nafion® fluoropolymer-copolymer coated nylon fabric and non-coated nylon fabric in a similar pattern.

One embodiment of the invention includes adhesion of DF-1 cells to Nafion® fluoropolymer-copolymer. Experimentally, Nafion® fluoropolymer-copolymer disks (50 mm diameter) were washed repeatedly with $dH_2O$ and soaked overnight in 0.9% sterile NaCl. Additional Nafion® fluoropolymer-copolymer disks were also dip-coated with Nafion® fluoropolymer-copolymer (Sigma) in order to confirm various nation Nafion® fluoropolymer-copolymer conditions used for sensor coatings. The disks were cured at 120° C. for 30 minutes. After curing, the Nafion® fluoropolymer-copolymer disks were washed repeatedly with $dH_2O$. Nafion® fluoropolymer-copolymer disks (with and without EW coating) and Nafion® fluoropolymer-copolymer-coated disks (non-cured and cured disks with and without EW coating) were placed in 48-well plate and secured to bottom of well with o-ring (n=4 for each condition). Cells added to plain wells with and without EW coating of tissue culture bottom served as positive controls. Cells were observed daily for cell survival, cell adherence and cell proliferation. In general, cells grew much better on EW coated disks when compared to non-coated EW disks with exception of Nafion® fluoropolymer-copolymer disks (non-cured). Here cells did neither adhere to EW coated nor non-EW coated Nafion® fluoropolymer-copolymer disks and therefore did not survive. Cells on Nafion® fluoropolymer-copolymer coated Nafion® fluoropolymer-copolymer disks (cured) adhered only sparsely to non-EW treated disks but these adhered cells were able to proliferate. Cells on Nafion® fluoropolymer-copolymer coated Nafion® fluoropolymer-copolymer disks (cured) treated with EW and Nafion® fluoropolymer-copolymer (cured) disks treated with EW showed a similar behavior as control wells (wells without addition of disks but with and without addition of EW).

One embodiment of the invention includes adhering genetically engineered cells and fibrin matrix systems to nylon. As discussed, it was experimentally demonstrated that growing cells on the nylon fabrics was possible, therefore the approach of utilizing nylon fabrics as a carrier for fibrin matrix and various cell lines was undertaken. Experimentally utilized were 7 mm nylon fabrc-disks (foot mesh 35 and 1 µm pore size, SefarAmerica Inc., Depew, N.Y.) as a carrier for the cell-fibrin biological matrix. Confluent monolayers of the various cell lines were washed, trypsinized and re-suspended in serum containing media to a final cell concentration of 2 million cells/ml. VEGF:DF-1 cells or control cells (DF-1, GFP:DF-1) were mixed with equal volumes of a physiological fibrinogen (Fg) solution (3 mg Fg/ml). Next, 50 µl aliquots of each of these solutions were placed onto the nylon disks with the addition of 5 µl of a 2.5E-3 U/µl thrombin solution (Sigma Chemical, St. Louis, Mo.). The nylon disk-cell-fibrin mixture was placed into a tissue culture incubator at 37° C. and 90% humidity. Polymerization of fibrin matrix was usually completed within a few minutes once placed into incubator. Cell adherence and cell proliferation of cell-fibrin matrix systems were investigated with a light microscope daily for up to one week. DF-1 cells and DF-1 cells infected with RCAS carrying genes for mVEGF or EGFP suspended in a fibrin matrix and placed on the nylon disks, were all able to grow well on the nylon fabric.

One embodiment of the invention includes preparation of an ex ova model of the chick embryo. Experimentally, fertilized chicken eggs (White Leghorn Strain) were obtained from the University of Connecticut Poultry Farm (SPAFAS, Storrs, Conn.). Initially, the fertilized eggs were placed horizontally on trays and incubated at 38° C., with a relative humidity of 90% for 3 days. It should be noted that placing the eggs horizontally during the initial incubation period assures that the embryo develops in its proper position at the top of the egg. After the initial 3 days of incubation the resulting eggs were used in the preparation of the ex ova or shell-less embryo culture system. All steps in the preparation of the ex ova model were conducted under aseptic conditions. Briefly, the 3-day-old fertilized chicken eggs were first wiped with 70% ethanol and permitted to air-dry to reduce contamination from the egg-shell surface during the egg cracking procedure. The egg contents (embryo, yolk, albumin and chorioallantoic membrane (CAM)) were then directly transferred into a 25×100-mm plastic petri-dish (Fisher Scientific, Pittsburgh, Pa.) by cracking the underside of the egg against a sharp edge. Transferring of the egg contents without damaging yolk or embryo, and positioning of the blastodisc uppermost and central in the petri dish is critical in order to favor subsequent survival rate of the embryo. The resulting petri dishes, containing the chick embryo and CAM, were next placed back into a 38° C. incubator (with a relative humidity of 90%) for an additional 4 days (day 7 gestation). Generally, placement of various test materials onto the CAMs were conducted with chick embryos at gestation day 7, and test materials were simply placed directly on the CAM, and re-incubated at 38° C. and 90% humidity. The resulting CAMs were evaluated for gross morphology and histology for up to 8 days post placement (day 15 of gestation).

To evaluate and document any gross morphologic changes induced in the CAM by various test materials including biomaterials, CAMs were examined at various times post placement of the test material, using a Zeiss stereo-microscope SR. The gross morphology of tissue reactions to the various test materials was documented with SPOT camera (Diagnostic Instruments, Inc., St. Sterling Heights, Mich.). In parallel studies non-treated chick embryos CAMs were also evaluated for gross morphology, and documented as described for the test material described above. Generally for these studies, evaluation of gross appearance of test and control CAMs were done at 1 day, 4 days and 8 days post placement of the test material on the CAM.

For histological evaluation of tissue reactions induced in the CAMs, control or test material treated CAMs were fixed in situ (10% buffered formalin) at various days post placement of the test sample on the CAMs. The buffered formalin fixed tissue was then processed for paraffin embedding and sectioning. Generally, five µm sections were prepared of the various specimens, mounted on glass slides and stained with hematoxylin and eosin (H&E) for evaluation of histopathology. Histologic evaluation of tissue reactions in the CAMs was done on specimens obtained at 1 day, 4 days and 8 days post placement of the test materials.

Initially, the development of the chick embryo and CAM from day 3 to day 17 of gestation. The initial development (i.e. days 1-3) of the chick embryo occurs in ova, prior to transferring the entire egg content into a sterile petri-dish. Only egg contents without damage to the yolk or embryos, and with the position of blastodisc uppermost and central were used in this study as shown in FIG. 7A. Usually about 80% of the 3 day incubated eggs were successfully transferred to the petri dishes and into the incubator. Typically the major lose of embryos occurs during the first three to four days after transfer to the petri dishes, and ranges from 20-50%. Generally those embryos surviving the initial 3 days ex ova (day 6 gestation), have an excellent survival rate (i.e. up to almost a 100%). At day 3 ex ova, the CAM is spread evenly over yolk and egg white layer. By this time-point the CAM has significant development of the vasculature. With continued incubation, the CAM and its associated vasculature, develops as a flat membrane, which reaches the edges of the dish by day 10 as shown in FIG. 7C. By gestation day 14 areas of CAM are translucent due to reduction in yolk volume as shown in FIG. 7D. At gestation day 17 to 18 the vasculature is fully developed as shown in FIG. 7E. No difference in the CAM development is detected when comparing in ova versus ex ova growth.

It should be noted that histologically the CAM, a transient respiratory organ for the developing chick embryo, consists of a mesodermal stroma lined by an outer ectodermal (air side) and an inner endodermal composed of allantoic epithelium as shown in FIG. 8. The ectoderm layer is composed of a microvasculature, which serves primarily for gas exchange, and a chorionic epthelial layer. The mesodemal stroma is composed of a complex vasculature supported by thin collagen fibers and fibroblasts. The ectoderm and endoderm are separated from the mesoderm by basement membranes. The CAM has an approximate thickness of 100 to 200 μm.

In one embodiment of the invention chick ex ova CAM tissue, or other tissues, can be correlated to mammalian tissue with regard to similar reactions when stimulated with irritants or biomaterials. For example, experimentally, the CAMs were treated with a variety of substances and biomaterials including: 1) bacterial endotoxins (lipopolysaccarides, LPS); 2) thread/suture; 3) nylon; and 4) silastic tubing (silicone). Acute inflammation was induced in the CAMs using endotoxin (LPS) after placement of the endotoxin on top of the CAM, and chronic inflammation was induced using cotton thread, as discussed below. Finally, both silicone (silastic tubing) and nylon were also evaluated in the CAMs of the ex ova model, as discussed below.

Endotoxins are known to be potent inducers of acute inflammation in a wide number of mammalian tissues, thus first determined was the ability of endotoxins to induce acute inflammation in the ex ova CAM model. To induce acute inflammation in the CAM, 100 ng of an endotoxin from *Escherichia coli* 0111:B4 (Sigma, St. Louis, Mo.) was placed on 7-day-old embryo CAMs. For ease of visualization of the placement of the endotoxin on the CAM, the endotoxin was mixed with india ink. After various days post-placement of the endotoxin on the CAM, the CAMs were fixed with 10% buffered formalin in situ and processed for histology.

In order to evaluate the acute inflammatory response of the ex ova CAM, bacterial endotoxins were mixed with India ink, and was placed on top of the chorioallantoic membrane of 7-day-old embryos. The india ink was added to the endotoxin for ease of visualization over the 8 day time course of the study (days 1, 4 and 8 post placement). Gross morphologic evaluation of the CAMs demonstrated that post-placement of 1 to 8 days resulted no detectable gross pathology as shown in FIGS. 9B and 9C. FIG. 9A demonstrates the normal gross morphology of the CAM development of a 12-day-old embryo. Evaluation of H&E stained CAM tissue sections from day 1 post placement of endotoxins/india ink, demonstrated that bacterial endotoxins induced a strong acute inflammatory response, with influx of both plasma proteins (edema) and heterophiles (chick polymorphonuclear leukocytes (PMNs)) into the CAM tissue. Heterophiles are the equivalent to mammalian neutrophiles, and are a principal effector cell line of innate host defenses in avian. Generally, the acute inflammation induced by endotoxin/india ink remained localized on or near the surface of the ectoderm as shown in FIG. 9F. Hyperplasia of the ectodermal epithelial cells was all seen in the endotoxin/india ink treated CAMs. A thickening of the CAM occurred at sites of inflammation likely due to tissue edema. The endotoxin/india ink treated CAMs were also evaluated for tissue reactions after 4 days and 8 days post-placement of endotoxin/India ink. By 4 days post-placement of the endotoxin/india ink histologic evaluation of the CAMs indicated a massive influx of mononuclear leukocytes (monocytes and lymphocyte) into the ectoderm layer of the CAM as shown in FIG. 9G. After 8 days post-placement of the endotoxin/India ink, the inflammation displayed significant resolution, as shown in FIG. 9H. By day 8 post-placement (PP), the inflammation appeared to be resolving on the surface of the CAM. The Histology of normal CAM is provided for comparison as shown in FIG. 9E.

Implants frequently induce chronic inflammation (foreign body reactions) when implanted in mammalian tissues. Cotton sutures represent a classic model of foreign body chronic inflammation, and were used to evaluate tissue reactions in the ex ova CAM model. For these studies, cotton thread fibers (0.5 cm to 1 cm in length) were prepared by unwinding standard cotton thread and placed on top of the 7-day-old CAMs (3 day incubation in the shell (in ova) plus 4 days ex ova). The resulting fibers were evaluated for gross and histologic changes as described above. Additionally, it was noted that the incorporation of thread fibers was accelerated when the thread fibers were pre-coated (dipped) in sterile egg white, prior to placement on the CAMs. Samples were retrieved for gross and histological evaluation 1, 4 and 8 days post-placement of the thread fibers on the CAMs.

In the ex ova CAM model, tissue reactions to a "foreign object" (cotton thread fibers) was evaluated in the by implantation of cotton thread fibers on top of the CAM. It was demonstrated that egg white coated thread fibers were rapidly incorporated into the ex ova CAMs as shown in FIGS. 10A-10H. Gross evaluation revealed that 1 day after deposition most fibers were not significantly incorporated, but that thread fibers began to be incorporated 3 to 4 days post-placement as shown in FIGS. 10B and 10C. By day 8 there was extensive incorporation of the thread fibers with association of pink haze surrounding the thread fibers suggesting neovascularization around the incorporated fibers as shown in FIG. 10D. The gross morphology of the normal CAM of a 12-day-old chick embryo is presented in FIG. 10A. The resulting CAMs were next evaluated for histologic changes induced by the cotton fibers. At 1-day post-placement of thread fibers, most of the cotton fibers were on surface of CAM, with some incorporation of individual fibers as shown in FIG. 10F. Frequently, it was observed that chick PMNs (heterphiles) migrated from the microvasculature associated with the ectoderm, and surrounded the individual fibers of the thread on the surface of the CAM. When individual fibers are incorporated at this stage, heterophiles and other inflammatory cells immediately surround those fibers. By 4 and 8 day post-placement of the thread fibers an increase influx of mononuclear leukocytes (macrophages and lymphocytes) was seen, with formation of giant cells surrounding the individual fibers, a hallmark of chronic inflammation as shown in FIG. 10G-10H. Additionally, by 4 days post-placement, areas of focal necrosis surrounding large aggregates of cotton fibers were also seen, as well as fibroblast influx into the inflamed tissue. At day 8 post-placement of the cotton fibers there was continued presence of mononuclear leukocytes and giant cells surrounding thread fibers. Additionally, a significant increase in tissue necrosis, as well as the development of granulation tissue was seen. This granulation tissue was characterized by neovascularization, fibroblast influx, and collagen deposition as shown in FIG. 10H. These studies demonstrated that placement of an incompatible implant (i.e. cotton thread fibers) on the CAM induced not only acute inflammation, but also induced foreign body chronic inflammation and repair. Thus, it is clear that reactions seen in ex ova CAM model displays the same classic histologic hallmarks seen in foreign body induced chronic inflammation (i.e. macrophages, epithelial and giant cells) and repair (granulation tissue and fibrosis) of mammalian models.

In one embodiment of the invention the correlation between mammalian tissue and other tissue is determined with regard to medical grade nylon. Medical grade nylon is frequently used in implants, and generally induces minimal tissue reactions in mammalian tissues, thus we evaluated the reactivity of this biomaterial in the ex ova model. To test nylon reactivity in the ex ova model medical grade nylon screen (mesh 35 µm pore size, Sefar America Inc., Depew, N.Y.) was cut in 7 mm disks, steam sterilized, and dip coated in sterile egg white. The resulting nylon disks were then placed on the CAMs of 7-day-old chick embryos. After 1, 4 and 8 days post-placement of the nylon disks, the CAMs were fixed in situ and the resulting specimens were processed as described above for evaluation of gross morphology and histology. Frequently when the nylon disks incorporated into the CAM were sectioned the nylon fractioned the tissue or the nylon fibers fell out of the tissue during embedding processing. Although this did cause some loss of CAM tissue, routinely adequate amounts of CAM remained in each section for evaluation. This experimental study additionally showed that Egg white which contains glycoproteins and mucin excellerates the incorporation of biomaterials (nylon) into tissue.

Since a variety of biomaterials, such as nylon, are known to induce minimal tissue reactions when placed in mammalian tissues, the tissue reaction of the ex ova CAM to woven nylon fabric was evaluated. Gross morphology of a nylon screen placed on top of the ex ova CAMs for 1, 4 and 8 days can be seen in FIGS. 11A-11D. Evaluation of ex ova CAMs one-day post placement of the nylon screen indicated that there was little incorporation into the CAMs as shown in FIG. 11B. By 4 days post placement of the nylon screen, the screen was significantly incorporated within the CAM, and appeared as a translucent gel above the incorporated nylon screen disk as shown in FIG. 11C. After 8 days post-placement of the nylon screen, the nylon screen was almost totally incorporated as shown in FIG. 11D. For comparison, FIG. 11A shows a normal CAM of an 11-day-old Chick embryo. Histological evaluation of the tissue reactions of the ex ova CAMs to the nylon screens, as shown in FIGS. 11E-11H revealed that 1 day post-placement the CAM surrounding the mesh showed no tissue pathology, likely due to the limited incorporation of nylon disk in the CAM. The nylon screen, which is denoted by "N", can be seen "floating" (sectioning artifact) on top of the ex ova CAM as shown in FIG. 11F. When the nylon screen was placed on top of the CAM for 4 days, a moderate to significant incorporation was seen with no or little tissue reaction as shown in FIG. 11G. Day 8 post-placement showed a significant incorporation of the nylon disk into the CAM as shown in FIG. 11H. Little or no inflammation was seen associated with the incorporated nylon disk. These studies clearly indicate that the ex ova CAM reacts to nylon in a similar fashion as seen for tissue reaction induced by nylon in mammalian tissues.

Silicone has frequently been used in implants, and generally has minimal reactivity in mammalian tissues. To evaluate silicone reactivity in our ex ova model, 0.5 cm to 1 cm long medical grade silastic tubing (Dow Corning, Midland, Mich., 0.0301 cm ID×0.064 cm OD) were steam sterilized prior to placement on 7-day-old CAMs. The silastic tubing was coated prior to placement by dipping the tubing in egg white. At 1, 4 and 8 days post-placement of the silastic tubing, specimens were fixed in situ. The resulting CAMs were evaluated for gross morphology as shown in FIGS. 12A-12D and histologically, as shown in FIGS. 12E-H.

As discussed, silicone has been used in bioimplants since it induces minimal tissue reactions in mammals, thus the ex ova CAM for tissue reactivity to silicone tubing (i.e. silasic tubing) was evaluated. At day 1-2 post placement of the silastic tubing significant incorporation of the CAM can be seen grossly, with in-growth of the CAM tissue, including the CAM vasculature into the lumen of the tubing as shown in FIG. 12B. By day 4 post-placement of the silastic tubing, the silastic tubing showed consistent incorporation, with extensive in-growth of the CAM tissue and vasculature into the lumen of the tubing, as shown in FIG. 12C. Incorporation of the tubing continued at day 8 post-placement of the silastic tubing, as well as further in-growth of the CAM into the lumen, as shown in FIG. 12D. Histologic evaluation at CAM tissue day 1 post placement of the silasic tubing, indicated that no significant tissue reactions occurred in the CAM tissue surrounding the silastic tubing or in the CAM tissue and vasculature that had grown into the silastic tubing, as shown in FIG. 12F. At day 4 post-placement, CAM tissue reactions to silastic tubing were insignificant as seen histological, as shown in FIG. 12G. By day 8 post-placement of the silastic tubing, the CAM tissue continued to display little or no tissue reactions to the silastic tubing, as shown in FIG. 12H. Additionally, the day 8 luminal in-growth of CAM tissue continued to appeared healthy with numerous blood vessels present. These studies clearly demonstrate that the ex ova CAM response to silicone is similar to that seen in mammalian tissue, and support the validity of the ex ova CAM as a model of mammalian tissue reactions to biomaterials and bioimplants.

One embodiment of the invention includes the determination of RCAS viral infectivity of CAM. Experimentally after determining an effective viral vector system, which promoted gene transfer in vitro, as discussed above, the viruses were utilized to investigate their infectivity of the CAM of the chicken. Experimentally, utilized were DF-1 chicken fibroblast infected with RCAS carrying gene for mVEGF, RCAS carrying gene for antisense to mVEGF, and RCAS carrying gene for EGFP. As an additional control also utilized was DF-1 chicken fibroblast only. Cells were maintained in tissue culture flasks and once cells reached 80 to 90% confluence, cell media was collected, filtered using a low protein binding membrane (25 µm pore size) and 50 µl of collected media was added to CAM of 7 or 8 day old chicken embryo. Experience in the CAM model was that direct placement of only the GFP:RCAS virus on the CAM resulted in few fluorescent cells appearing on the CAM. In parallel studies using mVEGF:RCAS virus only, placement of the virus on the CAM resulted in little to no neovascularization. This may be due to the fact that viruses are very susceptible to drying effects.

One embodiment of the invention includes determining the infectivity of CAM utilizing genetically engineered cells. For example, genetically engineered DF-1 Cells. As discussed above, it was experimentally demonstrated that direct placement of the viral vector at the tissue site resulted in relatively poor virus-gene incorporation. This demonstration resulted in development and validation of a cell based viral vector delivery system, e.g. the GFP:DF-1 and mVEGF:DF-1 cells. Experimentally utilized were DF-1 chicken fibroblast infected with RCAS carrying gene for mVEGF, RCAS carrying gene for antisense to mVEGF, and RCAS carrying gene for EGFP. As an additional control, also utilized were DF-1 chicken fibroblast only. Confluent monolayers were gently washed with phosphate buffered saline (PBS), pH 7.2, and after a short exposure to trypsin, the cells were suspended in serum containing media. The cell suspension was counted in a hemocytometer and diluted with cell culture medium to a final concentration of $5 \times 10^5$ cells per ml. An aliquot of that cell suspension was added to the CAMs of 7 or 8-day-old chick embryos. After 4, 6 and 8 days post-placement of the cell addition, the CAMs were fixed in situ and the resulting specimens were processed as described above for evaluation of gross morphology and histology. Evaluation of the tissue demonstrated that direct placement of GFP:DF-1 cells on the CAM resulted in few fluorescent cells appearing on the CAM. In parallel studies using VEGF:DF-1 cells on the CAM resulted in little to no neovascularization. As was the case with only viral addition on the CAM, cells were also very susceptible to drying effects.

One embodiment of the present invention includes the preparation of genetically engineered cell-nylon systems for delivery of genes in the Ex Ova model. In vivo production of heterologous proteins is often most efficient when the tissue site is implanted with engineered factor-producing cells rather than viral vectors alone. In addition, in bioengineering applications, it would be desirable to mark the tissue site at which the factor production occurs. To address these issues experimentally a nylon fabric (mesh 35 and 1 μm pore size, Sefar America Inc., Depew, N.Y.) was utilized as both a cell carrier system, as well as a marker system, to track the site of cell transfer onto the CAM. Specifically, for the cell carrier system the nylon fabric was cut in 7 mm disks, ethylene oxide sterilized, dip coated in sterile egg white, and placed into a tissue culture treated 48-well-plate and manifested with an o-ring. The cells were DF-1 chicken fibroblast infected with RCAS carrying gene for mVEGF, RCAS carrying gene for antisense to mVEGF, and RCAS carrying gene for EGFP. As an additional control, also utilized were DF-1 chicken fibroblast only. Confluent monolayers were gently washed with phosphate buffered saline (PBS), pH 7.2, and after a short exposure to trypsin, the cells were suspended in serum containing media. The cell suspension was counted in a hemocytometer and diluted with cell culture medium to a final concentration of $5 \times 10^5$ cells per ml. A 100 μl aliquot of that cell suspension was added to the nylon fabric disk and the cells were allowed to grow on the nylon for 2 days prior to placement onto the CAM. The nylon fabric disks were then gently dipped into PBS prior to placement onto the CAMs of 8-day-old chick embryos. After 4, 6 and 8 days post-placement of the nylon fabric disks, the CAMs were fixed in situ and the resulting specimens were processed as described above for evaluation of gross morphology and histology.

Figures 14A, 14B, 14C, 14D, 14E, 14F, 14G, 14H, 14I, 14J, 14K, 14L:
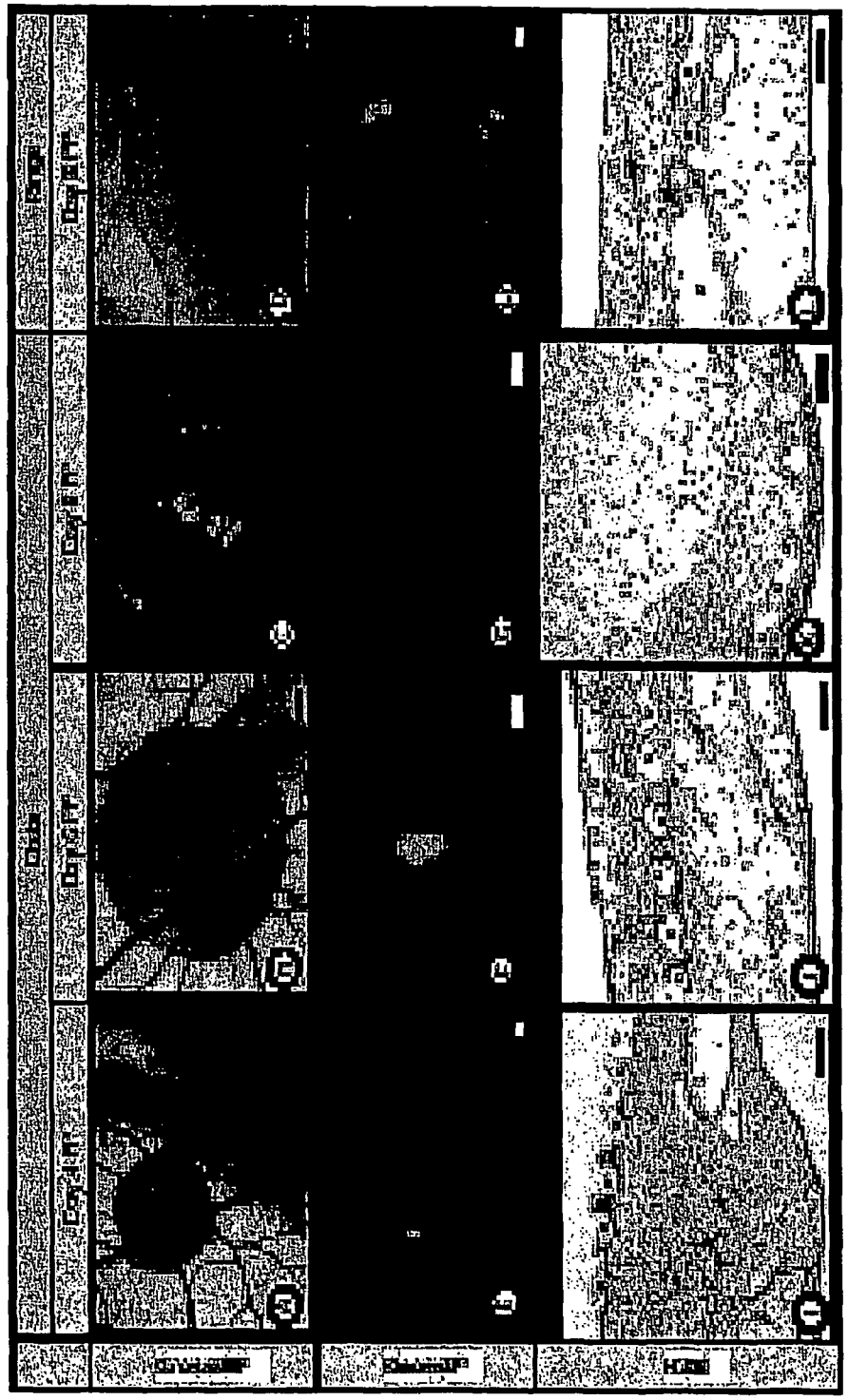
FIGS. 14A-14D respectively show the gross views, under bright field microscopy, of GFP:DF-1 cells grown on nylon disks or placed in nylon rings on a chorioallantoic membrane at days 4, 6, and 8 consistent with the present invention.
FIGS. 14E-14H respectively show the gross views, under fluorescent microscopy, of GFP:DF-1 cells grown on nylon disks or placed in nylon rings on a chorioallantoic membrane at days 4, 6, and 8 consistent with the present invention.
FIGS. 14I-14L respectively show the histologic views of GFP:DF-1 cells grown on nylon disks or placed in nylon rings on a chorioallantoic membrane at days 4, 6, and 8 consistent with the present invention.

Since neither direct placement of viral vector alone nor genetically engineered cells alone placed onto the CAM, were able to significantly infect the CAM, a cell based viral vector nylon delivery system was experimentally developed. Initially utilized was the GFP-RCAS system to rapidly evaluate gene transfer protocols for the CAM model. In order to maximize GFP:DF-1 cell delivery/GFP expression to the CAMs, as well as directly mark the tissue site of cell implantation, a nylon fabric was utilized as both a cell carrier/support system, as well as a marker system, to track the site of cell transfer onto the CAM. For these studies in vitro cultured cells were grown on small circles of nylon fabric ("Disks") and transferred those to the ex ova CAM membrane. FIG. 13A demonstrates the brightfield image of GFP:DF-1 cells grown on nylon disks and placed onto the CAM at time point 0. FIG. 13B demonstrates the fluorescent image of GFP:DF-1 cells as the representing cell line to show the ability of DF-1 cells to grow on nylon fabric. This study demonstrated that the DF-1 cell line is able to grow on the nylon fabric. With reference to FIG. 14, it was also demonstrated that GFP:DF-1 cells grown on the nylon disks have the ability to infect the CAM tissue. It appears by comparing the brightfield images of the gross pictures shown in FIG. 14A-14C with the matching fluorescent images of the nylon disks shown in FIG. 14E-14G that only the CAM tissue growing on top of the nylon fabric is infected and as such expresses GFP. It should be noted that there was no difference in the chick development, morbidity or mortality rates in untreated control chick embryos when compared to embryos treated with media only, DF-1 cells and GFP:DF-1 cells producing GFP.

One embodiment of the present invention includes an alternative approach of adding the various cell lines directly onto the CAM. Experimentally nylon fabric was cut into rings, with an inner diameter of 7 mm, wherein the nylon fabric was utilized as a marker for the cell application site on the CAM. Confluent monolayers of the various cell lines were processed as described above and added into the nylon ring. Additionally, the nylon ring was dip-coated in egg white prior to placement onto the CAM. After 8 days post-placement of the nylon rings, the CAMs were fixed in situ and the resulting specimens were processed as described above for evaluation of gross morphology and histology. This study demonstrated that the DF-1 cells line is able to grow around nylon rings. The fluorescent ring seen in GFP:DF-1 nylon fabrics is a result of cells accumulating at the edge of the inner ring as shown in FIG. 14H. FIG. 14D is the matching brightfield image to FIG. 14H. FIGS. 14I-14L demonstrate the histology (H&E) of the nylon disks at time points 4, 6, and 8 days post-placement (PP) and nylon rings at day 8 PP. FIG. 14L demonstrates the histology (H&E) of nylon rings at day 8 post-placement (PP). No histologic abnormality could be detected for any of the various time-points.

One enbodiment of the present invention includes the use of genetically engineered VEGF:DF-1 cell systems for delivery of genes in the Ex Ova model utilizing a nylon disk. Experimentally, the effect of mVEGF expression in the ex ova CAM model was investigated by placing mVEGF:DF-1 cells directly on the CAM. As shown in the gross pictures of FIGS. 15B to 15D, the use of nylon disks containing mVEGF-secreting DF-1 cells resulted in a massive growth of vessels within the nylon fabric, which can be seen as early as 4 days PP. On day 4 PP an increase in the number of blood vessels in the stroma surrounding the ectoderm was seen histologically as shown in FIG. 15F. The expansion of the vasculature continued rapidly, and, by day 6 PP parts of the entire stroma were covered with capillaries as shown in FIG. 15G. By day 8 PP, the entire stroma was filled with capillaries, pushing the nylon fabric towards the endoderm as shown in FIG. 15H. It should be noted that unlike mammalian red blood cells, avian red blood cells are nucleated and thus, can be mistaken for leukocytes. As controls for these studies, uninfected DF-1, AS-mVEGF or RCAS-GFP infected DF-1 cells were added to the CAMs. None of these control cells caused significant increase in blood vessel formation in the CAM. "Nylon-only" (i.e. nylon disks without any cells) controls were also utilized on the CAMs, which also did not induce new blood vessel formation. FIG. 15A shows a gross appearance of control CAMs and FIG. 15E shows a histology of control CAMs. It should be noted that the empty spaces in the histologic sections are where nylon fabric fibers, designed as N in FIGS. 15E to 15H and 16C and 16D, have fallen out of the tissue sections. This experimental study shows a method of implanting GE cells which produce VEGF which are attached to biomaterials (Nylon), in a in vivo model ex ova CAM) these GE cells can induce neovascularization at the sites of implantation, and also demonstrates the important of attachment of the cells for successful gene therapy One embodiment of the present invention includes the use of genetically engineered VEGF:DF-1 cell systems for delivery of genes in the Ex Ova model utilizing nylon rings. Experimentally nylon fabric was cut into rings, with an inner diameter of 7 mm, and utilized as a marker for the cell application site on the CAM. The cell addition to the nylon rings utilizing the RCAS-mVEGF construct showed a ring of neovascularization at the edge of the inner circle, which is a result of cells accumulating at the edge of the inner circle, as demonstrated earlier by the use of GFP:DF-1 cells as shown in FIG. 16B. In contrast, control cell addition failed to induce neovascularization as shown in FIG. 16A. FIGS. 16C and 16D show the histology of the nylon rings. As can be seen, an intensive capillary development is the case for only the mVEGF:DF-1 cells but not for the control. As discussed earlier, avian red blood cells are nucleated cells with red cytoplasm and should not be confused with leukocytes. Thus, it is experimentally established a simple, safe and efficient viral vector-cell delivery system for gene transfer in the ex ova CAM model. In addition, this experimental data clearly demonstrates that the RCAS-mVEGF model can induce new vessel formation in the ex ova CAM model. This experimental study shows another method for adding genetically engineered cells to biomaterials, for example nylon disks, which can be used to enhance gene therapy, gene transfer, in vivo using the ex ova CAM model. It also shows how to evaluate the results of the gene therapy and demonstrates the evaluation of cellular attachment in determining successful gene therapy.

One embodiment of the present invention includes mVEGF Expression in Vivo. As previously shown experimentally the in vitro studies demonstrated that the mVEGF:DF-1 cells produced mVEGF. In vivo expression of mVEGF in the CAM model was also experimentally carried out. For these experiments, media, mVEGF:DF-1 cells or control cells (DF-1, GFP:DF-1 and mVEGF antisense:DF-1 cells) treated CAMs were prepared using the nylon ring system as described above. At day 8 post implantation the nylon rings were removed from the CAMs and the nylon ring associated CAM tissue was removed and homogenized using a glass homogenizer and a 0.1% triton PBS buffer to enhance protein extraction. The resulting homogenates were clarified by centrifugation, assayed for mVEGF content by ELISA and for protein content by BCA protein assay (Pierce Chemical Company). All CAM data was normalized by calculation of pg of mVEGF per mg of total protein. This experimental study shows a method for the evaluation of the expression of a gene, for example, a mouse gene (VEGF) in a biological model, for example, the Chicken Ex ova CAM model.

Analysis of the CAM tissue homogenates demonstrated that CAM tissue from the mVEGF:DF-1 treated CAMs had significant mVEGF content (137.6 ±3.67 pgs of mVEGF per mg total protein), that none of the CAM tissue from media or control DF-1 cells (DF-1, mVEGF antisense:DF-1 or GFP:DF-1 Cells) had detectable mVEGF in the tissue homogenates. It should be noted that the ELISA detected only mouse mVEGF and not chicken mVEGF. Thus, these experimental studies are evaluating only the murine VEGF gene product expressed in DF-1 cells by gene transfer and show that the mouse VEGF gene that was inside the genetically engineered cells used for this experimental gene therapy to induce new blood vessel was expressed in vivo in the chicken CAM, and that its expression was only seen when there was new blood vessel formation.

One embodiment of the present invention includes the use of fibrin for the delivery of genes in the Ex Ova model. After experimentally showing that fibrin clots are not only able to entrap cells but also to release the virus, as discussed above, the effect of neovascularization of VEGF:DF-1 cells entrapped in a fibrin clot in the ex ova chick model was determined. For this experimental study, VEGF:DF-1 cells or control cells (DF-1, GFP:DF-1 and AS-VEGF:DF-1) (2 million cells/ml) were mixed with equal amounts of a physiological Fibrinogen (Fg) solution (3 mg/ml) and a 50 µl aliquot was placed onto a nylon. After 5µl of a 2.5E-3 U/µl thrombin solution (Sigma Chemical, St. Louis, Mo.) was added directly onto the Fg/cell-nylon or Fg/media-nylon mixture, the various nylon-disks were placed in a tissue culture incubator for about 15 minutes at 37° C. for polymerization of the fibrin to occur. Disks were lifted out of the petri-dish, and care was taken to make sure most of the fibrin clot entrapping the cells or media was still attached to the nylon. The fibrin clot was then placed with the fibrin site down on top of the CAM of an 8-day old chicken embryo. Thus, it was experimentally shown how to make an ATS which includes a matrix material and includes genetically engineered cell(s). Also shown is how the ATS can be used in conjunction with a biomaterial support for such things a gene therapy, for example, for the induction of new blood vessels in vivo in the ex ova CAM model system.

As can be seen in the gross pictures of FIGS. 17B to 17D, the use of fibrin matrix containing mVEGF-secreting DF-1 cells resulted in a massive growth of vessels within the nylon fabric, which can be seen as early as 4 days PP. Control cells DF-1 as shown in FIG. 17A did not induce any neovascularization on the CAM (data not shown for GFP:DF-1 and AS-VEGF:DF-1). These experimental results show that an ATS which includes, for example, a genetically engineered cell with a matrix material such as fibrin may be used in conjunction with a biomaterial support, such as nylon, to modify biological tissues, such as new blood vessel formation in vitro.

One embodiment of the present invention includes the fabrication and utilization of Loop-Type Chemical Sensor. Experimentally, a chemical, acetaminophen, sensor, as shown in FIGS. 18A and 18B was formed from a Teflon™ coated platinum (Pt) wire (Medwire, Mt. Vernon, N.Y.) which was coiled around a 13G needle after the Teflon™ had been removed at the wire extremities. The coiling area served as the working electrode for the acetaminophen sensor. The coiled Pt wire was then anodized at 1.9 V and cycled between −0.26 and +1.1 V vs a saturated calomel electrode and with a Pt wire (Alfa Aesar, Ward Hill, Mass.) counter electrode in 0.5 M $H_2SO_4$ utilizing a CV-27 potentiostat (Bioanalytical Systems, West Lafayette, Ind.). Next, electrodeposition of a poly(o-phenylenediamine) (PPD) (Sigma Chemical, St. Louis, Mo.) film was conducted at +0.65 V for 10 minutes. The sensor was dried for 0.5 h at room temperature before dip coating the sensors with 6 layers of Nafion® fluoropolymer-copolymer (Sigma Chemical, St. Louis, Mo.). Sensors were cured for 0.5h at 120° C. and stored dry at room temperature in closed containers. PPD film formation and Nafion® fluoropolymer-copolymer coating were utilized since they are known to prevent or reduce biosensor fouling.

The performance of the sensor was evaluated in vitro as shown in FIGS. 18C and 18D. Based on, for example, the nylon ring data, a circular sensor was chosen since it Would act as a "corral"for the mVEGF:DF-1 when added to the sensor placed on the CAM. The acetaminophen sensor performance in vitro demonstrated that the sensor showed a dose depend response to acetaminophen over a range of 0.5 to 8 mM acetaminophen as shown in FIG.18C. The slope for the response of the acetaminophen sensors was 644 nA/mM, with an intercept of 390 nA ($R^2=0.988$). The ex ova CAM model with an acetaminophen sensor in place at day 9 post-sensor placement is presented in FIG. 18D. These in vitro studies demonstrated the functionality and sensitivity of our sensor in vitro. This study also shows how to assemble an ATS-sensor combination wherein the ATS includes a genetically engineered cell in addition to showing how to deploy the ATS-sensor in vitro implantation and testing of function/lifespan in a biological model, for example, the ex ova CAM model.

One embodiment of the present invention includes preparation sensor-Cell-Placement on CAM. Experimentally, after sterilizing the sensors by, for example, overnight UV exposure, sensors were dip-coated in egg-white (EW) to enhance cell attachment. The sensors were placed into a 60×15 mm tissue culture treated petri-dish and after the EW was dried out, a fibrin clot containing either media or the cell suspensions (mVEGF:DF-1 or GFP:DF-1) was formed on top of the sensor loop. The formation of fibrin clots served as a matrix material to keep the cells localized around the sensor. Briefly, equal amounts of human fibrinogen (6 mg/ml; Sigma Chemical, St. Louis, Mo.) and cell suspension (2 million cells/ml) or media were mixed and a 50 µl aliquot was placed onto the sensor loop. 5 µl of a 2.5E-3 U/µl thrombin solution (Sigma Chemical, St. Louis, Mo.) was added directly onto the fibrinogen/cell or fibrinogen/media mixture. Polymerization was complete within 15 minutes at 37° C. and produced a three-dimensional gel of fibrin entrapping cells and sensor or culture media and sensor. Sensors were lifted out of the petri-dish, and care was taken to make sure most of the fibrin clot entrapping the cells was still attached to the sensor. The sensor was then placed on top of the CAM of an 8-day old chicken embryo.

Sensor performance in vivo was conducted 6 to 10 days post-placement of the sensor using the three-electrode system described above. The petri-dish containing the developing chicken embryo was placed into a sand box, which was kept at 38° C. and a potential of 700 mV was applied to the working electrode. After stabilization of the background current, 200 µl of a 50 mM acetaminophen solution (in PBS) was injected i.v. and the sensitivity to acetaminophen was determined and recorded onto a chart recorder (Bioanalytical Systems (BAS), West Lafayette, Ind.). The sensor current was monitored for approximately 20 minutes before another i.v. injection of acetaminophen was performed. Sensor response to acetaminophen was calculated as nano Amperes (nA) of the initial current increase. Thus, a method was experimentally shown for evaluating the function of a chemical sensor, for example an acetaminophen sensor and for evaluation an ATS-sensor combination, wherein the ATS contains genetically engineered cell(s) and a matrix material such as fibrin.

Figure 19B:
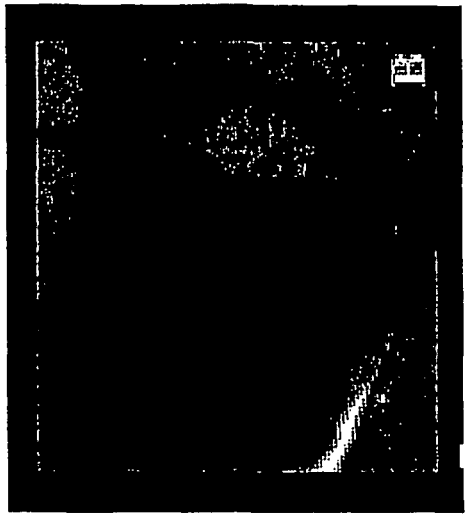
FIGS. 19B and 19D respectively show a chemical sensor incorporated in an ex ova chorioallantoic membrane model and the associated sensor response graph consistent with the present invention.
Figure 19D:
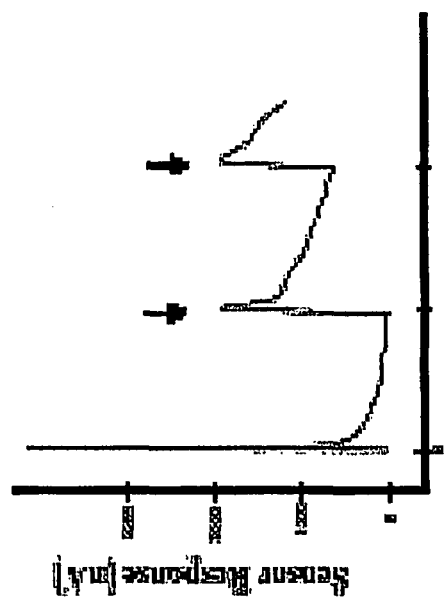
Figure 19A:
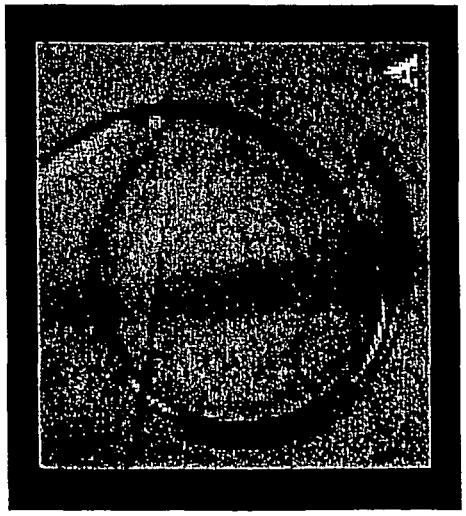
FIGS. 19A and 19C respectively show a chemical sensor incorporated in an ex ova chorioallantoic membrane model and the associated sensor response graph consistent with the present invention.
Figure 19C:
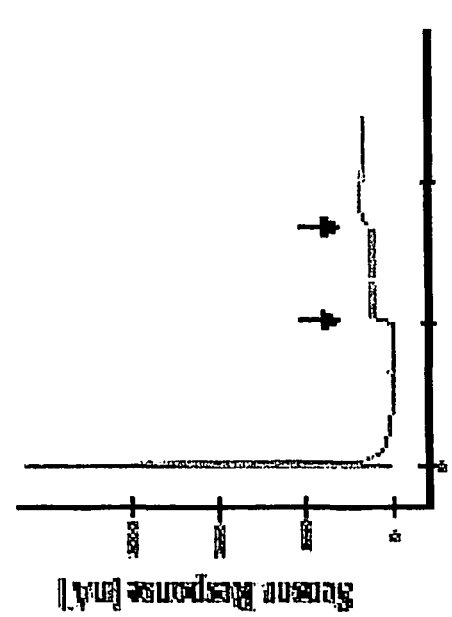
Figure 20:
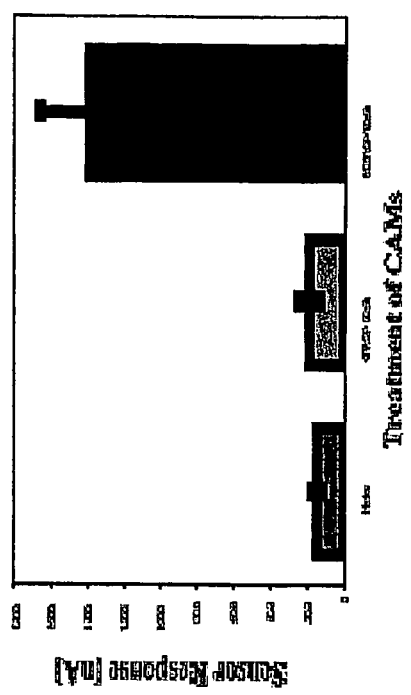
FIG. 20 is a graph quantifying an acetaminophen sensor response in an ex ova chorioallantoic membrane model consistent with the present invention.

Impact of mVEGF Gene Transfer on Loop-Type Sensor Function in Vivo was then demonstrated experimentally. The focus of this experimental study was to: 1) demonstrate the in vivo function of the acetaminophen sensors, and 2) to determine the impact of mVEGF induced increase of vessel density surrounding the sensor on sensor function in vivo. In general, sensors were incorporated after only a few days post-placement and only sensors completely incorporated were finally utilized to compare responses between control sensors and angiogenesis induced around sensor. After 6-days to 10-days post-placement, sensors were tested using the 3 electrode system described in the methods section above. Sensors implanted on CAMs with buffer or GFP:DF-1 cells displayed no induced neovascularization around the sensor as shown in FIG. 19. In addition, minimal sensor responses to i.v. acetaminophen injection were determined as shown in FIG. 20 wherein the results were media: 133.33 ±27.64 nA (n=6); GFP:DF-1: 187.50±55.43 nA (n=6). In addition, it was observed that the sensors implanted with mVEGF:DF-1 cells displayed massive neovascularization as shown in FIG. 19B. Also observed was a massive sensor response to i.v. injected acetaminophen as shown in FIG. 20 wherein the mVEGF:DF-1 results were 1387.50±276.42 nA (n=6)). Statistical analysis indicated that there was no statistical difference in sensor response between media treated sensors and sensors treated with GFP:DF-1 cells. However, when the responses of media treated sensors or GFP:DF-1 treated sensors where compared to mVEGF:DF-1 treated sensors there was major statistical significance ($p<0.001$). As experimentally has been shown, the VEGF-GE-Cell-ATS dramatically enhanced the in vivo function of the Chemical sensor in vivo, with the dramatic increase in sensor function being associated with the massive neovascularization that occurred only at the site of the VEGF-GE-Cell-ATS-sensor implantation. Thus, ATS with genetic engineered cell(s) and matrix material such as Fibrin enhance both neovascularization and sensor function at sites of ATS-sensor implantation.

Figure 21:
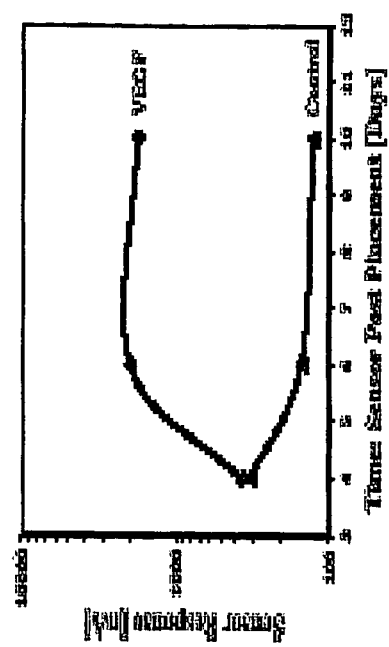
FIG. 21 is graph of the impact of mVEGF:DF-1 cell induced neovascularization on an acetaminophen sensor response in an ex ova chorioallantoic membrane model consistent with the present invention.

Sensor function in the mVEGF:DF-1 and GFP:DF-1 treated sensor-CAM studies were then compared over time as shown in FIG. 21. The control, GFP:DF-1 treated, sensors were functional at day 4 post-implantation but rapidly lost function by day 6 post-implantation as shown in the FIG. 21 graph of control GFP:DF-1. This loss of sensor in the ex ova CAM model generally paralleled the loss to sensor function seen in a wide variety of mammalian models of implantable sensors. In contrast, the mVEGF:DF-1 treated sensors were functionally similar to control GFP:DF-1 treated sensors at day 4, but by day 6 post placement, displayed a massive increase in function, as shown in the FIG. 21 graph of the mVEGF:DF-1 treated sensors. This increased function correlated with the appearance of neovascularization around the sensor as shown in FIG. 19B. Clearly, increased vessel density surrounding a sensor in vivo does enhance sensor function in vivo, and provide "proof of principle" that gene transfer of angiogenic factors such as mVEGF can be used to enhance vessel density around implanted glucose sensors. Therefore, is has been experimentally shown that while a control, having a normal or non VEGF GE-cell containing ATS, will rapidly lose sensor functionally when implanted in vivo, a genetically engineered cell, such as a VEGF-GE-cell contained in the ATS along with a chemical sensor will not lose function and will even increase its function for sustained periods of time in vivo.

Fabrication of Chemical Needle-Type Sensor is included in one embodiment of the present invention. Experimentally sensor fabrication of an acetaminophen sensor was performed wherein, the sensor comprising a Teflon™ coated platinum (Pt) wire (Medwire, Mt. Vernon, N.Y.), was coiled after the Teflon™ had been removed at its extremities. The coiling area served as the working electrode for the acetaminophen sensor. The coiled Pt wire was then anodized at 1.9 V and cycled between −0.26 and +1.1 V vs. a saturated calomel electrode and with a Pt foil (52 mesh, Alfa Aesar, Ward Hill, Mass.) counter electrode in 0.5 M $H_2SO_4$ utilizing a CV-27 potentiostat (Bioanalytical Systems, West Lafayette, Ind.). Next, electrodeposition of a poly(o-phenylenediamine) (PPD) (Sigma Chemical, St. Louis, Mo.) film was conducted at +0.65 V for 10 minutes. The sensor was dried for 0.5 h at room temperature before dip coating the sensors with 6 layers of Nafion® fluoropolymer-copolymer (Sigma Chemical, St. Louis, Mo.). Sensors were cured for 0.5 h at 120° C. and stored dry at room temperature in closed containers. PPD film formation and Nafion® fluoropolymer-copolymer coating were utilized to reduce or prevent biosensor fouling.

Figure 23:
FIG. 23 is a needle type acetaminophen sensor consistent with the present invention.

Prior to use of the acetaminophen needle-type sensor in vivo the sensor performance was evaluated in vitro. The needle sensor configuration was used since it resembles the same configuration as used for the glucose sensor discussed below. FIG. 23 shows the design of the acetaminophen needle-type sensor. Briefly, acetaminophen sensor, working electrode, was characterized in pH 7.4 phosphate buffered saline at 0.7 V vs. a small reference electrode (World Precision Instruments, Sarasota, Fla.) and utilizing a Pt foil as the counter electrode. The background current was allowed to stabilize for about 20 to 30 minutes, and increasing amounts of acetaminophen solution (Sigma Chemical, St. Louis, Mo.) were added to examine sensitivity and linearity. The acetaminophen sensor performance in vitro demonstrated that the sensor showed a dose depend response to acetaminophen over a range of 0.5 to 8 mM acetaminophen. The slope for the response of the acetaminophen sensors was 94 nA/mM, with an intercept of 57 nA ($R^2$=0.991). These in vitro studies demonstrated the functionality and sensitivity of our sensor in vitro, and thus allowed us to utilize these sensors for our in vivo studies, i.e. in the ex ova CAM model.

Enhancing Acetaminophen Sensor Function Using Genetically Engineered Cells-Matrigel™-Systems to Induce Neovascularization in the Ex Ova CAM Model is included in one embodiment of the present invention. Experimental studies were conducted to determine the impact of mVEGF induced increase of vessel density surrounding the sensor on needle-type chemical sensor function in vivo. Briefly, needle-type acetaminophen sensors were prepared and processed as described above. Acetaminophen sensors were placed into a microcentrifuge tube containing 40 μl of a suspension of Matrigel™ and cells at a ratio of 6:4 (15-20E4 cells per tube). Cells were submerged in cell DMEM media containing 10% fetal bovine serum. Sensors were carefully taken out of the Matrigel™/cell-media suspension or Matrigel™/media suspension to make sure that most of the suspension remains on the sensor. Sensors were then placed on top of 7 or 8 day old chicken embryo and tested for functionality once incorporated into the tissue. An additional 30 μl of Matrigel™ and cell suspension or media only was placed on top of acetaminophen sensor once placed onto the CAM. In general, sensors were incorporated after only a few days post-placement and only sensors completely incorporated were finally utilized to compare responses between control sensors and angiogenesis induced around sensor.

Figure 24:
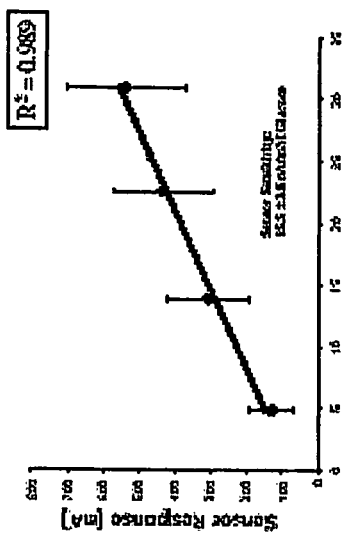
FIG. 24 is a graph of a needle type acetaminophen sensor consistent with the present invention.

FIG. 24 shows a summary of the in vivo acetaminophen sensor studies performed at 7 to 10 days post placement of the sensors onto the CAM. Sensors implanted on CAMs with mix of Matrigel™ and media (Media) or control cells (DF-1 or GFP:DF-1) displayed no induced neovascularization around the sensor and had minimal sensor responses to intravenous dextrose injection as shown in FIG. 24 wherein the result were Media, 16±14 nA (n=5); DF-1, 64±26 nA (n=5); GFP:DF-1 62±19 nA (n=5). In contrast, the sensors implanted with mVEGF:DF-1 cells displayed massive neovascularization, and equally massive sensor response to intravenously injected dextrose as shown in FIG. 24 wherein the results for VEGF:DF-1 was 293±21 nA (n=3). These studies clearly demonstrate that the uses of the VEGF-Matrigel™ system described here can dramatically enhance the function and lifespan of a chemical sensor, for example, an acetaminophen sensor in vivo.

Figure 25:
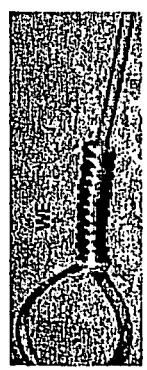
FIG. 25 is a photomicrograph of a glucose sensor with a reference electrode and a working electrode consistent with the present invention.

One embodiment of the present invention includes the fabrication of a biosensor, for example, a glucose sensor. Experimentally a needle-type glucose sensor, as shown in FIG. 25, having an outer diameter of 0.5 mm was constructed from a platinum (Pt) wire and a silver (Ag) wire, with the Teflon™ coating having been removed from the wire ends. The Pt wire was coiled 10 times around the insulating Pt wire and served as the working electrode. The Ag reference electrode wire was coiled approximately 15 times around the Pt wire distal from the coiled Pt wire with a 2 mm cap between them. After the probe was sonicated in water for 5 min, silver chloride was then formed on the Ag wire electronically by applying a current of 0.04 mA in a stirred 0.1 N HCl solution for 60 minutes. Anodization and PPD film formation of the working electrode was performed as described for the acetaminophen sensors. Glucose oxidase (GOD) (EC 1.1.3.4, from *Aspergillus niger*, 158 U/mg) was immobilized using glutaraldehyde (aqueous 25%) as a cross-linking agent and bovine serum albumin as a carrier protein. 1 μl of that mixture was applied three times to the working electrode with a break of 30 minutes between the single dipping procedures to allow the solution to dry on the surfaces {Abel, 1999 #524}. After dip-coating the sensors with 6 layers of Nafion® fluoropolymer-copolymer, the sensors were cured for 0.5 hrs at 120° C. and stored dry at room temperature in closed containers. All chemical reagents were obtained from Sigma, St. Louis, Mo.

Figure 26:
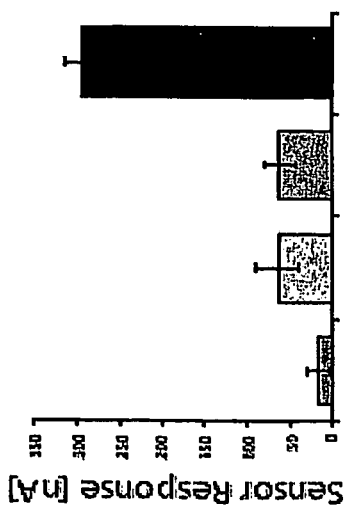
FIG. 26 is a graph of a glucose sensor response in vivo consistent with the present invention.

The in vitro sensitivity of each sensor to glucose was determined in phosphate buffered saline (PBS) by applying a potential of 700 mV versus Ag/AgCl. After stabilization of the background current, glucose was added stepwise (final concentrations: 0, 4.8, 13.9, 22.6 and 30.9 mM) in order to assess sensitivity and linearity. All testing was carried out at 37° C. Sensor output was measured at multiple glucose levels in order to assess linearity. The sensor responds linearly to glucose concentration from 5 to 31 mmol/l (from 86 to 556 mg/dl). A typical example of the sensor response to increases in glucose concentration in vitro is shown in FIG. 26 with a sensitivity of 15.5±3.8 nA/mM (n=38). These in vitro studies clearly demonstrated the functionality and sensitivity of the sensor in vitro, and thus allowed these sensors to be used for in vivo studies using the ex ova model.

In order to assess if Matrigel™ affects glucose sensor functionality in vitro, sensors were tested with and without the matrix material Matrigel™. Briefly, Nafion® fluoropolymer-copolymer needle sensors (outer diameter of 0.5 mm) were fabricated and validated as previously described. In vitro sensitivity of each sensor to glucose was determined in phosphate buffered saline (PBS) by applying a potential of 700 mV versus Ag/AgCl. After stabilization of the background current, glucose was added stepwise with final concentrations being 0, 4.8, 13.9, 22.6 and 30.9 mM in order to assess sensitivity and linearity of the sensor response. All testing was carried out at 37° C. Matrigel™ was then added to the working electrode of the glucose sensors and after polymerization of the Matrigel™, the glucose sensors were tested in PBS as described above. Glucose sensor performance in vitro showed that sensors without addition of Matrigel™ responded linearly to glucose concentration from 5 to 31 mmol/l (from 86 to 556 mg/dl). Furthermore, addition of Matrigel™ to the working electrode of glucose sensors did not affect sensor functionality and in some cases appeared to increase sensor sensitivity. These sensors had an average sensitivity of 10.6 ±3.2 nA/mM without Matrigel™ addition and an average sensitivity of 10.7±3.5 nA/mM with the addition of Matrigel™ (n=4). These experimental in vitro studies demonstrated that matrix material, for example, Matrigel™ does not affect the functionality and sensitivity of sensors in vitro, and thus allow the sensors to be used in in vivo studies. In addition, these studies identify a method to prepare and validate in vitro, a basement membrane based ATS for implantable glucose sensors and that a basement membrane based ATS does not interfere with the function of a glucose sensor in vitro.

One embodiment of the present invention includes enhancing glucose sensor function using and ATS which includes genetically engineered cells-fibrin-matrix systems to induce neovascularization in an ex ova CAM model. Experimentally Nafion® fluoropolymer-copolymer needle glucose sensors were fabricated, validated, implanted in the ex ova CAM's, and sensor function, as well as blood glucose levels were evaluated at various times after sensor placement. Experimentally determined was whether the VEGF:DF-1 induced increase in vessel density would enhance glucose sensor function in the ex ova CAM Model. GFP:DF-1-fibrin treated sensors, lacking neovascularization, did not respond following an i. v. glucose injection (200 µl of 0.3 M glucose) (FIG. 26B), and the GFP:DF-1-fibrin treated sensor response did not correlate with directly measured blood glucose levels as shown in FIG. 27C. However, when a glucose solution (100 µl of a 0.3 M solution) was injected directly into the tissue surrounding the sensor in the GFP:DF-1 treated CAM's, a high-magnitude signal (250 nA) was obtained, indicating that the implanted sensor was still functional as shown in FIG. 27B. In contrast, the sensors in the VEGF:DF-1-fibrin treated CAM's retained their function , as shown in FIG. 27E, and signals from the neovascularized sensors correlated well with glucose concentration measurements made directly on contemporaneously sampled embryonic blood as shown in FIG. 27F. Thus this experimental example teaches that using a fibrin-VEGF GE cell ATS system enhances the in vivo function of an implantable glucose biosensor in the ex ova CAM model.

Figure 28:
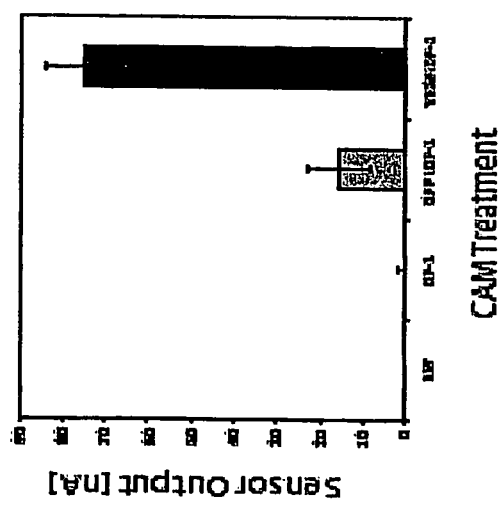
FIG. 28 is a comparative graph of glucose sensor responses using ATS in an ex ova CAM model under various treatments consistent with the present invention.

FIG. 28 shows a summary of the in vivo glucose sensor studies performed at 6 to 9 days post placement of the sensors onto the CAM. Sensors implanted on CAM's with protein coating (EW) (data not shown) or control cells (DF-1 or GFP:DF-1) displayed no induced neovascularization around the sensor and had minimal sensor responses to intravenous dextrose injection, for example, FIG. 28 shows the results for EW, 0±0 nA (n=9); DF-1, 0±0 nA (n=6); GFP:DF-1 15.6±7.7 nA (n=9). In contrast, the sensors implanted with mVEGF:DF-1 cells displayed massive neovascularization as shown in FIG. 27D, and an equally massive sensor response to intravenously injected dextrose as shown in FIG. 28 where the result were mVEGF:DF-1, 75±8.6 nA (n=11). As can be seen in FIG. 28 addition of DF-1 cells to the sensor implantation site resulted in no enhancement of sensor function, when compared to the addition of a protein control (chicken egg white, EW). Addition of GFP:DF-1 cells to sites of glucose sensor implantation caused only a slight increase in sensor function. Addition of VEGF:DF-1 cells to sites of glucose sensor implantation caused a massive and statistically significant increase in glucose sensor response compared do not only EW and control DF-1 cells, but also when compared to the GFP:DF-1 cell treated sensor implantation sites. These studies clearly demonstrate that the uses of the VEGF-fibrin system described here can dramatically enhance glucose sensor function and lifespan in vivo.

At 8-9 days post placement of the sensors, CAM tissue was fixed in situ (10% buffered formalin) and removed. The resulting fixed tissue, including the incorporated glucose sensor, was then processed and embedded in paraffin. Since glucose sensors are composed of silver and platinum wire, removal of the sensor from the CAM tissue, prior to sectioning is required. Therefore, the sensor was carefully removed from the paraffin embedded tissue using fine tip forceps. Generally, removing the sensor from the embedded tissue in a horizontal plane resulted in less tissue destruction. It should be noted that frequently fragments of the outer polymer layers of the sensors remained associated with the embedded tissue. Once the sensor was removed from the paraffin embedded CAM tissue, the paraffin was melted, and the resulting "sensor free" tissue was re-embedded in paraffin. Generally, 5 µm sections were prepared from the various CAM specimens, mounted on glass slides, and stained with hematoxylin-eosin (H&E) or trichrome stain (fibrosis) for evaluation of histopathology. This experimental details an example of a method for processing tissue containing an ATS-glucose sensor.

Figures 29A, 29B, 29C, 29D, 29E, 29F, 29G, 29H:
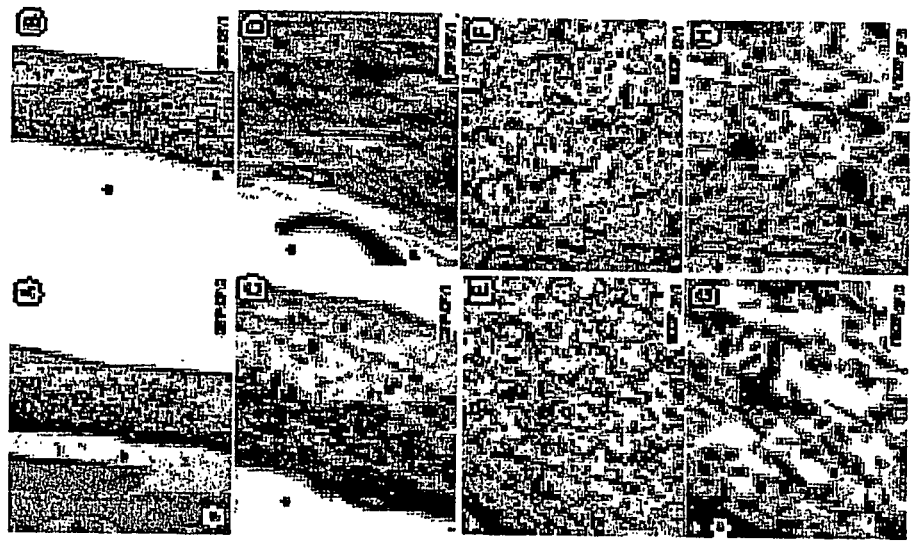
FIGS. 29A-29H show the histopathologic views of tissue reactions induced in ex ova CAM tissue by ATS with GFP:DF-1 and VEGF:DF-1 cells consistent with the present invention.

Experimental histopathologic evaluation of the tissue reactions induced in ex ova CAM tissue by GFP:DF-1 and VEGF:DF-1 fibrin gene delivery systems were then conducted. Histological evaluation of both control (GFP:DF-1) and neovascularized CAM tissue clearly demonstrated that extensive neovascularization occurred only in the VEGF:DF-1 treated CAM's as shown in FIGS. 29A-29H. GFP:DF-1 treated CAM tissue general displayed moderate inflammation, as shown in FIGS. 29A and 29E and fibrosis, as shown in FIGS. 29B and 29F. The histology for protein coating (EW) and DF-1 cells was similar to that of the GFP:DF-1 treated CAM's (data not shown). It should be noted that in the VEGF:DF-1 treated CAM tissue, a variety of leukocytes were seen in association with the extensive neovascularization as shown in FIGS. 29C and 29G. Collagen deposition was also seen in association with the neovascularization as shown in FIGS. 29D and 29H. This experimental example demonstrates that an ATS composed of VEGF-GE cells and basement membrane when implanted in vivo can induce neovascularization.

One embodiment of the present invention includes enhancing glucose sensor function using genetically engineered cells-Matrigel™-Matrix systems to induce neovascularization in the ex ova CAM model. Experimentally the impact on mVEGF induced vessel density on glucose sensor functionality in vivo was determined. Sensors were prepared and processed as described previously. Formation of bio-matrix was similar as described when using fibrin. Briefly, equal amounts of Matrigel™ (BD Biosciences, MA) and cell suspension (DF-1, GFP:DF-1 orVEGF:DF-1) or media were mixed in micro-centrifuge tubes and glucose sensors previously dip coated in egg white were submerged into the Matrigel™/cell mixture. Studies indicated that cell numbers ranging from 1E5-2E5 gave comparable neovascularization, therefore 200,000 cells per site were utilized for the present experimental studies. Matrigel™ polymerization was completed after exposure of the tube and sensor to room temperature for a few minutes. The resulting sensor-Matrigel™-cell clots were released from the micro-centrifuge tube by the addition of 0.9% NaCl, and placed on the CAM's of an 8-day chicken embryo. An additional Matrigel™-cell clot was transferred to the working electrode of the glucose sensor prior to incubation of CAM's at 38° C. and 90% humidity. The Matrige™ served as an ATS matrix material to: 1) preserve cell viability by enhancing cell adherence; 2) enhance cell activation; and 3) to localize cells around the sensor. Sensors without the addition of either cell suspensions or media (EW coating only) served as additional controls. Sensors were incubated for up to 7-10 days post placement of the initially sensor-cell-Matrigel™ mixture. The CAM's were evaluated for gross morphology and sensor function for up to 10 days post placement (day 18 of gestation).

Figure 30:
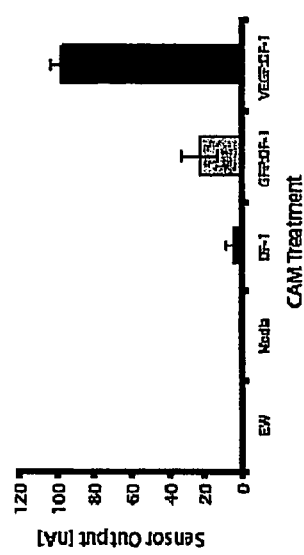
FIG. 30 is a graph of a glucose sensor response for a sensor, which is associated with an ATS having genetically engineered cells consistent with the present invention.

FIG. 30 shows a summary of the in vivo glucose sensor studies performed at 7 to 10 days post placement of the sensors onto the CAM. Sensors implanted on CAM's with protein coating (EW) or control cells (DF-1 or GFP:DF-1) displayed no induced neovascularization around the sensor and had minimal sensor responses to intravenous dextrose injection as shown in FIG. 30 where the results were EW, 0±0 nA (n=6); media, 0±0 nA (n=2); DF-1, 5±4.5 nA (n=6); GFP:DF-1 23.3±10.2 nA (n=6). In contrast, the sensors implanted with mVEGF:DF-1 cells displayed massive neovascularization, and equally massive sensor response to intravenously injected dextrose with the results being mVEGF:DF-1, 97.5±6.0 nA (n=6). As can be seen in FIG. 30 addition of DF-1 cells to the sensor implantation site resulted in a minimal enhancement of sensor function, when compared to the addition of a protein control (chicken egg white, EW). Addition of GFP:DF-1 cells to sites of glucose sensor implantation caused only a slight increase in sensor function. Addition of VEGF:DF-1 cells to sites of glucose sensor implantation caused a massive and statistically significant increase in glucose sensor response compared do not only EW, media and control DF-1 cells, but also when compared to the GFP:DF-1 cell treated sensor implantation sites. These studies clearly demonstrate that the uses of the VEGF-basement membrane (Matrigel™) system described here can dramatically enhance glucose sensor function and lifespan in vivo.

One embodiment of the present invention includes a protocol for the implantation of a glucose sensor into a mammal. Experimentally a murine model of implantable glucose sensors was developed utilizing 35-40 gm ICR mice from Harlan (Indianapolis, Ind.). The mice were shaved at least 24 hr pre-sensor implantation using a Wahl rechargeable electronic shaver. At the time of implantation, the shaved skin was disinfected using 70% isopropyl alcohol. For the present studies only one sensor per mouse was implanted into the interscapular subcutaneous tissue of each mouse. For the sensor implantation the mice were anesthetized with 1% isoflurane as approved by Animal Care at the University of Connecticut, Farmington Conn. Prior to sensor implantation, 0.1-0.150 ml of injectable sterile, pyrogen free, 0.9% NaCl was injected subcutaneously (s.q.) in the head-neck area of the anesthetized mouse to provide an "implantation pocket". This implantation pocket was used to minimize tissue and sensor damage during sensor implantation. Next, a small incision was made in the "implantation pocket" using corneal scissors, and the sensor was then implanted in the s.q. "pocket" with the two sensor leads exposed as shown in FIG. 31. The wound was closed with a drop of Nexaband Veterinary Surgical Glue (Chicago Ill.), and a small polyester mesh was placed on top of the exposed sensor leads as shown in FIG. 31. The sensor leads and the nylon mesh were secured to the shaved mouse skin by applying a coating of "New Skin First Aid and Antiseptic Liquid Bandage" (Medtech Corp, Jackson Wyo.). Mice were kept under anesthesia until the New Skin Liquid Bandage dried. Drying was accelerated with the use of a hair dryer set at low temperature. The use of the nylon mesh and liquid bandage completely prevented removal of the sensors by the mice. Animals were observed until they recovered from anesthesia. Once the sensors were implanted, mice were housed individually, as a precaution to prevent dislodging of the sensor from aggressive behavior between the mice when housed as a group. Daily inspection of the sensor implantation site was necessary to prevent loss of mesh. All mice were maintained under specific pathogen-free (SPF) conditions, at the Animal Facility of the University of Connecticut, Farmington Conn., according to Animal Care Procedures. This experimental example demonstrates how to implant a sensor in the mouse in a fashion to minimize tissue trauma during sensor implantation as well as provide an "in vivo pocket" for depositing ATS, drugs cells etc at the site of sensor implantation also demonstrates the use of super glue to close incision rather that suture thereby minimizing the tissue to the suture. Finally the experimental example demonstrates using nylon mesh and new skin to hold the mesh in place thereby to protecting the sensor leads so they are not dislodged by the mouse, as well as providing antiseptic cover for surgical site of implantation.

Figure 31A:
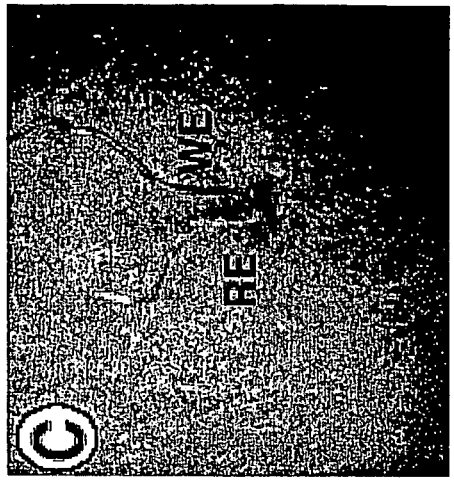
FIGS. 31A-31C show the implantation of a glucose sensor in a mouse.
Figure 31B:
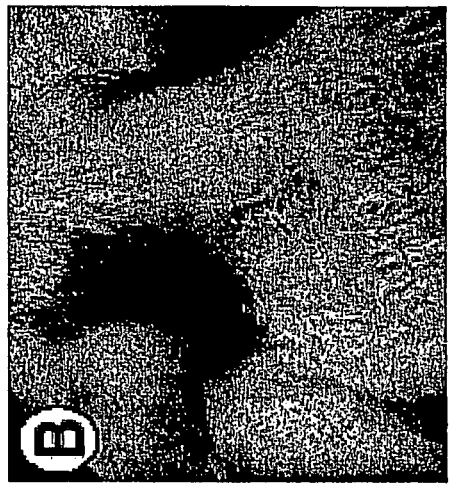
Figure 31C:
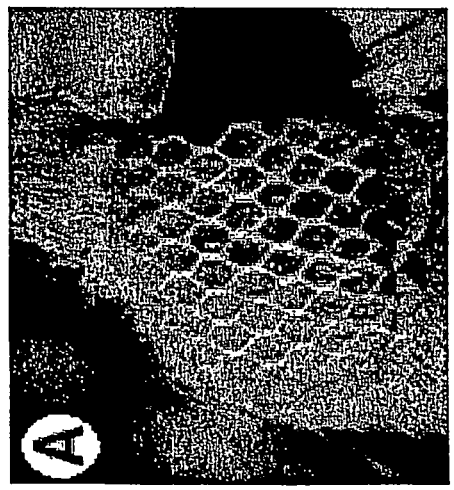

For the development of the murine model of implantable glucose sensors, an amperometric glucose sensor was used, the sensor functions based on the detection of glucose using glucose oxidase. This sensor requires external leads to allow for periodic evaluation of sensor function in vivo. It should be noted that the present invention may include sensors which do not require external leads; for example, sensors having a radio frequency connection to external instruments. Thus, when using a sensor with external leads one of the key factors in the successful development of the implanted glucose sensor model was to develop techniques to maintain placement and sterility of the implanted sensors in the mouse. To address these issues the sensor was implanted in the interscapular region of the neck, which prevented the individual mouse from directly removing the implanted sensor as shown in FIG. 31. Initially, it was found that surgical glue could be used to close the surgical wound at the implantation site, thus eliminating the need for sutures which in themselves cause major tissue reaction as shown in FIG. 31A. Additionally, it was found that utilizing a small nylon mesh to cover the exposed leads of the sensor, and an antiseptic coating polymer, i.e. New Skin®, both adhered the nylon mesh to the mouse skin and provided a sterile antiseptic coating to protect the surgical wound from infection as shown in FIG. 31B. Using this technique there was no damage to the sensor leads by the mouse, and no wound infection was observed as shown in FIG. 31C.

Determination of glucose sensor function in the mouse model was then undertaken. At predetermined time point's post-sensor implantation, sensor function and blood glucose levels were assessed. For these studies animals were anesthetized with 1% isofluorane, and were maintained at 37° C. using a heating blanket. The nylon mesh, and the New Skin® Liquid Bandage were removed with acetone prior to sensor testing. The exposed sensor leads were then connected to a potentiostat (working potential: 700 mV) for amperometric measurements. Current was continuously recorded during the experiment until stable (baseline) current was achieved. To elevate blood glucose levels in these animals they were given 80-150 μl of a 0.5 g/ml dextrose solution intraperitoneally (IP) after establishing sensor baseline period of usually 20 to 30 minutes. To monitor blood glucose levels, a single drop of blood was obtained from the tail vein before glucose injection (baseline) and at 5, 10, and 20 minutes post glucose injection. Further glucose measurements were then made every 10 minutes until the conclusion of the experiment. All blood glucose levels were determined using an OneTouch Ultra® glucose meter (Lifescan, Johnson & Johnson). Sensor performance was followed for about 40 to 60 minutes initially, and for at least 20 to 30 minutes at each subsequent testing session.

In one experimental the glucose sensor function was tested in each mouse immediately following implantation, designated as 1-hour post implantation (HPI), 5 HPI, 1 day post implantation (DPI), 2 DPI, 3 DPI, 7 DPI, 14 DPI and occasionally up to 30 DPI. Between the sensor function tests, the mice were left unrestrained in their cages, without polarization of the sensor. A total of 24 mice were tested, each implanted with a different sensor. Sensor sensitivity was calculated by a two-point calibration wherein one point was taken at baseline and one point was taken at the peak glucose.

Figure 32:
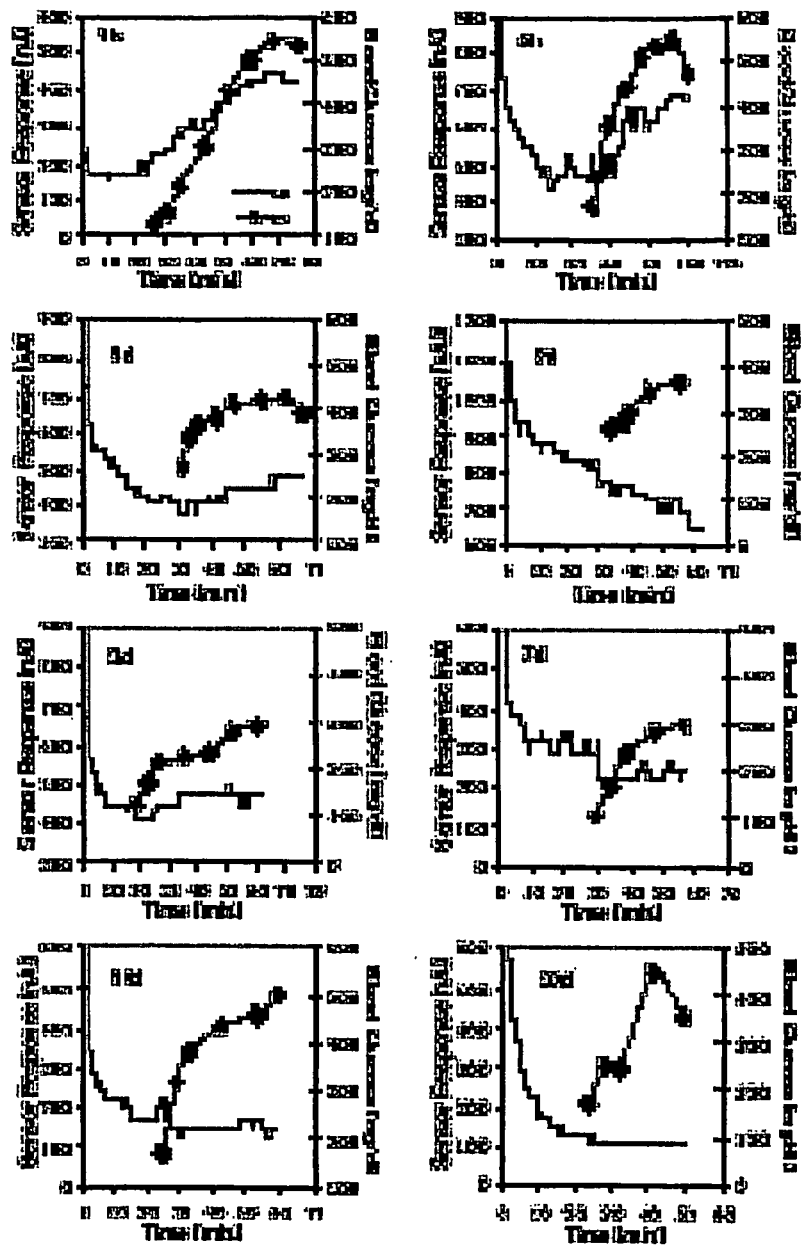
FIG. 32 show various graphs associated with the simultaneous monitoring of a subcutaneous sensor and blood glucose over a 30 day period consistent with the present invention.
Figure 33:
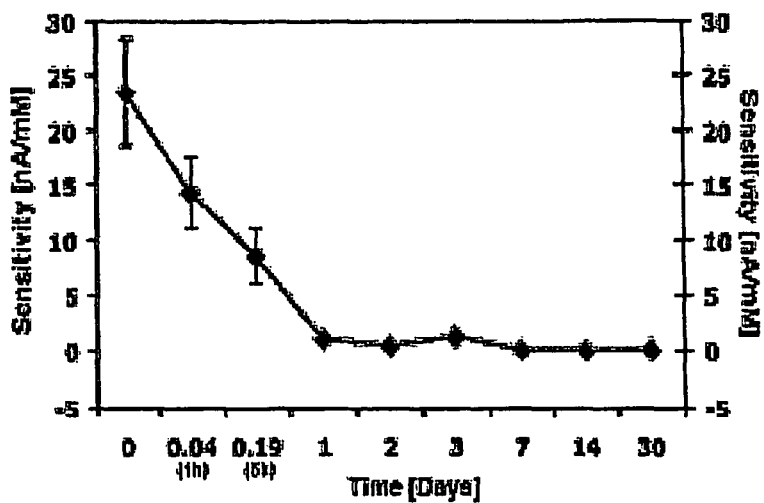
FIG. 33 is a graph showing the mean loss of sensitivity for a sensor.
Figure 34:
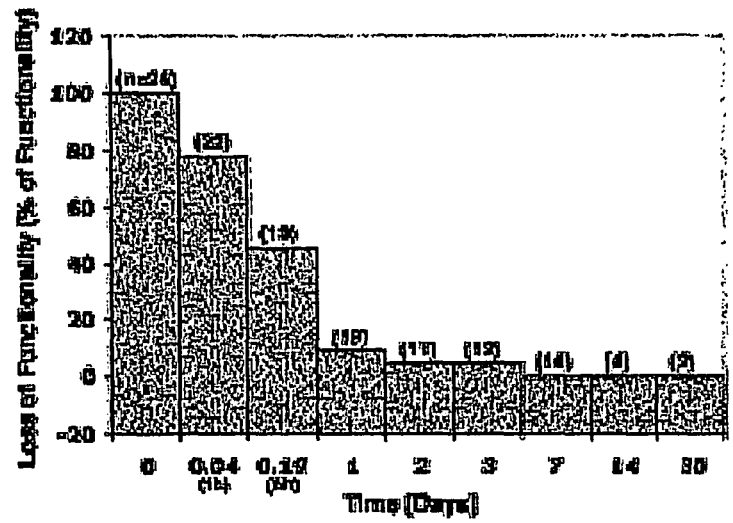
FIG. 34 is a graph showing sensor functionality loss in vivo.

To experimentally evaluate sensor function in the mouse model, sensor function in the mouse was analyzed for 1 HPI and up to 30 DPI. In these studies, glucose blood levels parallel sensor function at both 1 and 5 hours post sensor implantation as shown in FIG. 32 where the results are shown for 1 hr and 5 hr. Analysis of blood glucose and sensor function at 1-day post sensor implantation clearly indicated that although the blood glucose levels were elevated by i. p. injection of the glucose, that there was little or no response from the implanted sensors as shown in FIG. 32 at the 1$d$ point. Analysis of the blood glucose and sensor function at 2, 3, 7, 14 and 30 days post sensor implantation consistently demonstrated that although blood glucose levels were elevated by i. p. injection of glucose, there was no sensor function as shown in FIG. 32 at the 2$d$, 3$d$, 7$d$, 14$d$, and 30$d$ points. This rapid loss of sensor sensitivity, as shown in FIG. 33, and the loss of sensor function, as shown in FIG. 34, within the first day post implantation was seen in this sensor implant arrangement in the mouse model. This loss of sensor function is highly correlated to the general pattern of loss of sensitivity and sensor function seen in other animal models and in man. For example, this experimentally shows that the loss of sensor function seen in mice is similar to the loss of glucose sensor function seen when glucose sensors are implanted into human skin.

Sites of sensor implantation were evaluated grossly for redness, swelling, warmth or other signs of inflammation both before and after removal of the protective nylon mesh. To evaluate the tissue responses to implantation of the glucose sensor at various time points, individual mice were euthanized, and tissue containing the implanted sensors was removed and fixed in 10% buffered formalin. Next, the buffered formalin fixed tissue was then paraffin embedded. Prior to sectioning the embedded tissue, the sensor was removed from the paraffin embedded tissue. Removing the sensor, while it was embedded in the paraffin, resulted in minimum tissue damage as a result of sensor removal. After removal of the sensor, the tissue was re-embedded, and processed for sectioning in a manner similar to that described in the CAM model. The resulting tissue sections were processed using hematoxylin and eosin (H&E), as well as trichrome staining techniques. Histopathologic evaluation of tissue reactions at sites of sensor implantation was done on mouse specimens obtained at 1 day, 3 days, 7 days, 14 days, and 1-month post implantation of the glucose sensor. The tissues from the sites of sensor implantation were examined for evidence of loss of cell and tissue architecture, acute and chronic inflammation including giant cell formation, necrosis, as well as fibrosis and vessel regression.

A determination of the acute and chronic tissue responses to the implanted glucose sensors in the mouse model was also undertaken. The nature of the tissue reactions induced in the mouse by the implanted glucose sensors was determined, by analyzing tissue specimens obtained from sites of sensor implantation at the 1 day to 30 days post sensor implantation. The analysis focused primarily on the tissue reactions surrounding the working electrode (WE) (which contains glucose oxidase) and the reference electrode (RE), which lacks glucose oxidase but does release silver chloride, for example, as shown in FIG. 25. The "bridge" wire between the WE and RE displayed significantly less tissue reaction when compared to the highly tissue reactive reactive WE and the moderately tissue reactive RE.

Figures 35A, 35P:
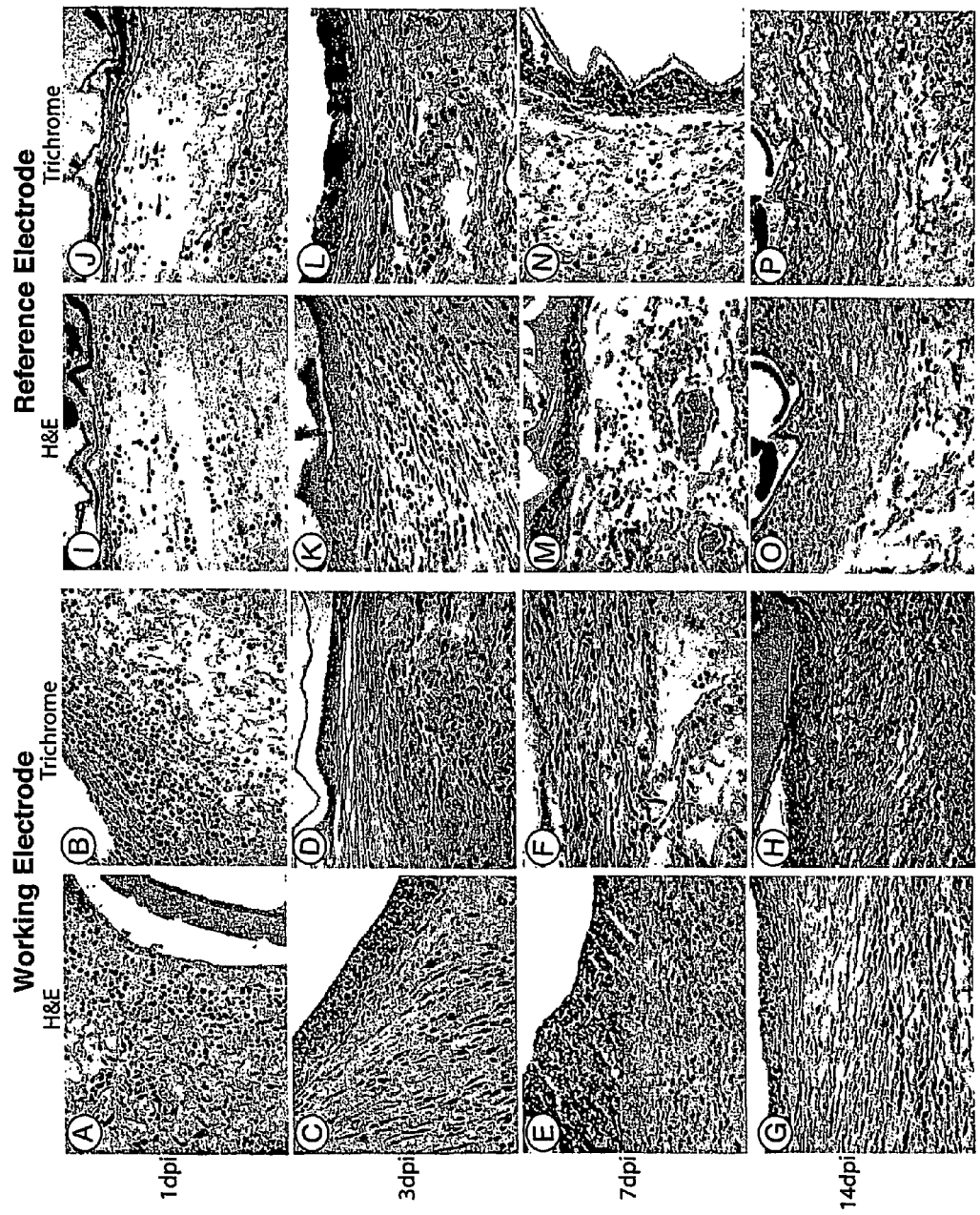
FIGS. 35A, C, E, and G respectively show histologic views of IRC mouse tissue, stained with HE, associated with a working electrode of an implanted glucose sensor at 1 dpi, 3 dpi, 7 dpi, and 14 dpi consistent with the present invention.

Histopathologic analysis of the tissue surrounding the WE indicated that at day 1 there was a moderate diffuse inflammatory process, characterized by necrosis, edema, fibrin deposition and the presence of both polymorphonuclear leukocytes (PMN's) and monocytes as shown in FIGS. 35A and 35B. By 3 DPI, the sensor was surrounded by dense band of inflammatory cells with some necrosis surrounding the implanted sensor as shown in FIGS. 35C and 35D. The inflammatory cells were primarily PMN's and macrophages. Adjacent to the dense inflammatory band, a diffuse region of inflammation characterized by numerous activated macrophages and fibroblasts with occasional lymphocytes was seen as shown in FIG. 35C. Initial collagen deposition was seen distal to the band of inflammatory cells surrounding the implanted glucose sensor as shown in FIG. 35D. By day 7 and 14 post sensor implantation the tissue reactions were characterized by the presence of large numbers of macrophages and activated fibroblasts surrounding the working electrode as shown in FIGS. 35E, 35H, and 35G. It was also noted that there was significant neovascularization of the tissue adjoining the working electrode. Giant cell formation particularly around the working electrode as early as 7 DPI was also observed as shown in FIG. 35. Trichrome staining of the day 7 and 14 tissue surrounding the working electrode demonstrated the presence of numerous activated fibroblasts associated with growing ribbons of collagen surrounding the working electrode as shown in FIGS. 35F and 35H. By day 30 the WE was surrounded by a dense band of inflammatory cells and activated fibroblasts as shown in FIGS. 37A and 37B, intermingled with a dense band of collagen as shown in FIGS. 37E and 37G. Thus, these experimental example shows that tissue reactions at sites of glucose sensor implantation in mouse skin include those due to the glucose oxides containing region of the sensor which function to induce sever tissue reactions that are associated with the loss of sensor function.

Figure 36:
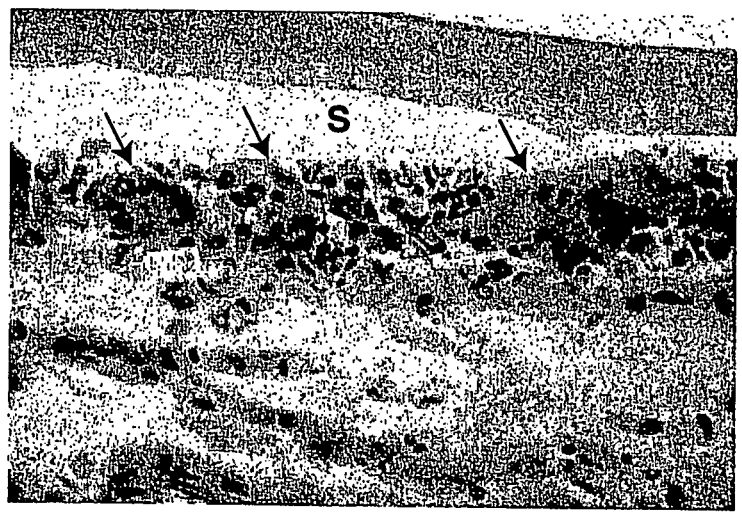
FIG. 36 shows a histologic view of mouse model tissue, which includes the presence of giant cells in association with a glucose sensor at 7 dpi consistent with the present invention.

Experimentally it was observed that significantly less inflammatory reactions occurred in the tissue surrounding the reference electrode as well as in the tissues surrounding the Teflon-coated wire, which joins the working electrode with the reference electrode as shown in FIGS. 35 and 36. At day 1 post implantation the tissue surrounding the reference electrode had light diffuse inflammation, characterized by the presence of PMN's and monocytes as well as edema and some fibrin deposition as shown in FIGS. 35I and 36J. It was noteworthy that there was relatively little tissue necrosis immediately surrounding the reference electrode, compared to what was seen surrounding the working electrode. At 3 days post sensor implantation, inflammation characterized by PMN's and macrophages was still present, but was localized close to the surface of the reference electrode as shown in FIGS. 35K and 35L. The inflammatory reactions did not extend significantly into the tissue adjoining the reference electrode as shown in FIG. 35K. Only wispy collagen fibers were seen in the tissue next to the inflammation as shown in FIG. 35L. At days 7 and 14 a low-grade inflammation, characterized by the presence of PMN's and macrophages, continued in close proximity to the surface of the reference electrode as shown in FIGS. 35M, 35N, 35O and 35P. There was an increased appearance of activated fibroblasts and loose collagen band formation as shown in FIGS. 35N and 35P. Neovascularization was limited and sparse in the tissue surrounding the reference electrode as shown in FIG. 35M and 35O. By 30 days post sensor implantation, the inflammatory reactions were still seen in close proximity to the surface of the reference electrode, with an increasingly dense layer of collagen seen bordering the inflammation as shown in FIGS. 37D and 37H. Although neovascularization was seen distal to the reference electrode it was dramatically less frequent and dense, compared to what was seen at the working electrode.

Experimental determination of glucose sensor functionality in vitro with varying glucose oxidase levels was undertaken. Glucose oxidase is known to cause tissue damage. Therefore, glucose sensors were prepared with varying concentration of glucose oxidase and its affect on sensor functionality and sensitivity was investigated. Briefly, glucose oxidase (20 mg/ml) at a serial dilution of 1:10 was immobilized using glutaraldehyde as a cross-linking agent and bovine serum albumin as a carrier protein. 1 μl of that mixture was applied three times to the working electrode with a break of 30 minutes between the single dipping procedures to allow the solution to dry on the surfaces. After dip-coating the sensors with 6 layers of Nafion® fluoropolymer-copolymer, they were cured for 0.5 hrs at 120° C. and stored dry at room temperature in closed containers. Sensor functionality was determined in PBS and with addition of glucose as described above. No sensor response was detected for glucose sensor with a glucose oxidase dilution of 1/1000. Glucose sensor with a glucose oxidase dilution of 1/10 of initial concentration showed a loss of sensor sensitivity of 50%. The lowest detectable sensitivity for glucose was detected in glucose sensors with a glucose oxidase dilution of 1/100 (1.8E-3 mg/ml GO). Since it had been demonstrated earlier that GO is extremely tissue toxic it was concluded that a GO concentration of 6 mg/ml (1.8E-2 mg/ml GO per sensor) is sufficient to reliable detect glucose levels in vivo. Experimentally this shows that the levels of glucose oxidase in a glucose biosensor affects the in vitro function of the sensor, and demonstrates that the minimum levels of glucose oxidase level required for detectable sensor function is about 0.6 mg/ml.

Since the in vitro data demonstrated that glucose oxidase (GO) is toxic to cells, it was investigated whether glucose sensors with a lesser amount of GO would reduce inflammation around the tissue of implanted glucose sensor. For this study, glucose sensors with various GO concentrations (3 consecutive serial 1/10 dilution's as described above) were implanted into the mouse model following the implantation protocol as described previously. Glucose sensor functionality and histologic evaluation was also conducted as described previously. Unexpectedly, glucose sensors with less GO showed same failure as non-diluted GO glucose sensors. However, histologic evaluation showed that tissue responses to glucose sensors with diluted GO had significantly less inflammation than glucose sensors with full concentration of GO.

One embodiment of the present invention includes an ATS-glucose sensor implanted in a mammal. It has been experimentally demonstrated previously that glucose sensors with a diluted concentration of glucose oxidase showed a glucose sensor response similar to non-diluted GO glucose sensor but showed less severe inflammation around the implantation side. Therefore, it was investigated as to whether a glucose sensor with ATS showed a better sensor lifetime. Briefly, glucose sensors (1/10 diluted GO) were dip-coated with Matrigel™ and were implanted into mice using procedures described previously. However, prior to closing wound side, 100 μl of Matrigel™/saline (3:2 ratio) was injected around glucose sensor side. Control mice received no Matrigel™ treatment. Glucose sensor function as described above was tested in each mouse immediately following implantation, designated as 1-hour post implantation (HPI), 5 HPI, 1-day post implantation (DPI), 2 DPI, 3 DPI, and 6 DPI. Between the sensor function tests, the mice were left unrestrained in their cages, without polarization of the sensor. Sensor sensitivity was calculated by a two-point calibration method wherein one point is taken at baseline and one point is taken at the peak glucose.

Figure 38:
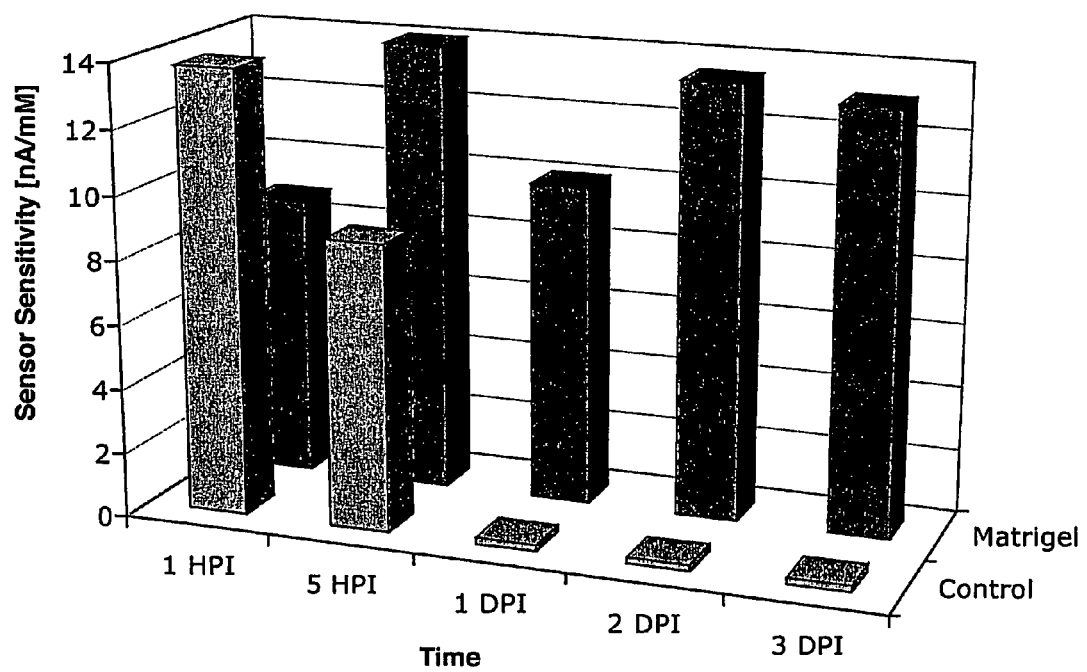
FIG. 38 is a graph showing function of glucose sensor in a mouse model consistent with the present invention.

To evaluate sensor function in our control mice and Matrigel™ treated mice, sensor function in the mouse was analyzed for between 1 HPI and 6 DPI. In these studies, glucose blood levels parallel sensor function at both 1 and 5 hours post sensor implantation. Analysis of blood glucose and sensor function at 1-day post sensor implantation clearly indicated that although the blood glucose levels were elevated by i. p. injection of the glucose, that there was little or no response from the implanted sensors in the control mouse. Analysis of the blood glucose and sensor function at 2, 3, and 6 days post sensor implantation consistently demonstrated that although blood glucose levels were elevated by i. p. injection of glucose, there was no sensor function in the control mouse as shown in FIG. 38. However, glucose sensor functionality in Matrigel™ glucose sensor treated mouse paralleled blood glucose levels. This behavior was consistent for time-points 1 HPI, 5 HPI, 1 DPI, 2 DPI and 3 DPI. Sensor sensitivity was in the range of under 10 to about 13 nA/mM for Matrigel™/sensor treated mouse at 1 DPI, 2 DPI and 3 DPI, as shown in FIG. 38. Thus, an ATS, such as Matrigel™, around a glucose sensor increases the lifetime of an implantable glucose sensor.

One embodiment of the present invention includes an implanted glucose sensor in a dexamethasone treated mouse model. Experimental glucose sensor implantation in dexamethasone treated mice was conducted the same way as described for control mice above. However, mice were treated with dexamethasone i. p. 24 hrs and 1 hr prior to sensor implantation. Control mice were not treated with dexamethasone at any given time-point. Mice were injected with dexamethasone i. p. on a daily basis. Daily inspection of the sensor implantation site was necessary to prevent loss of mesh. All mice were maintained under specific pathogen-free (SPF) conditions, at the Animal Facility of the University of Connecticut, Farmington Conn., according to Animal Care Procedures.

Figure 39:
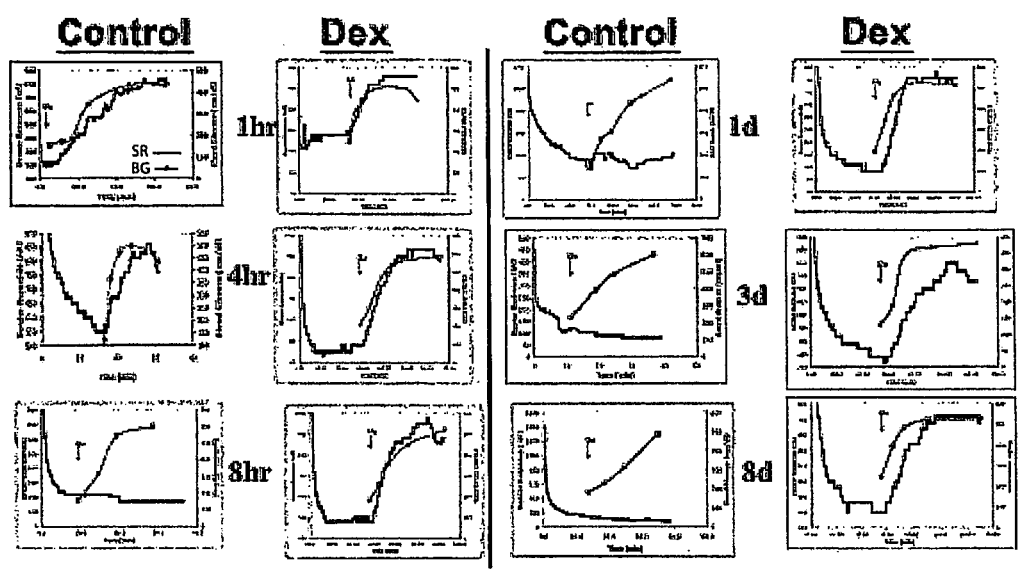
FIG. 39 show various graphs associated with blood glucose and sensor response in both control and dexamethasone treated mice at time points 1 hr, 4 hr, and 8 hrs consistent with the present invention.

Evaluation of sensor function in the mouse model was accomplished by analyzing sensor function in control mice and in the dexamethasone treated mice for 1 HPI and up to 8 DPI. In these studies, glucose blood levels parallel sensor function was monitored at both 1 and 5 hours post sensor implantation, as shown in FIG. 39 (4 hr and 8 hr), for both control mice, having no dexamethasone treatment, and dexamethasone treated mice. Analysis of the blood glucose and sensor function at 1 day post sensor implantation in the control mouse clearly indicated that although the blood glucose levels were elevated by i. p. injection of the glucose, that there was little or no response from the implanted sensors in the control mice as shown in FIG. 39 (1*d*). However, analysis of the dexamethasone mouse showed glucose levels paralleled sensor function. Analysis of the blood glucose and sensor function at 3, and 8 days post sensor implantation in the control mouse consistently demonstrated that although blood glucose levels were elevated by i. p. injection of glucose, there was no sensor function as shown in FIGS. 39 (3*d* and 8*d*). This rapid loss of sensor sensitivity and sensor function within the first day post implantation was seen in virtually all sensors tested in the control mouse model. Furthermore, the general pattern of loss of sensitivity and sensor function seen in our control mice was similar to that seen in both other animal models and man. On the other hand, glucose sensors implanted into mice treated with dexamethasone i. p. showed blood glucose levels paralleling sensor functionality. Thus, by controlling inflammation around an implanted glucose sensor it is possible to extend the lifetime and functionality of a glucose sensor. This experimentally demonstrates that systemic administration of dexamethasone dramatically enhance the function of a glucose sensor when implanted in the skin of mice.

One embodiment of the present invention includes a matrix material angiogenesis assay in a mammalian model. As previously shown experimentally, the gene transfer in the CAM model is used as a screen to establish "proof of principle" the concepts and tools (candidate genes) that are successful in the ex ova model need to be evaluated in mammalian models. A simple first step in this evaluation is to implant the chicken RCAS/DF-1 cells +/− the VEGF gene in immunodeficient mice (designated nu/nu). Immunodeficient are routinely used to grow cells from other species in vivo. Briefly, chicken VEGF:DF-1 and AS-VEGF:DF-1 (VEGF anti-sense gene control) cells were trypsinized to free from plate, centrifuged and re-suspended carefully with a 25 ml pipette in 20 ml serum-free media. An aliquot was removed and cells were counted with a hemacytometer. Cells were centrifuged again and re-suspended in 10 ml of serum-free media. For five animals $5\times10^6$ cells were placed into a 5 ml snap cap centrifuge tube. Cells were centrifuged and re-suspended in 0.3 ml serum-free media with the addition of 0.7 ml Matrigel™. Animals were anesthetized and each animal received 200 μl of Matrigel™/cell suspension on each side midway between flank and shoulder blades. As a control, cells without Matrigel™ were also injected into the skin of the mice at separate skins sites. Harvest was conducted after 8-days post injection by $CO^2$ asphyxiation and skin dissection to reveal matrigel pellet. Pellets were collected with the overlying skin and placed in fixative for 2 hours and then transferred to PBS for 3-4 hours followed by 70% ETOH and storage at 4° C. until processing for paraffin sections. Tissue samples were also obtained from the skin sites, which received cells without matrigel. The resulting tissue reactions were evaluated histologically. This experimental example teaches a method to construct and implant an ATS system composed of genetically engineered cells (chicken cells which overproduce the angiogenic factor VEGF) into an immunodefiecient mouse (nude/nude) in a Matrigel™, to determine 1) the ability of this ATS to induce neovascularization in the mouse model and 2) to protect the genetically engineered cells from destruction by tissue reaction i.e. inflammation.

Figures 41A, 41B, 41C:
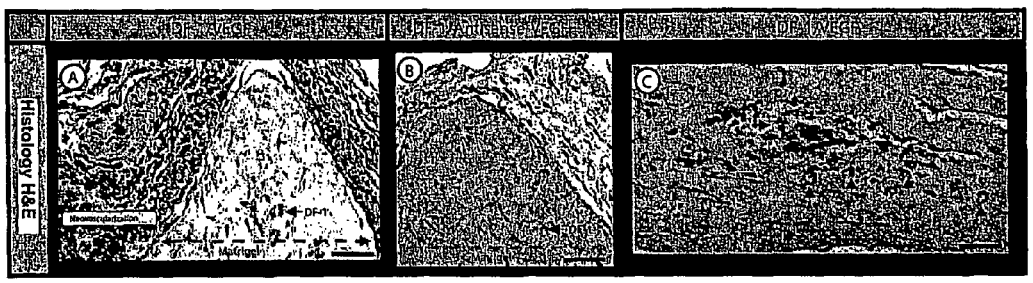
FIGS. 41A-C are histologic views of neovascularization induced in immunodeficient mice (nude/nude) by subcutaneous injection of VEGF:DF-1 containing ATS consistent with the present invention.

One embodiment of the present invention includes using VEGF:DF-1 to induce neovascularization in immunodeficient mice (nude/nude). Experimentally In order to determine if chicken VEGF:DF-1 cells entrapped in ATS system (Matrigel™) are capable of inducing neovascularization in mice, VEGF:DF-1 cells were suspended in Matrigel™ and injected s.q. in the back of the mice. Mice were sacrificed 8 days later, and the injected tissue was removed, fixed and processed for H&E staining. Mice injected with DF-1/antisence VEGF (AS-VEGF:DF-1) cells (controls), displayed no neovascularization around the Matrigel™ as shown in FIG. 41B. In contrast, mice injected with VEGF:DF-1 cells displayed a robust neovascularization around the Matrigel™ as shown in FIG. 41A), and in many cases the neovascularization penetrated the interior of the Matrigel™ as shown in FIG. 41 C, note that the arrows point to microvessels and indicate a colony of VEGF:DF-1 cells. It was also noted that tissue inflammation was minimal around the implanted ATS, and when present it did occur at the margins of the ATS, it did not penetrate into the ATS. This ability of the ATS system to 1) cause little tissue inflammation when implanted in vivo and 2) to block access of the inflammatory cells (i.e. inflammatory cells of innate immunity such as PMNs and macrophages) to the engineered cells in the ATS, resulted in protection of the cells within the ATS and enhancements of cell viability and function in vivo. Finally, it was observed that when the genetically engineered VEGF-DF-1 cells where injected into the skin of the mice without Matrigel™ the cells failed to induce any neovascularization. This clearly indicates the critical role of the Matrigel™ basement membrane in both promoting and protecting cells implanted at tissue sites, and underscores the importance of the matrix in both protecting the sensor as well as promoting cell survival and function at the site of ATS-sensor implantation. This experimental example shows that an ATS system composed of genetically engineered cells (chicken cells which overproduce the angiogenic factor VEGF) into an immunodeficient mouse (nude/nude) in a Matrigel™; this ATS system induces neovascularization into the ATS system only when the cells engineered to overproduce VEGF are in the ATS but not when control (VEGF anti-sense) engineered cells are in the ATS. Additionally, this experimental example demonstrates that the ATS induced minimal tissue inflammation when implanted and that basement membrane matrix (Matrigel™) appears to protect the engineered cells from destruction by the tissue inflammation, because the cell within the Matrigel™ were viable. Finally, this experimental example shows that Matrigel™ ATS is required to promote efficient neovasculariztion; e. g. cells injected into the skin of the mice without matrigel did not induce neovascularization, thus indicating the important role of the matrix material, for example basement membranes, in the ATS in cell viability in vivo.

One embodiment of the present invention includes the use of an ATS which includes Matrigel™, or other matrix material, in combination with various cells and a sensor. For example: Matrigel™+normal vascular stem cells+sensors; (Matrigel™+cytokines bound to matrigel)+normal vascular stem cells+sensors; Matrigel™+normal vascular stem cells+ engineered support cells+sensors; Matrigel™+normal vascular stem cells+engineered stem cells+sensors; (Matrigel™+ cytokines bound to matrigel)+normal vascular stem cells+ engineered support cells+sensors; and (Matrigel™+ cytokines bound to Matrige™)+normal vascular stem cells+ engineered stem cells+sensors.

One embodiment of the invention includes an ATS having stem cells as a constituent. Stem cells, which are the basic cellular building blocks of tissues and therefore organisms, are currently being considered for replacement of damaged or non-functional cells and tissues in various diseases. These stem cells are extremely plastics cells, and can be induced by a variety of proteins (cytokines and growth factors), drugs and matrices to proliferate and differentiate into specific adult cells. These stem cells can be included in the ATS for use in conjunction with implantable devices. For example, various combinations of stem cells and/or engineered stem cells, in association with other categories of cells, factors and matrices, may be used to create an extremely versatile ATS for implantable devices. These stem cells will be used to develop a device friendly environment by 1) insitu proliferation and differentiation into the ATS, 2) inducing specific in growth device friendly cells, matrices and factors from the tissue surrounding the implanted ATS-device and 3) inhibiting the in growth of cells, matrices and factors from the tissue surrounding the implanted AST-device, and 4) functioning as a support cell system to nurture and replace non-stem cell populations in the ATS.

Figure 40:
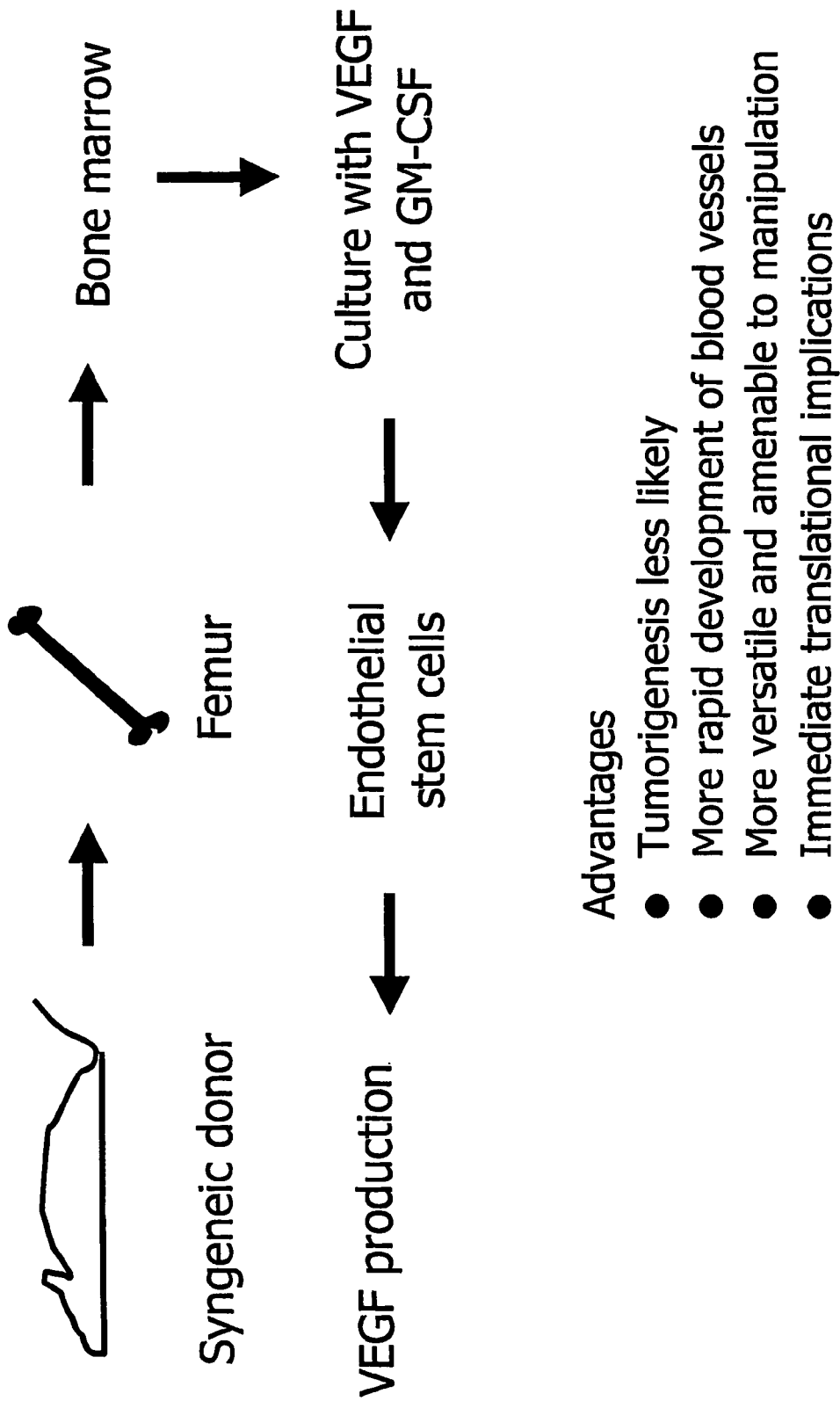
FIG. 40 is a diagram showing utilization of endothelial stem cells consistent with the present invention.

One embodiment of the present invention includes the prophetic examples of how stem cells could be used in ATS to enhance the function and life span of an implantable device placed into the ATS. For example, vascular endothelial cell (VEC) stem cells could be used to induce neovascularization in ATS to thereby enhance the function of implantable sensors. Experimentally, as shown in FIG. 40, this can be accomplished by obtaining surgically the long bones from adult mice. The ends of the bones are then removed. Next, tissue culture media is perfused thru the bones to flush out bone marrow cells, which are the source of the vascular endothelial cells stem cells. The bone marrow cells are cultured in vitro for several days in the presences of the cytokines, VEGF and GM-CSF, to induce differentiation of the bone marrow cells into vascular endothelial cells. The induction of the endothelial cell phenotype is detected using Immunoassays (immunocytochemistry or FACS analysis) to detect expression of CD34 on the surface of the vascular endothelial cells. The CD34 positive cells (CD34+) are then incorporated into a matrix material such as, Matrigel™, and assembled with the implantable glucose sensor as described above. The resulting ATS (with stem cells)-sensor complex is then implanted SQ into the neck of the recipient mice.

In one embodiment of the present invention, the ATS-sensor complex can be assembled in vivo but first injecting the Matrigel™-stem cell combination into the skin of the mice followed by the insertion of the sensor into the matrigel-cell mixture preinjected into the mouse skin.

In one embodiment of the present invention, at various days post implantation, for example at 1, 3, 7, 14, 30, 60, and 180 days, the mice are evaluated for glucose sensor function as previously described in the experimental examples. For example, for sensor function evaluation, the mice are injected i.p. with a glucose solution at pre-selected times the blood glucose levels as determined directly and correlated with the output of the implanted sensors. As controls for these studies sensor can be implanted without any stem cell ATS, and with only Matrigel™ and the device.

One embodiment of the invention includes using human blood mononuclear cells as a source of stem cells. Experimentally these human blood monocytes are isolated using Histopaque and cultured in basic endothelial cell media (Clonetics) with EGF, VEGF, FGF-b IGF-1, ascorbic acid and heparin for 8-12 week to induce endothelial stem cells. The resulting endothelial cells will be verified using anti-CD34 immunoassays, and combined with a matrix material, for example Matrigel™, to form the basic ATS system. The vascular endothelial cell stem cell Matrigel™ ARS can be assembled with the glucose sensor in vitro or in vivo as described in the above experimental examples. The in vivo function of the ATS-Sensor complex can be tested in nude mice. Nude mice (athymic) will be used to prevent rejection of the human stem cells since the recipient host is murine not human. Once these experimental studies are completed studies using human stem cells based ATS-sensor assemblies can be done, for example, in human hosts.

One embodiment of the present invention includes using an ATS having vascular endothelial cell (VEC) stem cells and a matrix material, for example Matrigel™ in addition to including cytokines and/or cytokine producing support cells, to Induce, for example neovascularization for the purpose of enhancing the function of implantable sensors.

One embodiment of the invention includes using the ability of the local expression of SDF-1, a know inducer of endothelial stem cells, to induce neovascularization in conjunction with vascular endothelial stem cells in vivo. For these studies two general approaches may be used.

In the first approach, an addition of recombinant SDF-1 to, for example, Matrigel™ is made prior to the addition of the stem cells and glucose sensor, to create a depot of SDF-1 which will stimulate the differentiation of the stem cells into vascular endothelial cells that will directly promote neovascularization and or directly form blood vessel (vasculogenesis). Implantation into, for example, mice can the be made and the mice can be evaluated at various times for glucose sensor function as described above.

In a second approach mouse fibroblasts which over-express SDF-1 can be prepared in a fashion similar as was done for the VEGF over-expressing fibroblast as previously described. The SDF-1 over expressing fibroblast can then be mixed with vascular endothelia cell stems cells in a matrix material, for example Matrigel™ in order to form the ATS. The ATS can then be combined with the glucose sensor in vitro or in vivo and then implanted into the mice and evaluated at various times for glucose sensor function as described previously.

On embodiment of the present invention includes an ATS having genetically engineered vascular endothelial cell (VEC) stem cells and a matrix material to induce neovascularization thereby enhancing the function of implantable sensors One embodiment of the present invention includes using stem cells to induce neovascularization in vivo at sites of sensor implantation by engineering the stem cells themselves to over express angiogenic factors and/or stem cell factors. For this approach stem cell models as described above can be used. However, the cells can be genetically engineered such that the stem cells over produce pro-neovascularization cytokines such as VEGF and/or stem cell factors such as SDF-1.

One embodiment of the present invention includes combining various stem cells and engineered stem cells in the a matrix material, for example Matrigel™, to form and ATS in order to enhance neovascularization and sensor function in vivo. For example, the following combinations could be made:

Combination 1: Normal VEC stem cells plus VEGF-over expressing stem cells.
Combination 2: normal VEC stem cells plus SDF-1 over expressing Stem cells
Combination 3: normal VEC stem cells plus VEGF-over expressing stem cells and SDF-1 over expressing Stem Cells The various combination of normal and engineered stem cells described above can be added to the Matrigel™ to form an ATS which is then combined with the glucose sensor in vitro or in vivo. An implantation is made into mice and evaluated at various times for glucose sensor function as described above.

In one embodiment of the invention there are a wide variety of methods employed for gene transfer in cells and tissue. Three of the major approaches used include: 1) plasmid based gene transfer, 2) retrovector based gene transfer and adenovector based gene transfer. Plasmid based gene transfer utilizes "naked" DNA to directly transfer genetic information into cells in vitro and or in vivo. Plasmid based gene transfer has the advantage that it is simple, but it is extremely inefficient particularly in vivo. Retrovector based gene transfer utilizes retroviral vectors to "carry" the selected genetic information into the cells via specific virus receptors on the surface of target cells. Retrovectors have the advantage in that they are extremely stable, but they require a selection procedure, which identifies cells in which the genes have successfully been transferred. Adenovectors, like retrovectors utilizes adenoviral vectors to "carry" the selected genetic information into the cells via specific virus receptors on the surface of target cells. Adenovectors have the advantage of being very efficient in gene transfer also the gene expression may be transient. Generally for gene therapy, adenovectors have been the system of choice. Adenovirus binds to a surface receptor known as CAR, and CARs have been identified on human (hCAR) and murine cells. Unfortunately not all cells have high enough levels of CAR to allow infection with adenovectors, thus limiting the spectrum of target cells in which gene transfer can be achieved. For example, generally fibroblasts have limited levels of CAR and thus are not used as target cells for adenovector based gene transfer. For the ATS a protocol for genes transferred into target cells that are CAR deficient, thus allowing the use of adenovector in these cells.

Figure 42:
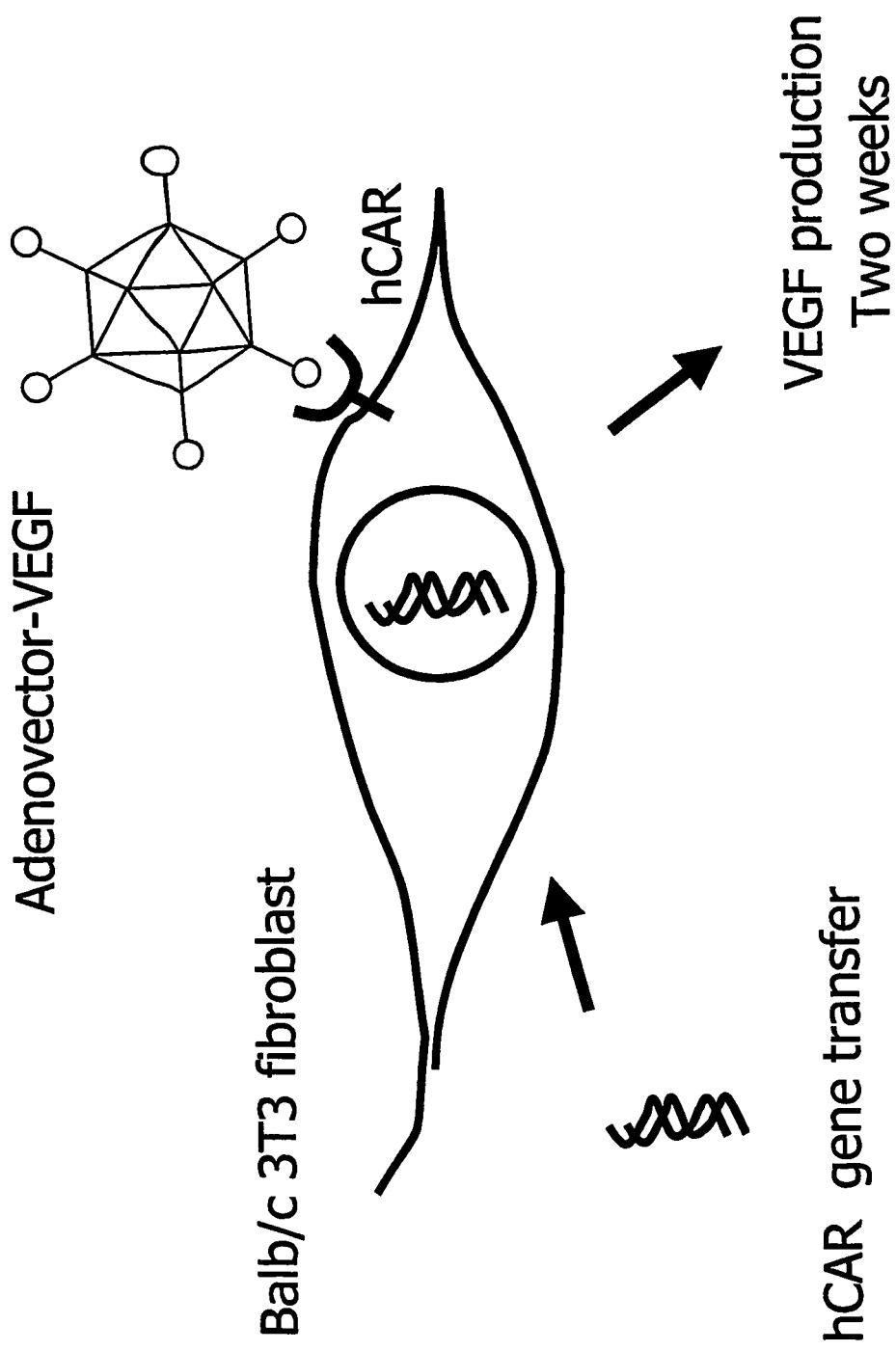
FIG. 42 shows a human coxsackievirus and adenovirus receptor (hCAR) consistent with the present invention.

For example, as shown in FIG. 42, a prophetic experiment includes an adenovector based gene transfer in cells that contain little or no CAR can be achieved by first transferring the CAR gene into the CAR deficient cell, demonstrating CAR expression, and finally transferring the gene of choice into the CAR transfected cell. To achieve this can first culture NIH 3T3 mouse fibroblasts at a concentration of 3E5 cells. Supercoiled plasmid containing mouse CAR or human_CAR genes is then added to the cells in DMEM containing lipofectamine and incubated at room temperature. Next, the cells-plasmid-lipofectamine culture is transferred to 37° C. and 5% $CO_2$ for 5 hours. After the 5 hr time frame, 2 ml of 10% FBS is added to the culture and it is incubated at 37° C. and 5% $CO_2$. CAR expression in the cells is then determined by immunocytochemistry and western blot technology using an antibody that is specific for mouseCAR (mCAR). The resulting mCAR positive cells can be tested for gene transfer using adenoviral vectors containing green fluorescence protein gene (GFP), human VEGF genes or mouse VEGF genes by incubation of the CAR positive 3T3 fibroblast with these viral vectors individually. The resulting transfected cells can be tested for successful gene transfer by 1) evaluating the GFP transfected cells for green fluorescence appearance under direct microscopic evaluation; 2) evaluating expression of mouse VEGF expression by immunoassays (ELISA and Western blot) using an antibody specific for mouse VEGF; 3) evaluating expression of human VEGF expression by immunoassays (ELISA and Western blot) using an antibody specific for human VEGF. The resulting mouse VEGF or human VEGF 3T3 fibroblast can then be added to matrigel and inject s.q. in the skin of mice to determine there ability to induce new blood vessel formation using standard histological evaluation of the tissue obtained from the site of implantation. The 3T3 cells that successfully induce new blood vessel formation in the mouse skin can then be used in the ATS with the implantable glucose sensor to determine the ability of these genetically engineered cells to enhance glucose sensor function in vivo.

In one embodiment of the present invention artificial skin may be utilized. Artificial skin, as a tool to promote the regeneration and repair of injured tissues, e.g. skin of burn victims, and repair of ulcerated skin, has seen growing acceptance in the medical community in recent years. Initially artificial skins were composed of temporary acellular materials, which where used to protect the injured skin from infection and dehydration, while repair and regeneration of the skin were occurring. More recently artificial skins have become increasing complex assemblies of synthetic polymers and natural products, including cells. These "artificial skins" can utilized to enhance and or protect implantable devices, such as glucose sensors by including the use of various techniques, teachings, suggestions, and protocols disclosed herein.

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

What is claimed is:

1. An implant system, comprising:
    (a) a sensor having an outer surface including an analyte permeable coating,
    (b) a biological matrix comprising a cell culture derived basement membrane exterior to the sensor and in contact with the analyte permeable coating on the outer surface of the sensor and with biological tissue, and
    (c) a plurality of cells supported by the biological matrix, the plurality of cells comprising cells expressing vascular endothelial growth factor and extending sensor functionality by promoting a biological interaction between the sensor and the biological tissue.

2. The implant system of claim 1, wherein said cells expressing vascular endothelial growth factor include at least one member selected from the group consisting of biological cells, engineered cells, support cells, stem cells, artificial cells and hybrid cells.

3. The implant system of claim 1, wherein said biological tissue comprises mammalian tissue.

4. The implant system of claim 1, wherein said sensor is an amperometric glucose sensor.

5. The implant system of claim 1, wherein said sensor is a glucose sensor.

6. The implant system of claim 1, wherein said biological matrix at least partially embeds said sensor.

7. The implant system of claim 1, wherein the plurality of cells comprise cells that are configured to suppress deleterious reactions between said sensor and said biological tissue and/or said biological matrix.

8. An implant system comprising:
    (a) an implantable sensor having an outer surface including an analyte permeable coating,
    (b) a biological matrix comprising cell culture derived basement membrane, the biological matrix being positioned exterior to the sensor and in contact with the analyte permeable coating on the outer surface of the sensor, and
    (c) a plurality of cells supported by said biological matrix, the plurality of cells comprising cells expressing vascular endothelial growth factor and being configured to extend sensor functionality when the sensor and matrix are implanted in biological tissue by promoting neovascularization of the biological tissue.

9. An implant system in biological contact with biological tissue comprising:
    (a) a cellular component, said cellular component includes at least one cellular community comprising cells expressing vascular endothelial growth factor;
    (b) a biological matrix material comprising a cell culture derived basement membrane in contact with the biological tissue, said biological matrix material being associated with a portion of the cellular community; and
    (c) a sensor having an outer surface including an analyte permeable coating in contact with the biological matrix material, at least one of the biological matrix material and the cellular community extending sensor functionality by promoting neovascularization of the biological tissue,
    wherein the biological matrix is exterior to the sensor.

10. The implant system in biological contact with the biological tissue of claim 9, wherein the biological tissue is mammalian tissue.

11. The implant system of claim 9, wherein the cellular component comprises a cellular community that inhibits at least one of inflammation and fibrosis.

12. The implant system of claim 1, wherein the system is configured to test the effectiveness of the sensor.

13. The implant system of claim 8, wherein the sensor comprises a glucose sensor.

14. The implant system of claim 1, wherein said plurality of cells comprise cells that induce the growth of new tissue exterior to the sensor.

15. The implant system of claim 14, wherein said new tissue comprises vascular structures.

16. The implant system of claim 8, wherein said implant system further comprises at least one genetic element supported by said matrix.

17. The implant system of claim 8, wherein said system further comprises at least one response modifier supported by said matrix.

18. The implant system in biological contact with the biological tissue of claim 9 wherein the cellular component includes at least one member selected from the group consisting of normal vascular stem cells; a combination of normal vascular stem cells and engineered support cells; and a combination of normal vascular stem cells and engineered stem cells.

19. The implant system in biological contact with the biological tissue of claim 18, wherein the basement membrane has at least one of cytokines and growth factors bound thereto.

20. The implant system in biological contact with the biological tissue of claim 9, wherein at least a portion of the cellular community is bound to the biological matrix.

21. The implant system of claim 14, wherein the new tissue comprises capillaries.

22. The implant system of claim 1, wherein the cells comprise at least one member selected from the group consisting of cells that inhibit inflammation and cells that inhibit fibrosis.

23. The implant system of claim 8, wherein the cells comprise at least one member selected from the group consisting of cells that inhibit inflammation and cells that inhibit fibrosis.

* * * * *